US012239113B2

(12) United States Patent
Hicks et al.

(10) Patent No.: US 12,239,113 B2
(45) Date of Patent: Mar. 4, 2025

(54) LIVESTOCK MANAGEMENT

(71) Applicant: HerdX, Inc., Boerne, TX (US)

(72) Inventors: Ronald B. Hicks, Boerne, TX (US);
Sarah C. Harkleroad, San Antonio, TX (US); Jay D. J. Pennington, Boerne, TX (US); Alan W. Neidig, Round Rock, TX (US); Robert T. Buczkiewicz, West Bend, WI (US)

(73) Assignee: HerdX, Inc., Boerne, TX (US)

( * ) Notice: Subject to any disclaimer, the term of this patent is extended or adjusted under 35 U.S.C. 154(b) by 0 days.

(21) Appl. No.: 18/376,349

(22) Filed: Oct. 3, 2023

(65) Prior Publication Data

US 2024/0023516 A1  Jan. 25, 2024

Related U.S. Application Data

(62) Division of application No. 15/842,826, filed on Dec. 14, 2017, now Pat. No. 11,771,057.

(Continued)

(51) Int. Cl.
*A01K 7/02* (2006.01)
*A01K 11/00* (2006.01)
(Continued)

(52) U.S. Cl.
CPC ................ *A01K 7/02* (2013.01); *A01K 11/00* (2013.01); *A01K 11/006* (2013.01); *A01K 29/00* (2013.01); *A01K 29/005* (2013.01); *A01K 39/012* (2013.01); *C02F 1/008* (2013.01); *C02F 1/461* (2013.01); *G01N 33/18* (2013.01); *B64U 10/13* (2023.01); *B64U 2101/30* (2023.01); *C02F 2103/20* (2013.01); *C02F 2209/008* (2013.01); *C02F 2209/04* (2013.01); *C02F 2209/05* (2013.01); *C02F 2209/06* (2013.01); *C02F 2209/29* (2013.01); *C02F 2209/40* (2013.01); *C02F 2209/42* (2013.01)

(58) Field of Classification Search
CPC ........ A01K 7/02; A01K 7/025; A01K 29/005; A01K 11/006; A01K 11/004; A01K 29/00; A01K 11/00; A01K 39/012; A01K 39/02; A01K 39/026; A01K 39/04; A01K 7/00; A01K 25/16
See application file for complete search history.

(56) References Cited

U.S. PATENT DOCUMENTS

2012/0089340 A1* 4/2012 Huisma ............. G01G 19/4146
                                                    702/19
2016/0227738 A1* 8/2016 Ausman ............. A01K 5/0142
(Continued)

Primary Examiner — Trinh T Nguyen
(74) Attorney, Agent, or Firm — Jackson Walker LLP

(57) ABSTRACT

Livestock may be managed by a variety of systems, processes, and techniques. In particular implementations, the properties of water may be monitored by automated techniques and treated water may be provided to animals. In certain implementations, sick, or potentially sick, livestock may be provided with treated water to improve their health. The automated techniques may include monitoring the movements and/or water consumption of the livestock and predicting which ones may be sick based on their movements and/or water consumption. In some implementations, a water trough may contain multiple segments. The water properties in the segments may be maintained at different states.

26 Claims, 22 Drawing Sheets

Related U.S. Application Data

(60) Provisional application No. 62/585,408, filed on Nov. 13, 2017, provisional application No. 62/434,341, filed on Dec. 14, 2016.

(51) Int. Cl.
| | |
|---|---|
| *A01K 29/00* | (2006.01) |
| *A01K 39/012* | (2006.01) |
| *C02F 1/00* | (2023.01) |
| *C02F 1/461* | (2023.01) |
| *G01N 33/18* | (2006.01) |
| *B64U 10/13* | (2023.01) |
| *B64U 101/30* | (2023.01) |
| *C02F 103/20* | (2006.01) |

(56) References Cited

U.S. PATENT DOCUMENTS

| | | | |
|---|---|---|---|
| 2016/0286757 A1* | 10/2016 | Armstrong | A01K 7/02 |
| 2016/0366858 A1* | 12/2016 | Seltzer | A01K 29/005 |
| 2017/0000083 A1* | 1/2017 | McAdams | F16K 15/1825 |
| 2017/0006826 A1* | 1/2017 | Torres | A01K 13/003 |
| 2017/0013802 A1* | 1/2017 | Zimmerman | G06K 7/10366 |
| 2017/0065499 A1* | 3/2017 | Richards | A01K 11/006 |
| 2017/0086428 A1* | 3/2017 | Horton | G16H 40/67 |
| 2017/0196203 A1* | 7/2017 | Huisma | G08C 17/02 |
| 2017/0202185 A1* | 7/2017 | Trumbull | A01K 29/005 |
| 2020/0137983 A1* | 5/2020 | Nieveen | A01K 29/005 |
| 2020/0178495 A1* | 6/2020 | Womble | A01K 1/0353 |

\* cited by examiner

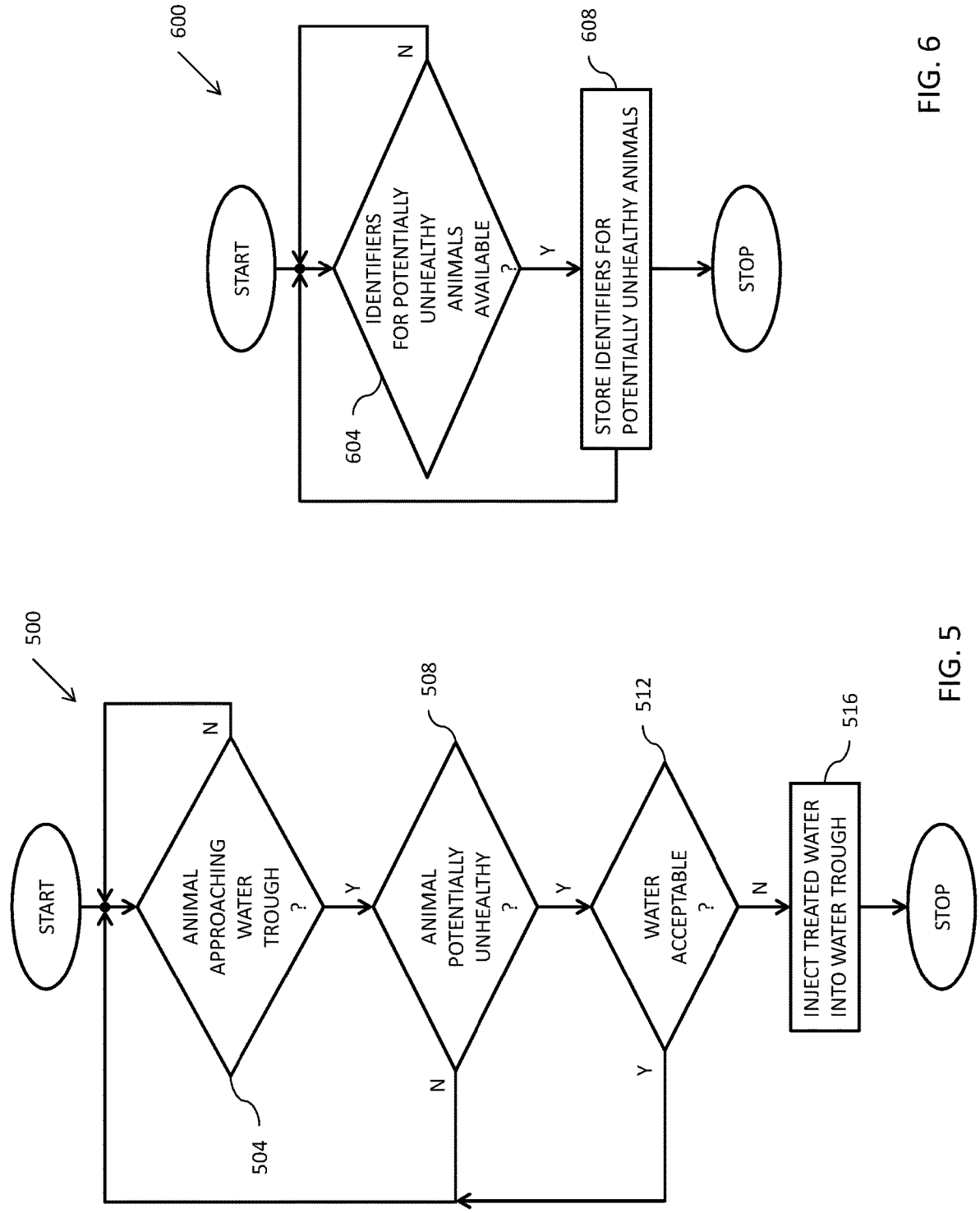

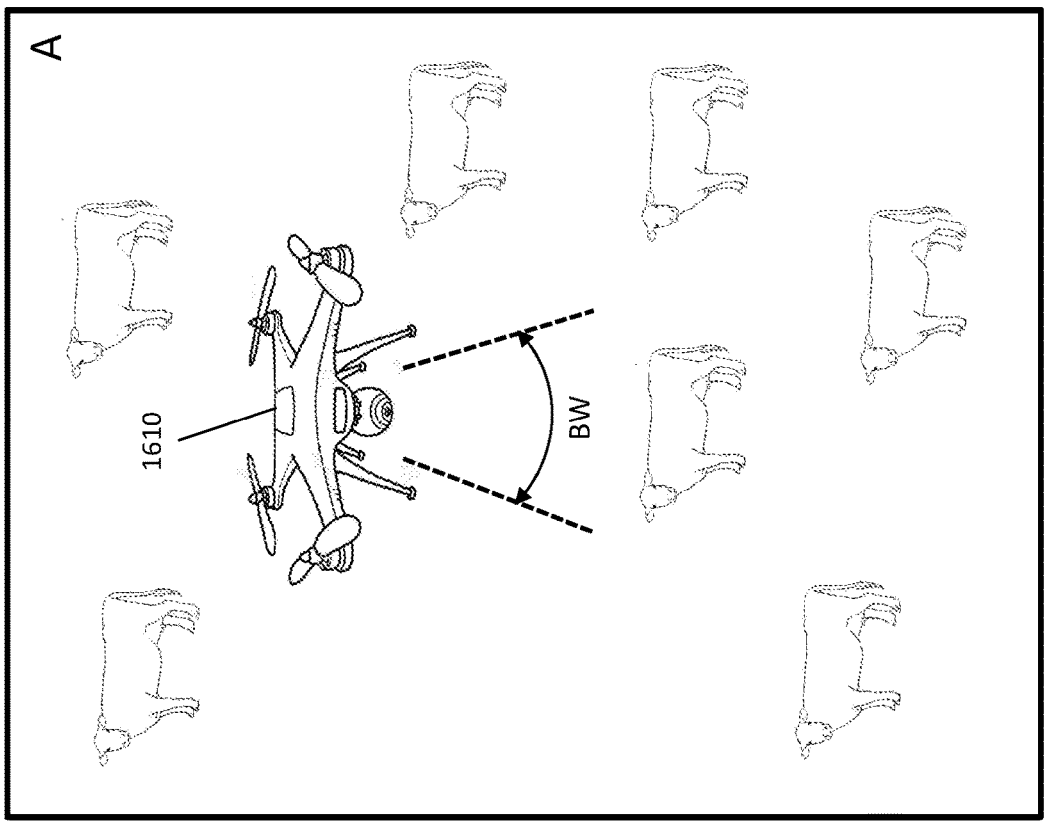
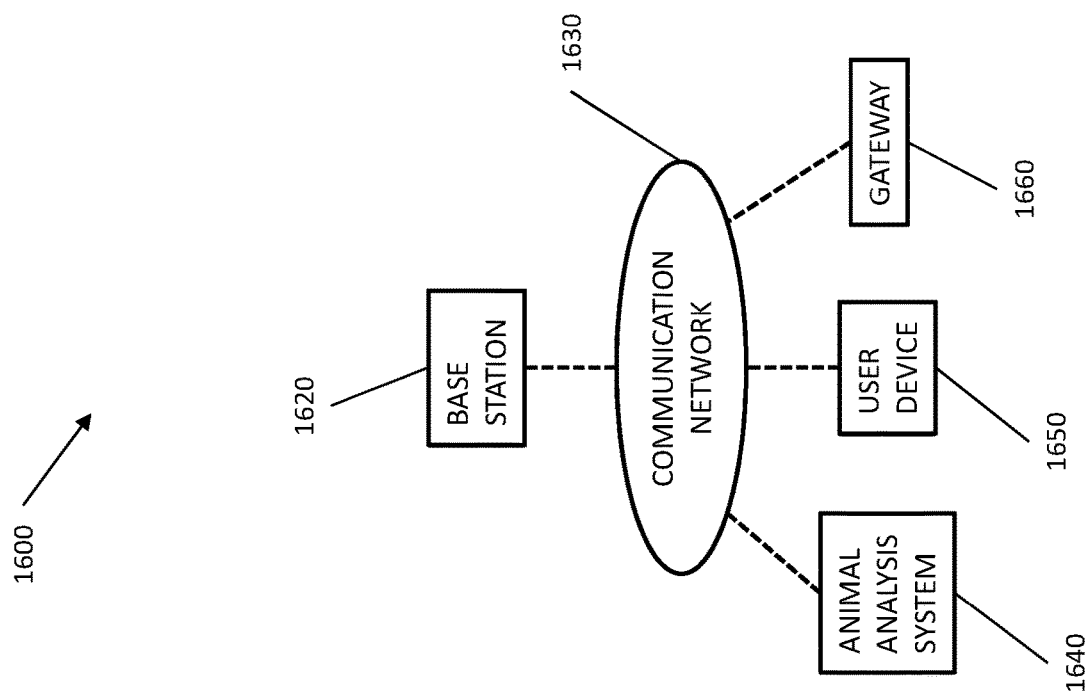
FIG. 16

LIVESTOCK MANAGEMENT

RELATED APPLICATIONS

This application is a divisional of U.S. patent application Ser. No. 15/842,826, filed Dec. 14, 2017, which claims priority to U.S. Patent Application No. 62/434,341, filed Dec. 14, 2016, and U.S. Patent Application No. 62/585,408, filed Nov. 13, 2017. These prior applications are herein incorporated by reference in their entirety.

TECHNICAL FIELD

This invention relates in general to management of animals and, more particularly, to comprehensive systems and methods for assessing livestock health and providing nutritional supplements.

BACKGROUND

Feeding facilities (e.g., feedlots or feed yards) are critical to the world's food supply. But managing them efficiently presents many challenges. For example, upon arrival at a typical cattle feedlot, each member of the herd will make at least one trip through a chute, where handlers often can afford to spend only about 45 seconds processing each animal. Initial processing typically involves some variation of each of the following: (1) standard treatment such as spraying, deworming, and antibiotics; (2) when feasible, some level of assessment and any special treatment that may be indicated based on the assessment; and (3) identification by attaching either an RFID ear tag, a numbered or barcoded ear tag, or some other form of individual animal identification. Other processing activities can include vaccination, castration, horn-tipping, weighing, etc., all of which can help in managing the herd. Naturally, with whatever processing takes place, records also need to be created, updated, and transferred for each cow (e.g., calf, heifer, steer, bull, etc.) being processed.

Challenges arise from the need for speed versus trying to determine what particular type of treatment is needed for each individual cow, which can be quite difficult. When a feedlot omits a critical treatment, it can quickly lose a large part of the herd.

In the United States' cattle industry, annual mortality of cattle due to disease is estimated to be in the hundreds of millions of dollars. A reliable method of determining the health of a cow or the presence of disease is by assessing the body temperature of the animal. In the case of infections, environmental factors, or toxins, a cow's temperature will elevate. These elevations are diagnostic to veterinarians in the diagnosis of disease and disease conditions in cattle. In the day-to-day production of cattle, the evaluation of the presence of increased body temperature or fever is underutilized due to time constraints and the need to physically restrain the animal. This underutilization of temperature evaluation delays the diagnosis of disease and therefore increases the ineffective uses of medications and loss of animals.

So, rather than attempt to predict which cows need treatments and which do not, the feedlot industry is constantly facing temptations to mass treat all animals entering a feedlot as a precaution. But mass antibiotic treatment of an entire herd of potentially at risk cattle is not only expensive, it presents a litany of concerns for beef quality and microbial mutation. Regulatory agencies (e.g., FDA or USDA, under Presidential Executive Order 13676) recognize the pending microbial resistance public health crisis (as outline by WHO and other world agencies) that therefore strongly discourage overuse of antibiotics in order to minimize the risk of microbial mutation, practically outlawing Gentamicin Sulphate and blended cocktail treatments for use in bovine applications. In addition, consumers show a strong demand for beef that is free from additives and antibiotics, and was raised in a more environmentally friendly way. Thus, there has long been a huge need to improve herd processing through more accurate assessments and more intelligent treatments.

Other herd management practices have been advancing more systematically than livestock assessment techniques, particularly in the area of livestock tagging. Tags applied to each cow are used to identify the particular cow and are typically applied in the ear where they can be readily seen and tracked. Radio Frequency Identification ("RFID") technology is being utilized to a greater extent in the agricultural industry. Also, more and more historical data is being required by regulatory agencies before a calf can be slaughtered or packed.

At least three companies have attempted to help ranchers manage cattle based on temperature, but their attempts have been less than ideal. Tekvet [website: tekvet.com], Fever Tags LLC [website: fevertags.com], and Quantum Ag Products have launched systems of mobile temperature monitors (e.g., a surface-based thermistor mounted in the calves' ears and a temperature sensor in the calves' ear, respectively), which link to a base station.

Other efforts have been directed at using the core (i.e., internal) temperature, or more precisely the temperature of the blood as it flows in or near the pulmonary artery near the heart, to determine health. Unfortunately, core temperature has been difficult to measure accurately without invasive placement in the sensitive interior of the body. Bella AG has an invasive sensor, Bolus, but it has proved difficult to scan.

SUMMARY

Livestock may be managed by a variety of systems, processes, and techniques. In particular implementations, the properties of water may be monitored by automated techniques and treated water may be provided to animals. In certain implementations, sick, or potentially sick, livestock may be provided with treated water to improve their health. The automated identification techniques may include monitoring the movements and/or water consumption of the livestock and predicting which ones may have health conditions based on their movements and/or water consumption. For example, movements of cows may be used to predict which cows are sick. Livestock that is sick may be may be provided with treated water by providing the treated water to a trough when a potentially sick animal approaches.

In particular implementations, a livestock management system may include a trough, a sensor array, a controller, a water treatment unit, and a controller. The trough may be adapted to hold water for animal consumption and include an inlet adapted to receive water being injected into the trough. The sensor array may be coupled to the trough and adapted to detect an amount of water in the trough or at least one property of water in the trough. The water treatment unit may be coupled to the trough and adapted to alter at least one property of water being injected into the trough. The controller may be adapted to regulate the injected water based on the detected amount of water in the trough and/or the detected water property.

In certain implementations, the sensor array may include a first sensor adapted to detect a level of water in the trough and a second sensor adapted to detect at least one property of water in the trough (e.g., oxygen reduction potential, mineral/nutrient presence, or potential hydrogen). The controller may be adapted to regulate the injected water based on the detected water property and/or the water level. The controller, in certain modes of operation, may be adapted to inject water into the trough regardless of the water level in the trough.

In some implementations, the system may include a sensor adapted to detect a property of water being supplied to the water treatment unit. The controller may be adapted to regulate the water treatment unit based on the detected inflow water property.

In particular implementations, the system may include a proximity sensor adapted to detect the presence of an animal near the trough. The controller may be adapted to regulate injection of water into the trough in response to the presence of an animal. Additionally, the controller may be adapted to determine the health status of a detected animal and inject treated water into the trough based on the health status of the detected animal.

In certain implementations the trough may include a first segment adapted to hold water for animal consumption, the first segment including the inlet for receiving water, a second segment adapted to hold water for animal consumption, and a wall dividing the first segment from the second segment, the wall adapted to allow water from the first segment to flow into the second segment. The sensor array may include a first sensor adapted to detect the level of water in the second segment and a second sensor adapted to detect at least one property of water in the first segment. The wall may be located near one end of the trough to inhibit an animal's head from accessing a lower portion of the trough between the end and the wall, and the second sensor may be located in the lower portion of the trough between the end and the wall. The sensor array may also include a third sensor adapted to detect at least one property of water in the second segment. The wall may also be adapted to shield the third sensor.

The controller may be adapted to inject water into the first segment in response to at least one property of water in that segment. Additionally, the controller may be adapted to inject water into the first segment regardless of the water level in the second segment and/or to inject water into the first segment in response to the level of water in the second segment.

In certain implementations, the second segment includes an outlet adapted to dispense water, the outlet being located above the wall.

In particular implementations, a system for controlling water delivery to an animal water trough may include a radio-frequency tag adapted to be placed on an animal, a first radio-frequency sensor adapted to detect the approach of an animal to a water trough, and a second radio-frequency sensor adapted to detect the arrival of an animal at the water trough. The first radio-frequency sensor may detect an approaching animal at about 10 m, and the second radio-frequency sensor may detect an approaching animal at less than 1 m.

The system may also include a processor adapted to: determine whether an animal is approaching the water trough; determine the animal's health classification based on whether the animal is approaching the water trough; determine whether the animal requires treated water based on the animal's health classification; and inject treated water into the trough based on the animal's health classification. The processor may be further adapted to determine whether the trough water is acceptable based on the animal's health classification and inject treated water into the trough based on the acceptability of the trough water.

In some implementations, the processor may be further adapted to determine whether the animal arrives at the trough, determine when the animal leaves the trough based on whether it arrives at the trough, and store the animal's trough arrival time and dwell time. The processor may also be adapted to determine a health classification for the animal based on the time between its visits to the water trough and its dwell time during the visits.

The first radio-frequency sensor and the second radio-frequency sensor may be mounted on the water trough. In certain implementations, the second radio-frequency sensor may include a coaxial cable having a perforated shield, which may embedded in the water trough.

Particular implementations may include a third radio-frequency sensor adapted to detect the approach of an animal to the water trough.

Some implementations may include an unmanned aerial vehicle adapted to fly over an area where livestock is located and scan for animal mounted tags. The unmanned aerial vehicle may be adapted to sequentially pass over the area to scan the entire area for animal tags. Additionally, the unmanned aerial vehicle may be adapted to activate a camera if a particular animal is sensed while flying over the area. The unmanned aerial vehicle may read and write data to a tag on an animal.

Various systems, processes, and techniques described herein may have one or more features. For example, being able to monitor and provide treated water ensures that livestock receives beneficial water. The treated water may increase hydration, raise the pH balance of the cows, and improve their antioxidant capability, helping them to fight off disease without having to use as many antibiotics. This should also provide higher quality animals, fewer herd losses, increased feedlot profitability, and potential cost savings, as well as reduce the environmental footprint of large feedlot operations.

Additionally, being able to provide treated water on demand (e.g., when an animal approaches) allows the treated water to be generated in a judicious manner, resulting in a more efficient use of resources and treated water. Additionally, being able to identify animals allows treated water to be specifically targeted to certain animals, which increases their health, and allows the water to be generated even more efficaciously. Moreover, the dosing of the water may be controlled based on animal identity. Thus, the systems, processes, and techniques may provide an environmentally sound solution as they improve animal health while conserving electricity. While providing treated water for all animals (e.g., healthy, potentially sick, and sick) is possible, it requires quite a bit of electricity for the water treatment process.

Furthermore, being able to track livestock provides the ability to identify animals with health conditions (e.g., sick) in an automated and individualized manner. This reduces the amount of visual inspections that have to be performed on the cows and increases accuracy of identification. Moreover, it allows animals that are sick to be treated properly and removed from those that are not sick in order to prevent the spread of the sickness, and it allows an informed decision regarding those that are healthy enough to continue without inoculation. This results in early intervention for animals that actually need antibiotics or other treatments and also informed management of the overall livestock based on objective, newly developed standards and reduced inoculations. This should provide higher quality animals, fewer herd losses, increased feedlot profitability, and potential cost savings, as well as reduce the environmental footprint of large feedlot operation.

Certain features include providing livestock management systems and processes that facilitate and adjust, based on a reliable yet rapid health indicator. A related feature includes allowing feedlots to avoid over-treating a herd and focusing instead on pinpointing animal health.

Providing treated water to well livestock may also improve overall general health benefits. For example, providing treated water to dairy cows may provide enhanced immunity and hydration, which may provide increased milk production. Moreover, treated water may find a variety of uses around a dairy operation. For example, water with a relatively low pH may be used to decontaminate milking machines and cow's udders. This may reduce the spread of infections from cow to cow. Additionally, relatively high pH water, which may be a natural side effect of producing low pH water, may be used as a degreaser. Treated water may also find use in other livestock and agricultural operations.

Providing the ability to search for and find livestock in an automated manner is also advantageous, especially for systems that have limited range. Additionally, being able to obtain data about certain livestock (e.g., by reading a tag and/or obtaining video) during a search is advantageous for determining what is happening with animals that may have health conditions.

Still other implementations relate to products made by the described processes as well as apparatus, systems, and techniques for performing all or part of such processes. Since there are many alternative variations, modifications and substitutions within the scope of the invention, one of ordinary skill in the art should consider the protected scope of the invention from a review of the claims appended hereto as considered in the context of the prior art and the various descriptions of this application.

Many other features will be evident from the remainder of this application in light of a more exhaustive understanding of the numerous difficulties and challenges faced by the prior art, which in turn will be evident to those skilled in the art.

BRIEF DESCRIPTION OF THE DRAWINGS

For a more complete understanding of the present invention and its implementations, and the features thereof, reference is now made to the following descriptions taken in conjunction with the accompanying drawings, in which:

FIG. 5 is a flowchart illustrating selected operations of another example process for livestock management.

FIG. 6 is a flowchart illustrating selected operations of an additional example process for livestock management.

FIG. 16 is a line drawing illustrating another example livestock management system.

Like reference numerals are used for similar elements of various embodiments.

DETAILED DESCRIPTION

Overview

Figure 1:
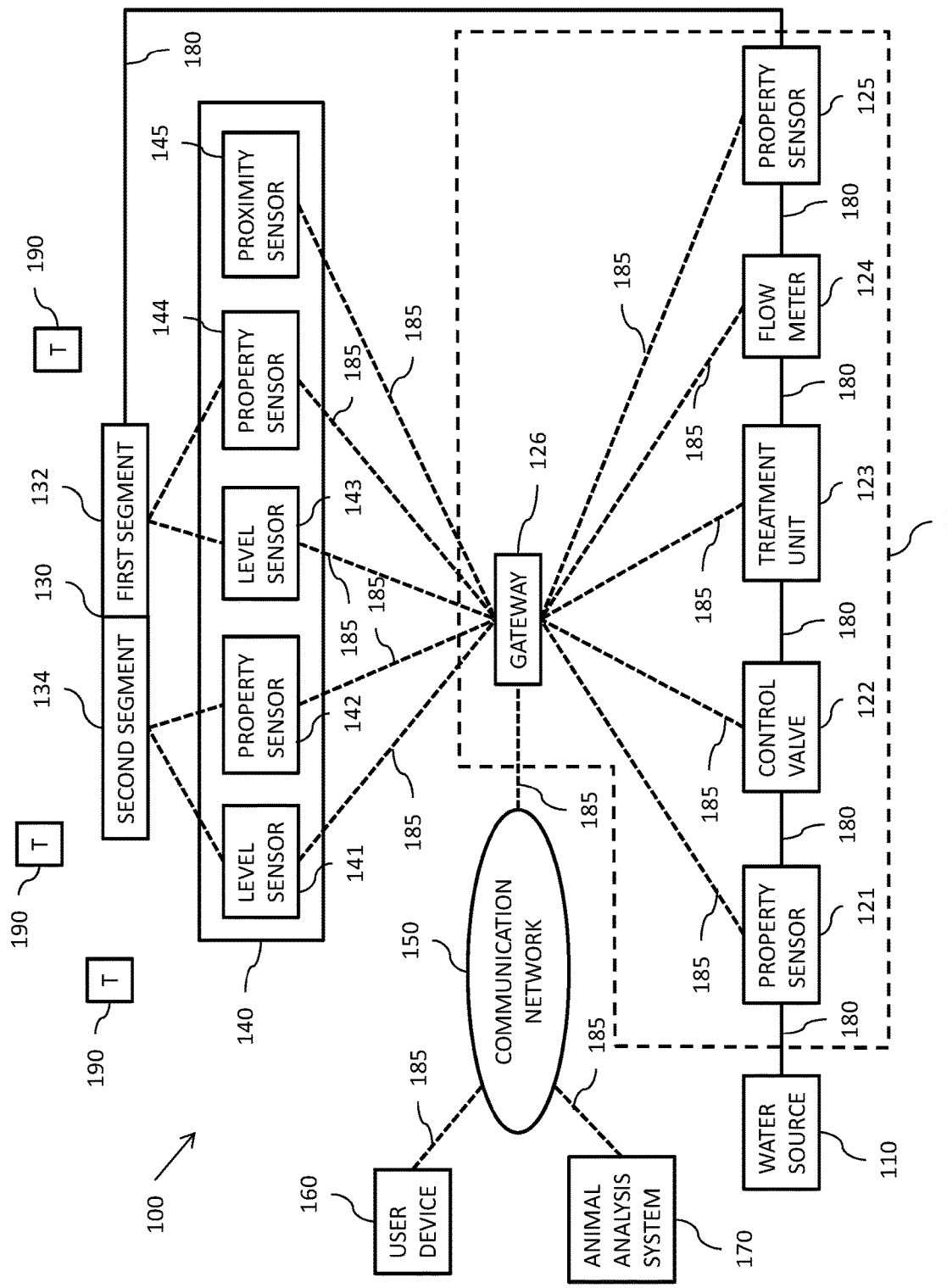
FIG. 1 is block diagram illustrating selected components of an example system for livestock management.

Livestock may be managed by a variety of systems, processes, and techniques in an effort to improve their health and provide a verified food supply chain. In one general implementation, the properties of water may be monitored by automated techniques and treated water may be provided to identified livestock in order to improve their health. For example, sick or potentially sick livestock may be provided with treated water to improve their health. The automated identification techniques may include monitoring the movement, water consumption, and/or feed consumption of the livestock and predicting which ones may have health conditions based on their movements and/or consumption. For instance, movements of cows may be used to predict which cows are sick. Livestock that is sick may be provided with treated water by providing the treated water to a trough when a potentially sick animal approaches.

In particular implementations, a livestock management system may include a trough, a water sensor, a water treatment unit, and a controller. The trough may be adapted to hold water for animal consumption and include an inlet adapted to receive water being injected into the trough. The water sensor may be coupled to the trough and adapted to detect at least one condition of water in the trough. The water treatment unit may be coupled to the trough and adapted to alter at least one property of water being injected into the trough. The controller may be adapted to regulate the injected water based on the detected water condition.

In certain implementations, the sensor may include a first sensor adapted to detect a level of water in the trough and a second sensor adapted to detect at least one property of water in the trough (e.g., oxygen reduction potential, mineral/nutrient presence, or potential hydrogen). The controller may be adapted to regulate the injected water based on the detected water property and the water level.

In particular implementations, a system for livestock management may also include one or more proximity sensors adapted to detect the presence of an animal near the trough. The controller may be adapted to regulate injection of water into the trough in response to the presence of an animal. Additionally, the controller may be adapted to determine the health status of a detected animal and inject treated water into the trough based on the health status of the detected animal.

In some implementations the trough may include a first segment adapted to hold water for animal consumption, and a second segment adapted to hold water for animal consumption. The first segment may include an inlet for receiving water, and a wall may divide the first segment from the second segment, the wall being adapted to allow water from the first segment to flow into the second segment. Typically, the first segment is smaller than the second segment so that when an animal is detected approaching the trough, the properties of the water in the first segment may be rapidly adjusted for the benefit of the animal.

Some implementations may have multiple proximity sensors for the trough. One sensor may, for example, have a longer range (e.g., 10 m) and provide an indication that an animal is on the way to the trough. The indications from this sensor may be used to prepare the water in the trough for animal's arrival. In implementations in which the sensor may detect the animal's identity, the animal's health classification may also be used in prepare the water in the trough. Another sensor may have a short range (e.g., 0.5) and provide an indication that an animal is actually at the trough. The indications from this sensor may be used to determine how often the animal is visiting the water trough as well as how long the animal is dwelling at the water trough. This data may be used in determining the animal's health classification.

Various systems, processes, and techniques described herein may have one or more features. For example, being able to monitor and provide treated water ensures that livestock receives beneficial water. The treated water may increase hydration, raise the pH balance of the cows, and improve their antioxidant capability, helping them to fight off disease without having to use as many antibiotics. This should also provide higher quality animals, fewer herd losses, increased feedlot profitability, and potential cost savings, as well as reduce the environmental footprint of large feedlot operations.

Additionally, being able to provide treated water on demand (e.g., when an animal approaches) allows the treated water to be generated in a judicious manner, resulting in more efficient use of resources and treated water. Furthermore, being able to identify animals allows treated water to be specifically targeted to certain animals, which increases their health, and allows the water to be generated even more efficaciously. Thus, the systems, processes, and techniques may provide an environmentally sound solution as they improve animal health while conserving electricity. While providing treated water for all animals (e.g., healthy, potentially sick, and sick) is possible, it requires quite a bit of electricity for the water treatment process.

Furthermore, being able to track livestock provides the ability to identify animals with health conditions (e.g., sick) in an automated manner. This reduces the amount of visual inspections that have to be performed on the cows and increases accuracy of identification. Also, it allows animals that are sick to be treated properly and removed from those that are not sick in order to prevent the spread of the sickness, and it allows an informed decision regarding those that are healthy enough to continue without inoculation. This results in early intervention for animals that actually need antibiotics or other treatments and also informed management of the overall livestock based on objective standards and reduced inoculations. This should provide higher quality animals, fewer herd losses, increased feedlot profitability, and potential cost savings, as well as reduce the environmental footprint of large feedlot operations.

Certain features include providing livestock management systems and processes that facilitate and adjust, based on a reliable yet rapid health indicator. A related feature includes allowing feedlots to avoid over-treating a herd and focusing instead on overall animal health.

Providing treated water to well livestock may also create general health benefits. For example, providing treated water to dairy cows may provide enhanced immunity and hydration, which may provide increased milk production. Moreover, treated water may find a variety of uses around a dairy operation. For example, water with a relatively low pH may be used to decontaminate milking machines and cow's udders. This may reduce the spread of infections from cow to cow. Additionally, relatively high pH water, which may be a natural side effect of producing low pH water, may be used as a degreaser. Treated water may also find use in other livestock and agricultural operations.

Additionally, providing the ability to search for and find livestock in an automated manner (e.g., via unmanned aerial vehicle) is also advantageous, especially for systems that have limited range. Additionally, being able to obtain data about certain livestock (e.g., by reading a tag and/or obtaining video) during a search is advantageous for determining what is happening with animals that may have health conditions.

Still other implementations relate to products made by the described processes as well as apparatus, systems, and techniques for performing all or part of such processes. Since there are many alternative variations, modifications and substitutions within the scope of the invention, one of ordinary skill in the art should consider the protected scope of the invention from a review of the claims appended hereto as considered in the context of the prior art and the various descriptions of this application.

While the inventive concepts are much more basic than any particular implementation, one skilled in the art can gather a partial appreciation for some of the possible benefits of the broader concepts and possible interplay between various elements of the concepts in the course of considering example implementations, some of which are described in detail below.

The systems, processes, and techniques depicted herein allow for efficient and effective herd management that draws on reliable yet efficient predictive assessment automatically coupled with corresponding treatment of the herd, together with related measures for sorting and data management to achieve comprehensive livestock management. The result yields multiple applications in the feedlot industry, as well as in the dairy, ranching, and packing industries, and in portable systems for use in veterinary applications. As will be evident, some aspects of the invention can even be appreciated in fowl or human or other mono-gastric populations. Occasional paragraph or section headings have been used for ease of reference, but such headings generally should not be read as affecting the meaning of the descriptions included in those paragraphs and sections.

Example Livestock Management System

FIG. 1 illustrates selected components of an example livestock management system 100. Among other things, system 100 includes a water source 110, a control system 120, a water trough 130, and a sensor array 140. In general, sensor array 140 monitors the properties of water in water trough 130, and conveys signals representing the properties to control system 120. Control system 120 analyzes the properties and determines whether to supply water from water source 110—for example, after it has been treated by control system 120 to alter its properties.

Water source 110 may generally be any potable water supply. For example, water source 110 may be a municipal water supply, a ground well, or a storage tank. Water source 110 is coupled to control system 120 by one of conduits 180, which may be a pipe, a channel, a duct, or any other appropriate device for conveying liquid.

Control system 120 includes a property sensor 121, a control valve 122, a water treatment unit 123, a flow meter 124, a property sensor 125, and a gateway 126. Property sensor 121, control valve 122, water treatment unit 123, flow meter 124, and property sensor 125 are fluidly coupled to each other by conduits 180. Property sensor 121, control valve 122, water treatment unit 123, flow meter 124, and property sensor 125 are communicatively coupled to gateway 126 through communication channels 185, which may be wireline (e.g., RS-232, RS-485, USB, Ethernet, etc.) or wireless (e.g., Bluetooth, Wi-Fi, ZigBee, etc.) channels. Communication channels 185 allow information (e.g., sensor readings and commands) to be sent between property sensor 121, control valve 122, water treatment unit 123, flow meter 124, property sensor 125, and gateway 126.

Property sensor 121 is coupled to conduit 180 from water source 120 and is adapted to detect one or more properties (e.g., potential hydrogen (pH), oxygen reduction potential (ORP), temperature, salinity, chlorine content, etc.) of the water from water source 110. Property sensor 121 may, for example, be a probe-type water property sensor. Such sensors are available from a number of companies, such as Sensorex of Garden Grove, CA (USA). An example ORP sensor is the S272CD-ORP from Sensorex. An example pH sensor is the S272CDTC from Sensorex. The detected properties may be sent to gateway 126 over a communication channel 185. Although shown as being in-line with conduit 180 from water source 120, property sensor 121 may be located elsewhere (e.g., on the periphery of a conduit 180).

Control valve 122 is also coupled to conduit 180 from property sensor 121 and is adapted to control the flow of water from the water source. Control valve 122 may, for example, be a ball valve, a butterfly valve, or a gate valve and may have an actuator for adjusting the position of the valve in response to a drive signal. Control valve 122 may be driven by a signal from gateway 126 or may receive commands from gateway 126 and develop its own drive signal.

Water treatment unit 123 is coupled to control valve 122 through a conduit 180 and is adapted to process potable water to have a relatively low (i.e., negative) oxidation reduction potential (ORP) and/or a relatively high pH (i.e., above 7.0). The ORP of the water from the water treatment system may be less than −200 mV and, in particular implementations, may be less than −400 mV. A negative ORP provides a large number of negatively charged ions that provide antioxidant potential. Antioxidants work by slowing or preventing the damage caused by free radicals, which can lead to, among other things, cell dysfunction. Cows, for example, can have an overload of free radicals due to the stress of being shipped and/or being sick. The pH level of the water from water treatment system 130 may be above 8.0 and, in particular implementations may be above 9.0. This may help to lower the acidity level in the cow, especially if the cow is not in homeostasis. The water may also be ionized (e.g., micro-clustered). In particular implementations, the water molecules have a hexagonal structure, which is more acceptable to plants and animals. This makes the water more bioavailable (e.g., efficient in the uptake of water to the lifeform and at carrying minerals).

In certain implementations, water treatment unit 123 may have multiple modes of operation. The modes may be selected by a user via a user device 160 or at the water treatment unit 123 itself. For example, water treatment unit may have four modes:

| Mode | Description | pH | ORP |
| --- | --- | --- | --- |
| 1 | Off | (Source Water) | (Source Water) |
| 2 | Low | 8.5 | 0--75 |
| 3 | Medium | 9.0 | −75--−150 |
| 4 | High | 9.5 | <−150 |

In particular implementations, water treatment unit 123 may treat potable water by electrolysis. In electrolysis, water is run between metal plates (e.g., titanium or copper) that are being subjected to an electrical charge. Example electrolysis water treatment units are available from Enagic, Co., Ltd. of Nago (Okinawa), Japan.

In certain implementations, water treatment system 123 may produce relatively high pH water and relatively low pH water. The relatively high pH water from water treatment unit 123 may have a pH above 8.0 and, in particular implementations, may have a pH above 9.0. In certain implementations, the water may have a pH between 8.5-9.5. The relatively low pH water from water treatment unit 123 may have a pH below 6.0 and, in particular implementations, may have a pH below 5.0. In certain implementations, the relatively low pH water may have a pH between 4.5-5.5. The low pH water may also be electrolyzed (e.g., have a positive charge). This low pH water may be used in animal containment areas (e.g., pens, stalls, cages, etc.) to kill bacteria and other infectious matter for cleansing the areas and treating the areas for healthier animal food production procedures. Low pH water may, for example, be especially beneficial in dairy, swine, and poultry operations.

Additionally, low pH water (e.g., around 4.5) may be useful for watering plants. Moreover, the water may be mixed with fertilizer to provide increased plant growth. Early experiments have shown that acidic water mixed with fertilizer provides high absorption in plant. This should produce increased crop yields and faster maturity times. This may also allow a reduced use of pesticides. Mixtures of water to fertilizer will vary by geographic region depending on soil condition. In implementations where the water molecules have a hexagonal structure, the water may be even more accepted by plants and more effective at carrying fertilizer.

Flow meter 124 is fluidly coupled to water treatment unit 123 by a conduit 180 and is adapted to determine the amount of water flowing though water treatment unit 123, which provides an indication of the general status of the water treatment unit. Flow meter 124 may, for example, function by vane/piston, differential pressure, turbine, or positive placement techniques. The detected flow rate may be sent over a communication channel 185 to controller 126.

Property sensor 125 is fluidly coupled to flow meter 124 and is adapted to detect one or more properties (e.g., pH, ORP, temperature, salinity, chlorine content, etc.) of the water from water treatment unit 123. The detected properties may be sent to gateway 126 over a communication channel 185, to determine the effectiveness of water treatment unit 123. Although shown as being in-line with conduit 180 from water source 120, property sensor 125 may be located elsewhere (e.g., on the periphery of a conduit 180).

As noted previously, gateway 126 receives data regarding the water in water trough 130 and controls the flow of water thereto. As will be discussed in more detail below, based on the properties of the water and/or the amount of water in the water trough, gateway 126 may command control valve 122 to allow more water to flow to water trough 130 and command water treatment unit 123 to process the water. Gateway 126 may generally be any logic-based unit for automatically controlling a system. For example, gateway 126 may include one or more processors (e.g., microprocessors or microcontrollers) to perform its operations. In certain implementations, gateway 126 may include a radio board for communication, a Linux board to manage operations, and a control board to manage/energize the valve on the trough and read sensors.

Water trough 130 is adapted to hold water for animal consumption. Water trough 130 may, for example, be located in a pen or pasture in which livestock (e.g., bovine, swine, fowl, equine, ovis, etc.) are residing. In the illustrated implementation, water trough 130 includes a first segment 132 and a second segment 134. First segment 132 is fluidly coupled to control system 130 through a conduit 180 to receive water therefrom. As further described below, first segment 132 and second segment 134 are configured such that portions of the water in first segment 132 may flow to second segment 134. Water trough 130 may be made of plastic, metal, or any other appropriate material.

Sensor array 140 is communicatively coupled to control system 120 through communication channels 185. In the illustrated implementations, sensor array 140 includes a water level sensor 141, a water property sensor 142, a water level sensor 143, a water property sensor 144, and a proximity sensor 145. In other implementations, sensor array 140 may include fewer, additional, and/or a different combination of sensors.

Level sensor 141 and property sensor 142 are associated with second segment 134 of water trough 130. Thus, they detect data regarding the water in the second segment. In particular, level sensor 141 detects the level of water in second segment 134 and communicates this to control system 130 over a communication channel 185. Level sensor 141 may, for example, be a float switch, a differential pressure sensor, an ultrasonic sensor, or any other appropriate water level sensor. Property sensor 142 is adapted to detect one or more properties (e.g., pH, ORP, temperature, salinity, chlorine content, etc.) of the water in second segment 134. Property sensor 142 may, for example, be a be a probe-type water property sensor. Such sensors are available from a number of companies, such as Sensorex of Garden Grove, CA (USA). The detected properties may be sent to control system 130 over a communication channel 185.

Level sensor 143 and property sensor 144 are associated with first segment 132. Thus, they detect data regarding of the water in the first segment. In particular, level sensor 143 detects the level of water in first segment 132 and communicates this to control system 130 over a communication channel 185. Level sensor 143 may, for example, be a float switch, a differential pressure sensor, or an ultrasonic sensor. Property sensor 144 is adapted to detect one or more properties (e.g., pH, ORP, temperature, salinity, chlorine content, etc.) of the water in first segment 132. Property sensor 144 may, for example, be a probe-type water property sensor. Such sensors are available from a number of companies, such as Sensorex of Garden Grove, CA (USA). The detected properties may be sent to control system 130 over a communication channel 185.

Proximity sensor 145 is adapted to detect the presence of an animal near water trough 130. In particular implementations, proximity sensor 145 may use near-field communication (NFC), radio-frequency identification (RFID), ultrasonic, or optical techniques to detect the presence of an animal. Proximity sensor 145 may convey the detected presence to controller system 130 over a communication channel 185.

NFC is a set of short-range wireless technologies, typically requiring a separation of 10 cm or less. NFC typically operates at 13.56 MHz on ISO/IEC 18000-3 air interface and at rates ranging from 106 kbit/s to 424 kbit/s. NFC operations usually involve an initiator and a target. The initiator actively generates an RF field that can power a passive target, which allows NFC targets to take very simple form factors, such as unpowered tags, stickers, key fobs, or cards. NFC peer-to-peer communication is possible, provided both devices are powered.

NFC tags may contain data and are typically read-only, but may be writeable. They can be custom-encoded by their manufacturers or use NFC Forum specifications. The tags can securely store data, such as debit and credit card information, loyalty program data, PINs and networking contacts, among other information. The NFC Forum defines four types of tags that provide different communication speeds and capabilities in terms of configurability, memory, security, data retention and write endurance. Tags currently offer between 96 and 4,096 bytes of memory.

NFC communication uses magnetic induction between two loop antennas located within each other's near field, effectively forming an air-core transformer. It operates within the globally available and unlicensed ISM band of 13.56 MHz. Most of the RF energy is concentrated in the allowed ±7 kHz bandwidth range, but the full spectral envelope may be as wide as 1.8 MHz when using ASK modulation. Theoretical working distance with compact standard antennas is up to 20 cm, but the practical working distance is about 10 cm.

The two modes of communication with NFC—passive and active. In passive mode, the initiator device provides a carrier field and the target device answers by modulating the existing field. In this mode, the target device may draw its operating power from the initiator-provided electromagnetic field, thus making the target device a transponder. In active mode, both the initiator and the target device communicate by alternately generating their own fields. A device deactivates its RF field while it is waiting for data. In this mode, both devices typically have power supplies.

In the illustrated implementation, one or more animals may be wearing a tag 190. Tags may be in place on the animals when they arrive at system 100 or placed on them when they arrive. Tags 190 may allow the location of each animal to be determined. For example, based on time of arrival of signals from the tags, the position of an animal may be determined by control system 120 (e.g., by trilateration), or the tags themselves may determine position based on Global Positioning System (GPS) measurements by the tags. The tags may communicate with wireless transceivers in a passive or active manner. In a passive manner, the tags may be energized by signals from wireless transceivers and use this energy to transmit their identifiers, along with any other information (e.g., data about the associated animal or the functioning of the tag), back to the wireless transceivers. In an active manner, the tags may generate their own power (e.g., by chemical reaction) and transmit their information to wireless transceivers (e.g., when requested or on a schedule). The time that either the passive or active signals arrive at wireless transceivers may be used for the position determination. The data that is stored may be transmitted through the wireless transceiver to control system 120.

In particular implementations, tags 190 may use radio-frequency identification (RFID) techniques. RFID chips may store identifiers for an animal and/or information history on the animal. Suitable RFID chips are available from Allflex of Dallas, Texas (USA) and NXP Semiconductors of Eindhoven, North Brabant (Netherlands).

The communication between tags 190 and wireless transceivers may be accomplished by any of a variety of wireless protocols. In particular implementations, ISO 13157 techniques may be used. In other implementations, other protocols (e.g., IEEE 802.11, IEEE 802.15, Bluetooth, etc.) may be used.

In the illustrated implementation, proximity sensor 145, a form of wireless transceiver, may read a tag when it comes near the water trough (e.g., within a few centimeters, within a few meters, or within a few tens of meters). In some implementations, the tag may convey an identifier to the proximity sensor. Using the identifier, control system 120 can determine the identity of the associated animal and its health status.

The tags may also be readable visually (such as a bar code or simply a number or color), as well as wirelessly to facilitate the sorting and management of the herd in the pens. In particular implementations, tags may be color coded based on which population the animal falls into at the time. For example, the animals may be divided into: 1) an asymptomatic group (tagged as green); 2) a subclinical group (tagged as yellow); and 3) a clinical group (tagged as red). The tags could also be associated with pens. For example, a green tag could be used for a first pen, a yellow tag could be for a second pen, and a red tag could be used for a third pen. Later, when a handler or veterinarian reassesses an animal, the colored tag would be available as an accessory marker to be used on the animal where visual tracking and sorting is needed. This could also be used in selected fields by a rancher or a dairy farmer as a visual ID on the animal when utilizing the device as an everyday health tool.

A system could utilize a first treatment regimen for animals tagged with a green tag, a second treatment regimen for animals tagged with a yellow tag, and a third distinct regimen for animals tagged with a red tag. For instance, green-tagged cows could generally receive no treatment or affordable/minimal treatment such as Biomycin. Yellow-tagged cows could receive a slightly more aggressive treatment such as Baytril, which is only indicated for bovine respiratory disease (BRD) associated with certain microbial species. Red-tagged calves could receive even more aggressive treatment such as the combination of Draxxin together with Banamine, as well as direct oversight by a veterinarian.

The health condition of animals may be determined when they arrive at system 100 (e.g., by taking their temperature during a chute procedure) or by any other appropriate technique (e.g., visual inspection). For example, cows may fall into three populations: 1) an asymptomatic group (temperature below 104 degrees F.), a subclinical group (temperature between 104-105 degrees F.), or a clinical group (temperature above 105 degrees F.), which typically require multiple treatment days.

In certain implementations, sensor array 140 may be coupled to water trough 130. In other implementations, sensor array may be part of water trough 130.

System 100 also includes a user device 160 and an animal analysis system 170, which are coupled to gateway 126 by a communication network 150. The communication network may, for example, include one or more wide area networks (e.g., the Internet) and/or local area networks (e.g., Ethernet). The communication network may be composed of a collection of wireline and wireless networks (e.g., the Internet, a cellular network, and/or a Wi-Fi network).

Communication network 150 is able to convey messages (e.g., data and instructions) between gateway 126 and user device 160. For example, using communication network 150, gateway 126 may send an alert to the user device. The alert may, for example, be about the operations of system 100 (e.g., the status of control system 120 or the water in water trough 130, or the status of water treatment unit 123). The user device may also be able to log in to gateway 126 (e.g., by establishing a client-server relationship) to retrieve data regarding the operation of system 100 and/or particular animals. For example, gateway 126 may estimate how much water a particular animal has drunk over a certain period (e.g., one day) and use this to determine whether there is a potential problem with the animal. For instance, if proximity sensor can read an identifier for an animal, gateway 126 can determine how often the animal is coming to the water trough. Additionally, using the level sensors, gateway 126 can determine how much water an animal consumes each time it comes to the water trough. If the number of visits and/or consumption is out of line for the animal or the population using the water trough, gateway 126 may generate an alert for the animal. User device 160 may be a personal computer, a laptop computer, a smartphone, a tablet, or any other type of processor-driven device.

Communication network 150 is also able to convey messages between gateway 126 and animal analysis system 170. For example, using communication network 150, gateway 126 may send data regarding system 100 and/or an animal be managed by system 100. The data may, for example, be about the operations of system 100 (e.g., the status of control system 120 or the water in water trough 130). As another example, gateway 126 may estimate how much water a particular animal has drunk over a certain period (e.g., one day) and convey this to animal analysis system, which may determine whether there is a potential problem with the animal. For instance, if proximity sensor 145 can read an identifier for an animal, gateway 126 can determine how often an animal is coming to the water trough. Additionally, using level sensors, gateway 126 can determine how much water an animal consumes each time it comes to the water trough. If the number of visits and/or consumption is out of line for the animal or the population using the water trough, animal analysis system 170 may determine that there is a potential problem with this animal. Animal analysis system 170 could then generate an alert for user device 160 and instruct gateway 126 to place the animal in a special classification. Representations of the animals may be displayed on the user device, using web application logic, according to their health status (e.g., green for healthy, yellow for potentially sick, and red for sick). The animal analysis system 170 may also be able to log in to gateway 126 (e.g., by establishing a client-server relationship) to retrieve data regarding the operation of system 100 and/or particular animals. Animal analysis system 170 may, for example, be one or more servers.

The gateway may have its own database as well as the animal analysis system having a database. Thus, both the gateway and the animal analysis may keep an event history for each tag/animal. From this data tracking, either or both of the animal analysis system and the gateway can both determine when an animal needs attention so that the caretaker (e.g., owner, superintendent, or veterinarian) can be alerted.

In certain implementations, if a caretaker while viewing their animals requests via their application to identify the animals needing attention, the gateway may issue commands to specific animals/tags to activate the tag's local signaling device (e.g., LED).

In certain implementations, tags 190 may convey position data regarding the associated animals to animal analysis system 170. For example, the tags may determine and store the location of the animals (e.g., by GPS measurements) and pass this to animal analysis system 170. The animal analysis system may, for instance, analyze the overall movement of an animal over a period of time (e.g., a day). For example, the distance that the animal traveled during the day may be analyzed. The distance could be analyzed by itself (e.g., against a threshold) to determine whether the cow is behaving abnormally or in comparison to other cows in the same pen, in some type of statistical variance (e.g., an analysis of variance analysis).

For animals that are behaving abnormally, the animal analysis system could analyze the location history for the animals. A variety of factors may affect the movement of cows over the course of a day (e.g., heat, cold, rain, etc.). Thus, just because an animal does not move much during a day does not mean it is ill. However, over the course of several days, this may provide a good indication. Moreover, if the animal's movement is well outside the norm for other animals (e.g., outside three standard deviations), an indication may be provided.

The animal analysis system may determine the health status for animals that are behaving abnormally. For example, if the water consumption and/or movement of the animal is below a certain threshold (e.g., an animal has consumed less than a certain amount of water and moved less than a certain distance for more than two days in a row), it indicates that the animal is potentially unhealthy. If an animal is extremely outside a threshold, it almost certainly indicates that the animal is sick, and at least potentially unhealthy. The health status of animals may be divided into a variety of classifications.

The animal analysis system may determine whether any animals have had a change in their health status. For example, when a cow arrives at system 100, it may be classified as healthy. However, if it is now classified as potentially sick or sick, the health status would have changed. If the health status of one or more animals has changed, the animal analysis system may generate an alert for those animals. The alert may, for example, be a message delivered to a user device (e.g., by e-mail) or a posting to a web-site.

In certain implementations, the animal analysis system may designate certain animals or groups of animals for receiving treated water. For example, potentially unhealthy or sick animals may be designated. As another example, female cows that have recently been bred may be provided with treated water (e.g., negative ORP and/or high pH). This may have the effect of increasing the immune system. The water may be provided to an animal individually or to the animal as part of a larger group.

In certain modes of operation, gateway 126 monitors the level and properties of the water in first segment 132 and second segment 134 based on data received from sensor array 140. If gateway 126 determines that the water level in first segment 132 or second segment 134 is low, it may command control valve 122 to an open position (e.g., 25%, 50%, 75%, or 100%). This will allow water to flow to water treatment unit 123, which will process the water and send it to flow meter 124. Water treatment unit 123 may be in a ready state or have to be activated. After passing through flow meter 124, the treated water will be injected into first segment 132. If the water level in first segment 132 is low, the water will fill first segment 132 until gateway 126 determines that the water level in the first segment is acceptable, based on a reading from level sensor 143. The controller will then command control valve 122 to close, which will shut off water to water treatment unit 123 and, hence, water trough 130. If the water in second segment 134 is low, then the treated water will fill first segment 132 first and then begin filling second segment 134. Once gateway 126 determines that the water level in the second segment is acceptable, the controller will command control valve 122 to close, shutting off water to water trough 130.

Gateway 126 may also use the properties of the water in first segment 132 and second segment 134 to control the water flow thereto. If gateway 126 determines that a property of the water (e.g., ORP or pH) in first segment 132 is inappropriate (e.g., high or low), the controller may command control valve 122 to an open position. This will allow water to flow to water treatment unit 123, which will process the water in the appropriate manner and send it to flow meter 124. After passing through flow meter 124, the treated water will be injected into first segment 132. If the water property in first segment 132 is inappropriate, the water will fill first segment 132 until gateway 126 determines that the water properties in the first segment are acceptable. In particular implementations, water is injected into the first segment from near the bottom. This should cause the newly treated water to fill first segment and push the existing water towards the second segment. Once the water properties in first segment are appropriate, the controller will command control valve 122 to close, which will shut off water to water trough 130. If the water properties in second segment 134 are inappropriate, then the newly treated water will fill first segment 132 and then begin filling second segment 134. Once gateway 126 determines that the water properties in the second segment are appropriate, the controller will command control valve 122 to close, shutting off water to water trough 130.

In certain implementations, gateway 126 may maintain the water properties in the first segment and the second segment at different levels. For example, second segment may be the larger of the segments and be kept at a less preferred level (e.g., −200 mV ORP). This will allow general watering of animals, especially when they arrive at water trough 130 in large groups. The smaller first segment may be kept at a more preferred level (e.g., −400 mV ORP). This water is believed to be preferred by animals, and, hence, should be consumed in larger amounts even though it may occupy less volume in water trough 130.

Gateway 126 may also monitor the properties of water from water source 110 through property sensor 121. For example, gateway 126 may monitor pH and ORP. By monitoring the properties of the water from the water source, gateway 126 may determine whether and how to adjust water treatment unit 123. For example, if gateway 126 determines that the water from water source 110 has a high ORP or low pH, the gateway 126 may command the water treatment unit into a different mode of operation (e.g., higher power). However, if gateway 126 determines that the water from water source 110 has a low ORP or a high pH, the controller may command the water treatment unit into another mode of operation (e.g., lower power).

Gateway 126 may also monitor the status of water treatment unit 123. For example, by monitoring flow meter 124, controller 123 may determine when it is time to change the filters and/or plates in the water treatment unit. Additionally, by monitoring the properties of the treated water with property sensor 125, the controller may determine whether water treatment unit 123 is functioning properly. For instance, if the water treatment unit is not altering the properties of the water from water source 110 to the expected degree, it may indicate a problem with water treatment unit 123.

Gateway 126 may also control the flow of water to water trough 130 based on the presence of an animal. As noted above, proximity sensor 145 is adapted to determine when an animal is near the water trough, which may be used as a proxy for an animal desiring to drink water. When an animal is near the water trough, gateway 126 may determine whether the water in the first segment is acceptable. If the water is not acceptable, the controller may command that a small ratio of the water volume in first segment 132 be injected into the first segment. Research has shown, for example, that small ratios (e.g., 10-25%) of negative ORP water can drastically change the properties of other water. Thus, by injecting a small portion of treated water, the water in the segment can be made acceptable for the animal.

Gateway 126 may also determine the health status of the animal before determining whether to inject water. In particular implementations, gateway 126 may receive data (e.g., from animal analysis system 170) regarding which animals are potentially unhealthy. This data may, for example, be stored in a table in a database and indexed by animal identifier. When an animal is detected by proximity sensor 145, the proximity sensor may read an identifier for the animal (e.g., from a code in an RFID chip or an optical code on a tag) and convey this to gateway 126. Gateway 126 may then check the identifier against the data and determine whether the animal is potentially unhealthy. If there is no indication that the animal may be unhealthy, the controller may take no action regarding the water in the trough. If the animal is potentially unhealthy, however, the controller may command that treated water be injected into the first segment of the trough. This should rapidly adjust the properties of the water to even more beneficial levels (e.g., from −200 mV to −400 mV). In particular implementations, the ORP of the water may go as low as −900 mV, or even −1,100 mV, especially when the treated water is first injected, although it typically does not stay there for long periods.

System 100 has a variety of features. For example, the treated water may raise the pH balance of the animals and improve their antioxidant capability, helping them to fight off disease. This may result in decreased need for costly antibiotics and other pharmakinetics used in animal production and management, which will also reduce the toxic runoff (e.g., through urine) of animal byproducts by reducing drug use and overload and reduce the environmental impact of animal operations.

Moreover, by being able control the water for animals, treated water may be provided to one or more animals in an efficient manner. The beneficial properties of treated water subside after a period of time (e.g., 1-6 days). Thus, the water in the water trough must be rejuvenated from time to time with newly treated water. And although only a fraction of the total water amount must be injected to achieve beneficial results, the treated water is considerably more expensive than just standard water. Thus, being able to inject the treated water in an intelligent manner provides appropriate water in a cost effective manner. This should provide higher quality animals, fewer herd losses, increased feedlot profitability, and potential cost savings, as well as reduce the environmental footprint of large feedlot operations Additionally, being able to detect the presence of animals allows the treated water to be provided when it is needed. For example, if no animal approaches the water trough for an extended period of time, the water does not have to be maintained at its highest levels. But when an animal approaches, the water may be quickly rejuvenated. Additionally, being able to detect the presence of animals also allows potentially unhealthy animals to receive highly preferred water.

System 100 also provides insight into the behavior of animals, especially those that are potentially unhealthy. By detecting the presence of animals and determining their identity, system 100 provides data on how often animals are consuming water and, in certain implementations, how much they are consuming. This may provide insight into the overall health of an animal. Moreover, it may provide early intervention for animals that actually need antibiotics or other treatments and also informed management of the overall herd based on objective standards and reduced inoculations.

Although FIG. 1 illustrates one implementation of a system of livestock management, other systems for livestock management may include fewer, additional, and/or a different arrangement of components. For example, a system may include a tank for storing water from water treatment unit 123. The tank may, for example, be placed between water treatment system 120 and water trough 130. With the tank, if there is ever demand for water that is beyond what water treatment system 120 can provide (e.g., when a large number of animals are let into a pen at once), the treated water may still be provided. The treated water may be stored for a period of time (e.g., 1-6 days) before losing its beneficial properties. As another example, a system may include one or more pumps to move water between components. As a further example, control valve 122 may be part of water treatment unit 123. Additionally, sensors 141-145 may not be part of a sensor array. That is, they could be individual sensors. Moreover, control system 130 could be located in a portable water system, which could be external to a pen, or part of water trough 130.

As another example, a system could include multiple proximity sensors. A first proximity sensor could detect an animal at a distance from the trough (e.g., 10 am) that would allow the system time to inject the treated water into the trough. A second proximity sensor (e.g., with a range of 0.2 m-0.5 m) could then detect that the animal actually arrived at the trough.

System 100 may operate without many of the illustrated elements. For example, a system may not include property sensors 121, 125 and flow meter 124. As another example, a system may not include property sensor 142, level sensor 143, and/or proximity sensor 145. Moreover, water trough 130 may only have one segment. A system may also not have user device 160 and/or animal analysis system 170.

Although control system 120 is shown as a unit, in other implementations, one or more operations of control system 120 may be distributed. For example, gateway 126 may be located with sensor array 140. Additionally, various components of system 120 may be part of another component (e.g., property sensor 121, control valve 122, and flow mater 124) may be part of water treatment unit 123.

In certain implementations, system 100 may include a filter that is coupled to water source 110. The filter may be adapted to purify the potable water. For example, the filter may extract particles (e.g., heavy metals, fluoride, pesticides, calcium, chloramine, chlorine, nitrates, etc.) and/or gasses (e.g., sulfur) from the potable water. The filter may, for example, be a cartridge-type filter. In particular implementations, an insert of another filter may release (e.g., over time) certain minerals (e.g., calcium, potassium, sodium, and/or magnesium) into the filtered water, with the possibility of more targeted release of mineral/nutrient supplementation to at risk animals.

Although system 100 has been discussed primarily with respect to cattle, various aspects of system 100 may also be useful for other types of livestock. For example, producing treated water may be useful for pigs, sheep, goats, chickens, horses, or any other appropriate type of livestock.

Additionally, although system 100 has been discussed in the context of a feedlot, various aspect of system 100 may be used in other settings. For example, the animal location tracking and health prediction may be useful in a field. Furthermore, treated water (e.g., negative ORP) may be provided directly to a series of animals without regard to health. This may, for example, be useful in a poultry operation, where the treated water is provided directly to each animal (e.g., through water feeders). Additionally, treated water may be provided to well dairy cows soon after they are milked. Thus, tracking of animals is not required to provide benefits.

Figure 2:
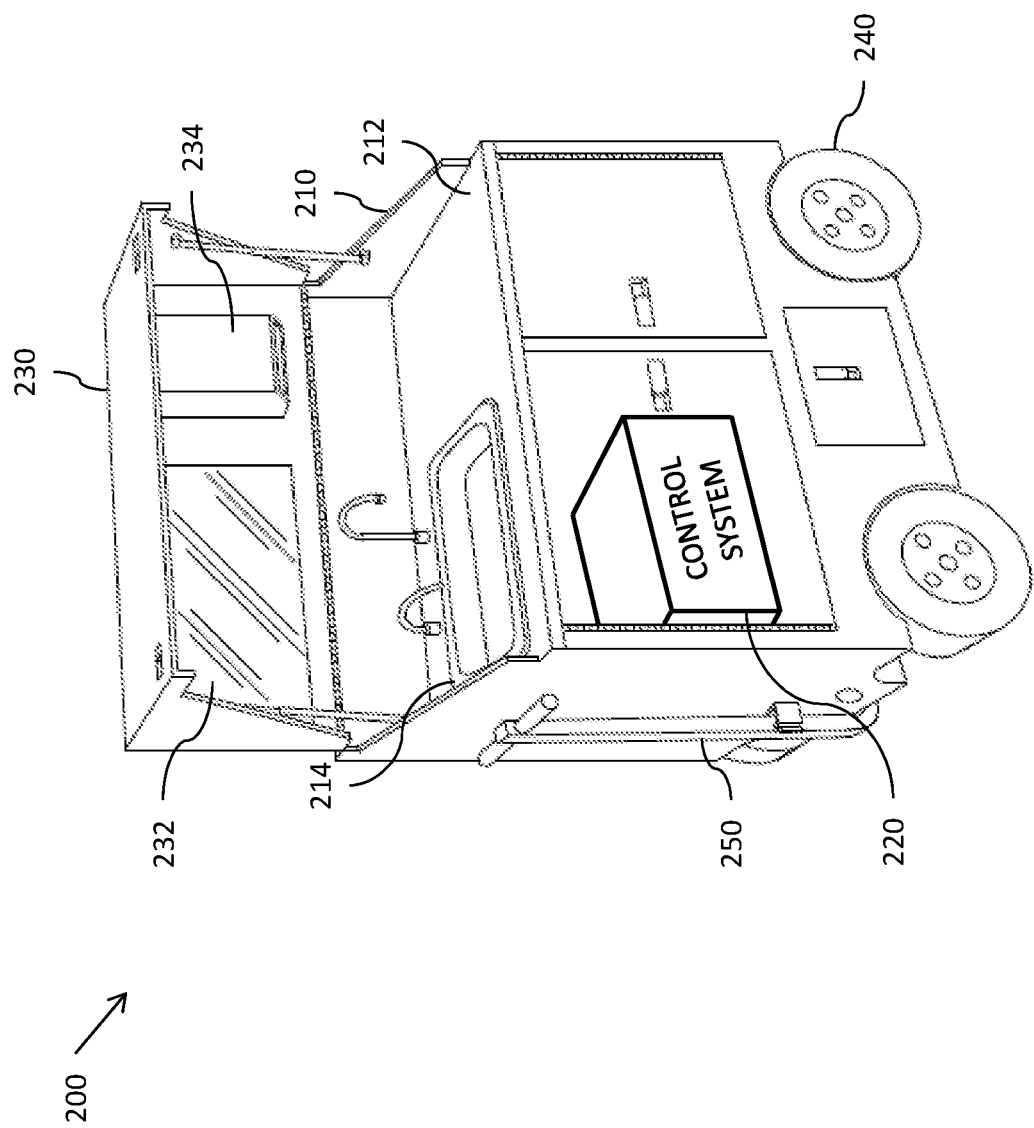
FIG. 2 is a line drawings illustrating selected components of an example livestock management system.

FIG. 2 illustrates selected components of an example livestock management system 200. Among other things, system 200 includes a housing 210 and a water control system 220.

Housing 210 is adapted to support and protect water control system 220. Housing 220 may be made of metal, plastic, or any other appropriate material Water control system 220 is adapted to monitor and control water flow to a water trough. Water control system may, for example, include one or more of a water property sensor, a control valve, a water treatment unit, and a flow meter. These components may be fluidly coupled to each other by conduits. The water control system may also include a controller. The water property sensor, the control valve, the water treatment unit, and the flow meter may be communicatively coupled to the controller through communication channels, which may be a wireline or wireless channels, to allow information (e.g., sensor readings and commands) to be sent between the property sensor, the control valve, the water treatment unit, and the flow meter and the controller. In particular implementations, water control system may be similar to control system 120 in system 100.

System 200 also includes a lid 230, wheels 240, and a handle 250. Lid 230 is hinged to body 210 and encloses a top surface 212 thereof when closed and exposes top surface 212 when opened (as illustrated). Mounted on top surface 212 is a sink 214. Sink 214 is fluidly coupled to control system 220 to receive water treated by the control system. In particular implementations, the water is acidic (e.g., with a pH below 7.0). Mounted to the inside of lid 230 is a mirror and a towel dispenser 234. Wheels 240 are rotatably mounted to the bottom of body 210 and allow system 200 to be easily moved. Handle 250 is also rotatably mounted to body 210 and allows system 200 to be pulled easily.

In operation, control system 220 may monitor the level and properties of water in one or more segments of a water trough (not shown) based on data received from one or more sensors (not shown). If control system 220 determines that the water level in a segment is low, the control system may command that treated water be injected into the segment (e.g., by commanding a control valve to an open position, which allows water to flow to a water treatment unit and, subsequently, to the water trough.) At the water trough, the treated water may be injected into the trough or a segment thereof. If the water level in the segment is low, the water will fill the segment until the controller determines that the water level in the segment is acceptable. The control system will then command the treated water to stop being injected into the segment (e.g., by commanding a control valve to close). If the water in a second segment is low, then the treated water may fill the first segment and then begin filling the second segment. Once the control system determines that the water level in the second segment is acceptable, the control system may command that the treated stop being injected into the first segment (e.g., by commanding a control valve to close).

Control system 220 may also use the properties of the water in one or more segments to control the water flow thereto. If the control system determines that a property of the water (e.g., ORP or pH) in a first segment is inappropriate (e.g., high or low), the control system may command that treated water be injected into the first segment (e.g., by commanding a control valve to an open position, which will allow water to flow to a water treatment unit for processing the water and conveyance to the water trough). If the water property in a first segment is inappropriate, the water will fill the first segment until the control system determines that the water properties in the first segment are acceptable. In particular implementations, water is injected into the first segment near the bottom. This should cause the newly treated water to fill first segment and push the existing water towards a second segment, if any. Once the water properties in the first segment are appropriate, the controller will command that the treated water stop being injected into the trough (e.g., by commanding a control valve to close, which will shut off water to the water trough). If the water properties in a second segment are inappropriate, then the newly treated water may fill a first segment and then begin the filling second segment. Once the control system determines that the water properties in the second segment are appropriate, the control system may command that the treated water stop being injected into the first segment.

In certain implementations, the control system may maintain the water properties in a first segment and a second segment at different levels. For example, the second segment may be the larger of the segments and be kept at a less preferred level (e.g., −200 mV). This will allow general watering of animals, especially when they arrive at the water trough in large groups. The smaller first segment may be kept at a more preferred level (e.g., −400 mV). This water is thought to be naturally preferred by animals.

The control system may also monitor the properties of water from a water source (e.g., a public water supply or a well) through a property sensor. For example, the control system may monitor pH and ORP. By monitoring the properties of the water from the water source, the control system may determine whether and how to adjust the water treatment unit. For example, if the control system determines that the water from the water source has a high ORP or a low pH, the control system may command the water treatment unit into a different mode of operation (e.g., higher power). However, if the control system determines that the water from the water source has a low ORP or a high pH, the control system may command the water treatment unit into another mode of operation (e.g., lower power).

The control system may also monitor the status of the water treatment unit. For example, by monitoring a flow meter, the control system may determine when it is time to change the filters and/or plates in the water treatment unit. Additionally, by monitoring the properties of the treated water with a property sensor, the control system may determine whether the water treatment unit is functioning properly. For instance, if the water treatment unit is not altering the properties of the water from the water source to an expected degree (e.g., there is relatively little change in ORP or pH), it may indicate a problem with the water treatment unit.

The control system may also control the flow of water to the water trough based on the presence of an animal. As noted above, a proximity sensor may be adapted to determine when an animal is near the water trough, which may be used as a proxy for an animal desiring to drink water. When an animal is near the water trough, the control system may determine whether the water in the trough in general or a first segment is acceptable. If the water is not acceptable, the control system may command that a small ratio of the water volume be injected into the water trough. Research has shown, for example, that small ratios (e.g., 10-25%) of negative ORP water can drastically change the properties of other water. Thus, by injecting a small portion of treated water, the water in the segment can be made acceptable for the animal.

The control system may also determine the health status of the animal before determining whether to inject water. In particular implementations, the control system may receive data (e.g., from an animal analysis system) regarding which animals are potentially unhealthy. This data may, for example, be stored in a table in a database and indexed by animal identifier. When an animal is detected by the proximity sensor, the proximity sensor may read an identifier for the animal (e.g., from a code in an RFID chip or an optical code on a tag) and convey this to the control system. The control system may then check the identifier against the data and determine whether the animal is potentially unhealthy. If the there is no indication that the animal may be unhealthy, the control system may take no action regarding the water in the trough. If the animal is potentially unhealthy, however, the control system may command that treated water be injected into the water trough (e.g., in general or into a first segment). This should rapidly adjust the properties of the water to even more beneficial levels (e.g., from −200 mV to −400 mV).

Although FIG. 2 illustrates one implementation of a system of livestock management, other systems for livestock management may include fewer, additional, and/or a different arrangement of components. For example, a system may include a tank for storing water from the water treatment unit. The tank may, for example, be placed between the water treatment unit and the water trough. With the tank, if there is ever demand for water that is beyond what the water treatment unit can provide (e.g., when a large number of cows are let into a pen at once), the treated water may still be provided. The treated water may be stored for a period of time (e.g., 1-6 days) before losing its beneficial properties. As another example, a system may include one or more pumps to move water between components.

Figure 2A:
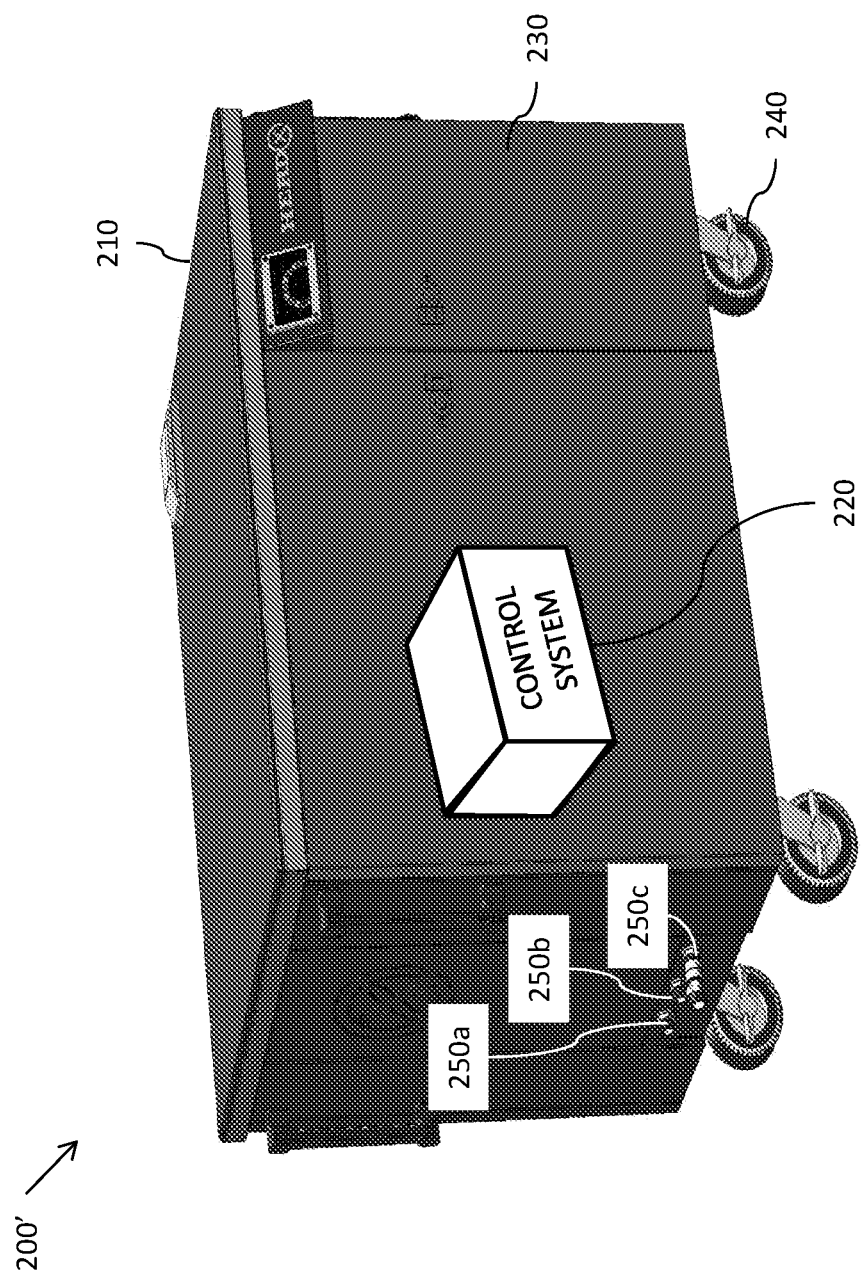
FIG. 2A is a line drawing illustrating selected components of another example livestock management system.

FIG. 2A illustrates selected components of another example livestock management system 200. Among other things, system 200 includes a housing 210 and a water control system 220.

Housing 210 is adapted to support and protect water control system 220. Housing 220 may be made of metal, plastic, or any other appropriate material Water control system 220 is adapted to monitor and control water flow to a water trough. Water control system 220 may, for example, include one or more of a water property sensor, a control valve, a water treatment unit, and a flow meter. These components may be fluidly coupled to each other by conduits. The water control system may also include a gateway. The water property sensor, the control valve, the water treatment unit, and the flow meter may be communicatively coupled to the gateway through communication channels, which may be a wireline or wireless channels, to allow information (e.g., sensor readings and commands) to be sent between the property sensor, the control valve, the water treatment unit, and the flow meter and the controller. In particular implementations, water control system may be similar to control system 120 in system 100.

System 200 also includes doors 230, wheels 240, and water bibs 250. Doors 230 allows access to the interior of housing 210, to service water system 220, for example. Wheels 240 allow system 200 to be easily moved from one location to another. Water bibs 250 allows water to enter and exit housing. For example, water bib 250*c* may allow water to enter housing 210, water bib 250*b* may allow low ORP water to exit housing 210, and water bib 250*a* may allow high ORP water to exit housing. The water to water bib 250*c* may come from a standard water source. The water from water bib 250*a* may travel to a storage tank or irrigation system. The water from big 250*b* may travel to a water trough.

In operation, control system 220 may monitor the level and properties of water in one or more segments of a water trough (not shown) based on data received from one or more sensors (not shown). If control system 220 determines that the water level in a segment is low, the control system may command that treated water be injected into the segment (e.g., by commanding a control valve to an open position, which allows water to flow to a water treatment unit and, subsequently, to the water trough). At the water trough, the treated water may be injected into the trough or a segment thereof. If the water level in the segment is low, the water will fill the segment until the controller determines that the water level in the segment is acceptable. The control system will then command the treated water to stop being injected into the segment (e.g., by commanding a control valve to close). If the water in a second segment is low, then the treated water may fill the first segment and then begin filling the second segment. Once the control system determines that the water level in the second segment is acceptable, the control system may command that the treated stop being injected into the first segment (e.g., by commanding a control valve to close).

Control system 220 may also use the properties of the water in one or more segments to control the water flow thereto. If the control system determines that a property of the water (e.g., ORP or pH) in a first segment is inappropriate (e.g., high or low), the control system may command that treated water be injected into the first segment (e.g., by commanding a control valve to an open position, which will allow water to flow to a water treatment unit for processing the water and conveyance to the water trough). If the water property in a first segment is inappropriate, the water will fill the first segment until the control system determines that the water properties in the first segment are acceptable. In particular implementations, water is injected into the first segment near the bottom. This should cause the newly treated water to fill first segment and push the existing water towards a second segment, if any. Once the water properties in the first segment are appropriate, the controller will command that the treated water stop being injected into the trough (e.g., by commanding a control valve to close, which will shut off water to the water trough). If the water properties in a second segment are inappropriate, then the newly treated water may fill a first segment and then begin the filling second segment. Once the control system determines that the water properties in the second segment are appropriate, the control system may command that the treated water stop being injected into the first segment.

In certain implementations, the control system may maintain the water properties in a first segment and a second segment at different levels. For example, the second segment may be the larger of the segments and be kept at a less preferred level (e.g., −200 mV). This will allow general watering of animals, especially when they arrive at the water trough in large groups. The smaller first segment may be kept at a more preferred level (e.g., −400 mV). This water is thought to be naturally preferred by animals.

The control system may also monitor the properties of water from a water source (e.g., a public water supply or a well) through a property sensor. For example, the control system may monitor pH and ORP. By monitoring the properties of the water from the water source, the control system may determine whether and how to adjust the water treatment unit. For example, if the control system determines that the water from the water source has a high ORP or a low pH, the control system may command the water treatment unit into a different mode of operation (e.g., higher power). However, if the control system determines that the water from the water source has a low ORP or a high pH, the control system may command the water treatment unit into another mode of operation (e.g., lower power).

The control system may also monitor the status of the water treatment unit. For example, by monitoring a flow meter, the control system may determine when it is time to change the filters and/or plates in the water treatment unit. Additionally, by monitoring the properties of the treated water with a property sensor, the control system may determine whether the water treatment unit is functioning properly. For instance, if the water treatment unit is not altering the properties of the water from the water source to an expected degree (e.g., there is relatively little change in ORP or pH), it may indicate a problem with the water treatment unit.

The control system may also control the flow of water to the water trough based on the presence of an animal. As noted above, a proximity sensor may be adapted to determine when an animal is near the water trough, which may be used as a proxy for an animal desiring to drink water. When an animal is near the water trough, the control system may determine whether the water in the trough in general or a first segment is acceptable. If the water is not acceptable, the control system may command that a small ratio of the water volume be injected into the water trough. Research has shown, for example, that small ratios (e.g., 10-25%) of negative ORP water can drastically change the properties of other water. Thus, by injecting a small portion of treated water, the water in the segment can be made acceptable for the animal.

The control system may also determine the health status of the animal before determining whether to inject water. In particular implementations, the control system may receive data (e.g., from an animal analysis system) regarding which animals are potentially unhealthy. This data may, for example, be stored in a table in a database and indexed by animal identifier. When an animal is detected by the proximity sensor, the proximity sensor may read an identifier for the animal (e.g., from a code in an RFID chip or an optical code on a tag) and convey this to the control system. The control system may then check the identifier against the data and determine whether the animal is potentially unhealthy. If the there is no indication that the animal may be unhealthy, the control system may take no action regarding the water in the trough. If the animal is potentially unhealthy, however, the control system may command that treated water be injected into the water trough (e.g., in general or into a first segment). This should rapidly adjust the properties of the water to even more beneficial levels (e.g., from −200 mV to −400 mV).

Although FIG. 2 illustrates one implementation of a system of livestock management, other systems for livestock management may include fewer, additional, and/or a different arrangement of components. For example, a system may include a tank for storing water from the water treatment unit. The tank may, for example, be placed between the water treatment unit and the water trough. With the tank, if there is ever demand for water that is beyond what the water treatment unit can provide (e.g., when a large number of cows are let into a pen at once), the treated water may still be provided. The treated water may be stored for a period of time (e.g., 1-6 days) before losing its beneficial properties. As another example, a system may include one or more pumps to move water between components.

Figure 3A:
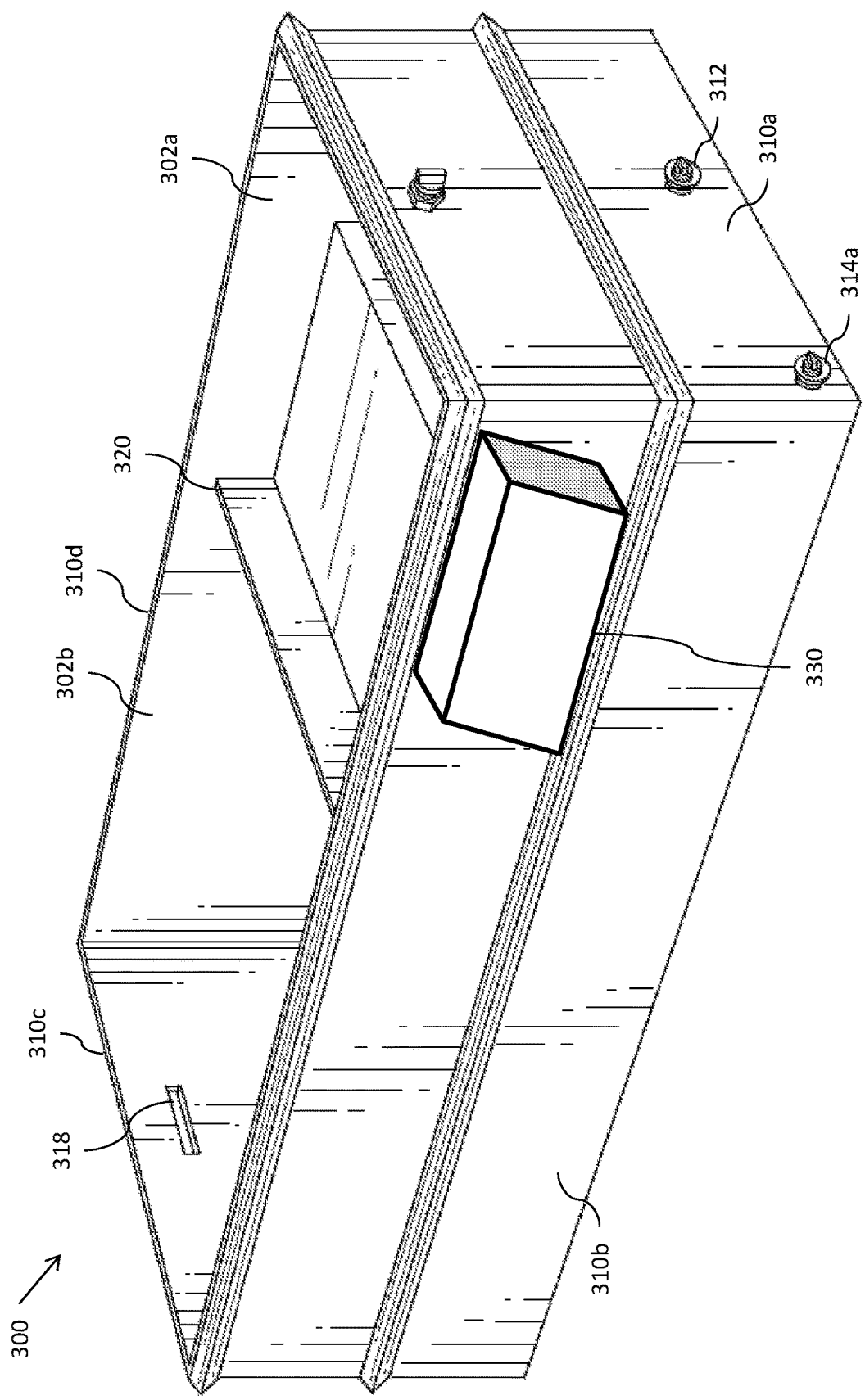
FIGS. 3A-3B are line drawings illustrating an example water trough for livestock management.
Figure 3B:
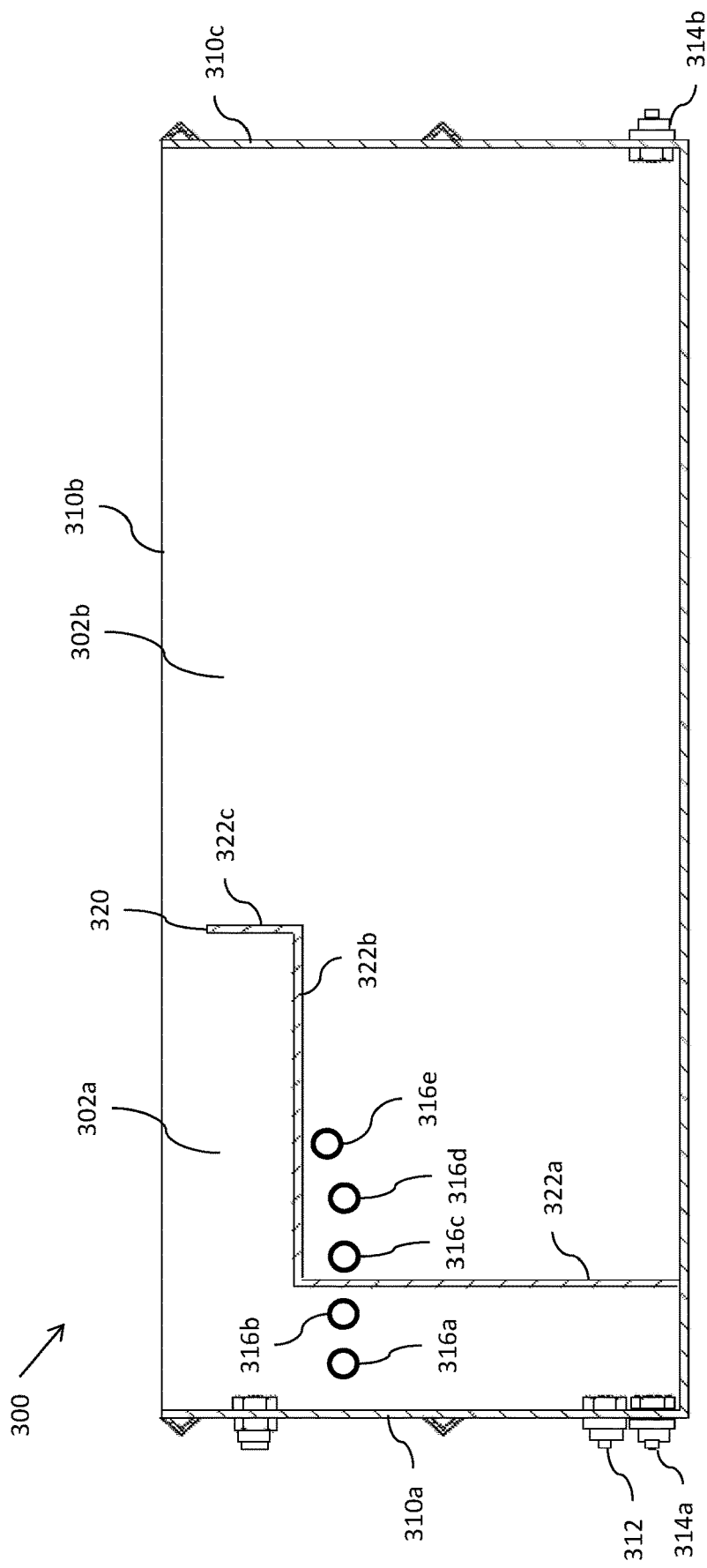

FIGS. 3A-3B illustrate an example water trough 300 for a livestock management system. Among other things, water trough 300 includes outer walls 310 and an inner wall 320, which separates the water trough into two segments 302.

Walls 310, 320 of water trough 300 may be made of plastic, metal, or any other appropriate material. In the illustrated implementation, outer walls 310 form a rectangular shape. Outer walls 310 may form other shapes (e.g., square, oval, circular, etc.) in other implementations.

Outer wall 310*a* includes an inlet 312 and an outlet 314*a*, and outer wall 310*c* includes an outlet 314*b*. Inlet 312 allows water, such as treated water, to be injected into first segment 302*a*. Outlet 314*a* allows first segment 302 to be drained, and outlet 314*b* allows second segment 302*b* to be drained.

Outer wall 310*b* includes a number of sensor ports 316. Sensor ports 316 allow sensors to contact the water in water trough 300. As illustrated, outer wall 310*b* includes two sensor ports 316 for first segment 302*a*, and three sensor ports 316 for second segment 302b. The associated sensors may, for example, sense ORP, pH, and water level.

As mentioned above, inner wall 320 divides water trough 300 into segments 302. In the illustrated implementation, the volume of first segment 302a is substantially smaller than the volume of second segment 302b. This allows the properties of water in first segment 302a to be quickly affected by injected water. Inner wall 320 also functionally separates sensor ports 320a-b from sensor ports 320c-d.

In the illustrated implementation, inner wall 320 has three portions 322 forming an S-shape. Thus, in first segment 302a, inner wall creates a deep section and a shallow section. Inlet 314 is located at the bottom of the deep section so that injected water mixes effectively with the water in first segment 302a. In other implementations, inner wall 320 may have other shapes (e.g., straight).

Upper portion 322c of inner wall 320 does not extend to the top of water trough 300, however. Thus, as water is injected into first segment 302a, the water rises to the top of the inner wall and flows over into second segment 302b. Once the water level sensor in second segment 302b senses the appropriate water level, the water injection may be stopped.

In particular implementations, lower portion 322a may be placed close enough to outer wall 310a so that an animal (e.g., a cow) cannot easily insert its head into the deep section. This helps to keep the animal's mouth away from sensor ports 316a-b. Horizontal portions 322b of inner wall 320, however, provides a large drinking area for animals as compared to the volume of water in first segment 302a, which helps to encourage animals to drink from first segment 302a. The horizontal portion of inner wall 320 also protects sensors in sensor ports 316c-e from animals' mouths.

As discussed above, in certain implementations, water may be injected into water trough 300 in an effort to achieve one or more water properties (e.g., ORP or pH). Thus, at certain points, more water may be injected into the water trough than it can hold. Outer wall 312c includes an outlet 318 through which excess water can flow. Outlet 318 is located below the top of inner wall 320 to prevent water from second segment 302b from flowing back into first segment 302a.

Water trough 300 also includes a housing 330 for protecting the sensors for ports 316. In the illustrated implementation, housing 330 is on outer wall 310b, but it may be located elsewhere in other implementations. The housing may be removable from the water trough to allow access to the sensors.

Water trough 300 has a variety of features. For example, by having two segments, water trough 300 provides away to have high potency water (e.g., in first segment) and low potency water (e.g., in second segment). Additionally, by having a smaller volume for first segment, water trough 300 provides a way to quickly change the properties of water in the first segment. Moreover, by having a horizontally extending inner wall, water trough 300 provides a large consumption area for animals to access the water in the first segment, especially relative to its volume. Additionally, by locating the water level sensor in the second segment under the aperture 318, water trough 300 provides a volume in the second segment (i.e., above the water level sensor and below aperture 318) for water that flows over from the first segment (e.g., due to trying to change the water properties in the first segment or trying to change the water properties in the second segment). Thus, water does not necessarily overflow the water trough (and potentially be wasted) if an adjustment needs to be made to the water in the water trough.

Figure 4:
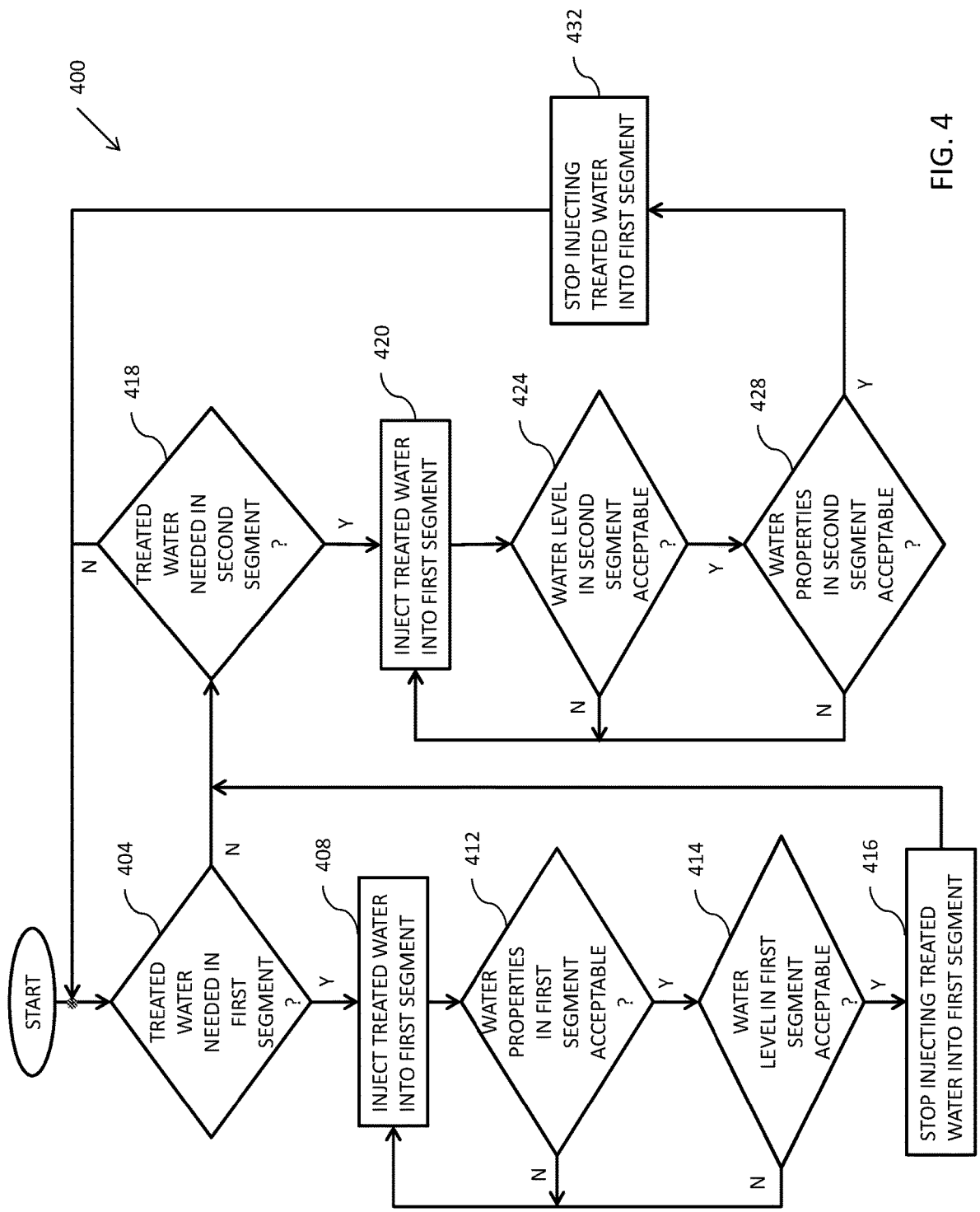
FIG. 4 is a flowchart illustrating selected operations of an example process for livestock management.

FIG. 4 illustrates an example process 400 for livestock management. Process 400 may, for example, be implemented by a system similar to control system 120 in system 100.

Process 400 calls for determining whether treated water is needed in a first segment of a water trough (operation 404). Determining whether treated water is needed in a first segment of a water trough may, for example, be accomplished by analyzing one or more properties of the water in the first segment or the level of water in the first segment. If, for instance, a property is inappropriate (e.g., high ORP), treated water may be needed to adjust the property. Determining whether treated water is needed in a first segment may, for example, be time or event driven. For example, the determination may be made at a regular interval (e.g. every hour, every ten minutes, every minute, or every second) or when an animal approaches.

If treated water is not needed in the first segment, process 400 calls for determining whether treated water is need in a second segment of the water trough (operation 418). Determining whether treated water is needed in a second segment of the water trough may, for example, be accomplished by analyzing the properties of the water in the second segment or the level of water in the second segment. If, for instance, a property is inappropriate (e.g., low pH), treated water may be needed to adjust the property. Determining whether treated water is needed in a second segment may, for example, be time or event driven. For example, the determination may be made at a regular interval (e.g. every hour, every ten minutes, every minute, or every second) or when an animal approaches. If treated water is not needed in the second segment, process 400 calls for again determining if treated water is needed in the first segment (operation 404).

If treated water is needed in the first segment, process 400 calls for injecting treated water into the first segment (operation 408). Injecting treated water into the first segment may, for example, be accomplished by opening a valve that allows potable water to flow to a water treatment system. The water treatment system will treat the water, and the treated water will be conveyed to the first segment. In other implementations, the treated water may be stored in a storage tank and released therefrom. The treated water may have to be pumped in certain implementations.

Process 400 also calls for determining whether the water properties in the first segment are acceptable (operation 412). Determining whether the water properties in the first segment are acceptable may, for example, be accomplished by analyzing readings from a water property sensor (e.g., a pH sensor). If the water properties are not acceptable, process 400 calls for continuing to inject treated water into the first segment (operation 408).

Once the water properties in the first segment are acceptable, process 400 calls for determining whether the water level in the first segment is acceptable (operation 414). Determining whether the water level in the first segment is acceptable may, for example, be accomplished by analyzing readings from a water level sensor (e.g., a float switch or a hydrostatic transducer). If the water level is not acceptable, process 400 calls for continuing to inject treated water into the first segment (operation 408).

Once the water level in the first segment is acceptable, process 400 calls for stopping the injection of water into the first segment (operation 416). Stopping the injection of the water may, for example, be accomplished by closing a valve.

Process 400 then calls for again determining whether treated water is needed in a second segment of the water trough (operation 418). If treated water is needed in a second segment of the trough, process 400 calls for injecting treated water into the first segment (operation 420). Injecting treated water into the first segment may, for example, be accomplished by opening a valve that allows potable water to access a water treatment system. The water treatment system will treat the water, and the treated water will be conveyed to the first segment. In other implementations, the treated water may be stored in a storage tank and released therefrom. Once the first segment is full, the water from the first segment, which is a mixture of the treated water and the water previously in the first segment, may transfer to the second segment.

Process 400 also calls for determining whether the water level in the second segment is acceptable (operation 424). Determining whether the water level in the second segment is acceptable may, for example, be accomplished by analyzing readings from a water level sensor (e.g., an ultrasonic sensor). If the water level is not acceptable, process 400 calls for continuing to inject treated water into the first segment (operation 420).

Once the water level in the second segment is acceptable, process 400 calls for determining whether the water properties in the second segment are acceptable (operation 428). If the water properties in the second segment are not acceptable, process 400 calls for continuing to inject treated water into the first segment (operation 420).

Once the water properties in the second segment are acceptable, process 400 calls for stopping the injection of treated water into the first segment (operation 432). Process 400 then calls for determining whether treated water is needed in the first segment (operation 404).

Although FIG. 4 illustrates an example process for livestock management, other processes for livestock management may include fewer, greater, and/or a different arrangement of operations. For example, a process may not include analyzing properties of the water in the second segment. Thus, the injection of the treated water may be stopped when the water level in the second segment is acceptable. As another example, a process may not include analyzing and injecting water into a second segment (e.g., when a water trough only has one segment). As an additional example, a process may include detecting the proximity of an animal and injecting treated water into the first segment based on the detection or based on the identity of the animal. As a further example, a process may include filling a storage tank.

FIG. 5 illustrates another example process 500 for livestock management. Process 500 may, for example, be implemented by a system similar to control system 120 in system 100 and/or used in conjunction with a process similar to process 400.

Process 500 calls for determining whether an animal is approaching a water trough (operation 504). Determining whether an animal is approaching a water trough may, for example, be accomplished by determining whether an animal is in the vicinity of the water trough. Determining whether an animal is in the vicinity of a water trough may, for example, be accomplished by detecting a tag on the animal (e.g., electrically or optically). Many communication protocols (e.g., Near-field Communication) have very limited ranges (e.g., a few meters). Thus, if an animal's tag (e.g., a target) is in range of a corresponding communication apparatus (e.g., an initiator), an animal near the water trough is likely approaching it. If an animal is not approaching the water trough, process 500 calls for continuing to determine whether an animal is approaching the water trough.

Once an animal is approaching the water trough, process 500 calls for determining whether the animal is potentially unhealthy (operation 508). Determining whether an animal is potentially unhealthy may, for example, be accomplished by determining an identifier associated with a tag and determining whether the identifier is associated with a potentially unhealthy animal. If the animal is not potentially unhealthy, process 500 calls for returning to determine whether an animal is approaching the water trough.

If the animal is potentially unhealthy, process 500 calls for determining whether water in the water tough is acceptable (operation 512). Determining whether the water in the water trough is acceptable may, for example, be accomplished by analyzing readings from a water property sensor (e.g., an ORP or a pH sensor). The reading may be made from a segment of the water trough if the water trough has multiple segments. If the water is acceptable, process 500 calls for returning to determine whether an animal is approaching the water trough (operation 504). If the water is not acceptable, process 500 calls for injecting treated water into the water trough (operation 516). The treated water may, for example, be injected into the water trough until the water is acceptable.

Although FIG. 5 illustrates an example process for livestock management, other processes for livestock management may include fewer, greater, and/or a different arrangement of operations. For example, a process may not include determining whether the animal is potentially unhealthy. Thus, treated water may be injected into the water trough when an animal is approaching the water trough. As another example, a process may include determining how much water an animal drank. For instance, a water level sensor could be monitored to determine how much the water level changed when the animal drank. This could be used to compute a volume based on the geometry of the water trough. In another implementation, a flow meter could be monitored to determine how much water was required to refill the water trough after the animal drank. In certain implementations, the type of water consumed (e.g., potable, less preferred, or preferred) could be determined too. As an additional example, a process could include monitoring the water in the water trough to make sure it achieved the desired properties.

FIG. 6 illustrates another example process 600 for livestock management. Process 600 may, for example, be implemented by a system similar to control system 120 in system 100 and/or used in conjunction with a process similar to process 500.

Process 600 calls for determining whether identifiers for potentially unhealthy animals are available (operation 604). The identifiers could, for example, be sent from an animal analysis system or determined (e.g., by analyzing animal drinking patterns). If identifiers for potentially unhealthy animals are not available, process 600 calls for waiting for identifiers for potentially unhealthy animals to be available.

Once identifiers for potentially unhealthy animals are available, process 600 calls for storing the identifiers (operation 608). The identifiers could, for example, be stored in a database.

Although FIG. 6 illustrates an example process for livestock management, other example processes for livestock management may include fewer, additional, and/or a different arrangement of operations. For example, a process may include storing data regarding animals (e.g., water consumption, trips to water trough, types of water consumed, etc.)

and sending this data to remote computer system (e.g., an animal analysis system). As another example, a process may include recording and sending data regarding the operation of a water system (e.g., properties of water in water trough, status of water treatment unit, amount of water processed, etc.). As an additional example, a process may include receiving commands regarding operation of a control system (e.g., properties for water in trough, processing of water by water treatment unit, etc.) and implementing the commands.

Figure 7:
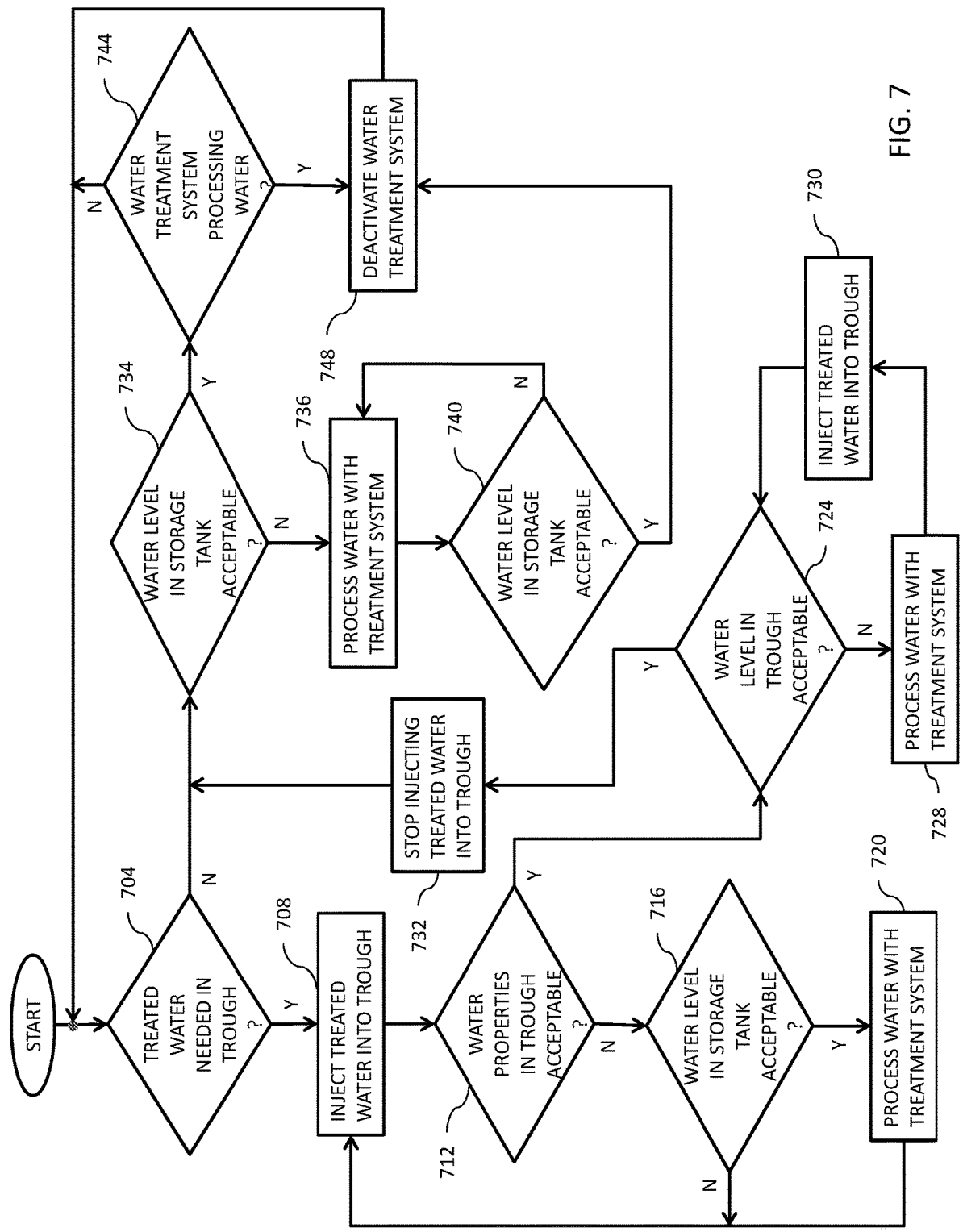
FIG. 7 is a flowchart illustrating selected operations of another example process for livestock management.

FIG. 7 illustrates an additional example process 700 for livestock management. Process 700 may, for example, be implemented by a system similar to control system 120 in system 100.

Process 700 calls for determining whether treated water is needed in a water trough (operation 704). Determining whether treated water is needed in a water trough may, for example, be accomplished by analyzing the properties of the water in the water trough (e.g., ORP) or the level of water in the water trough. If, for instance, a property is inappropriate (e.g., high ORP or low pH), treated water may be needed to adjust the property. Determining whether treated water is needed in a water trough may, for example, be time or event driven. For example, the determination may be made at a regular interval (e.g. every hour, every ten minutes, every minute, or every second) or when an event occurs (e.g., when an animal approaches the water trough).

If treated water is not needed in the water trough, process 700 calls for determining whether the water level in a storage tank is acceptable (operation 734). The storage tank may store treated water for quick injection into the water trough (e.g., when a number of animals approach at one time or when an unhealthy animal approaches). Determining whether the water level in the storage tank is acceptable may, for example, be accomplished by analyzing readings from a sensor. Determining whether the water level in the storage tank is acceptable may, for example, be time or event driven. For example, the determination may be made at a regular interval (e.g. every hour, every ten minutes, every minute, or every second) or an irregular interval.

If the water level in the storage tank is acceptable, process 700 calls for determining if the water treatment system is processing water (operation 744). If the water treatment system is processing water, process 700 calls for deactivating the water treatment system (operation 748). Deactivating the water treatment may, for example, be accomplished by closing a control valve for supply water. If the water treatment system is not running or has been deactivated, process 700 calls for again determining if treated water is needed in the water trough (operation 704).

If treated water is needed in the water trough, process 700 calls for injecting treated water (e.g., low ORP and high pH) into the water trough (operation 708). Injecting treated water into the water trough may, for example, be accomplished by opening a valve and/or activating a pump that allows treated water from the storage tank to flow to the water trough.

Process 700 also calls for determining whether the water properties in the water trough are acceptable (operation 712). Determining whether the water properties in the water trough are acceptable may, for example, be accomplished by analyzing readings from a water property sensor (e.g., a pH sensor).

If the water properties are not acceptable, process 700 calls for determining whether the water level in the storage tank is acceptable (operation 716). In some instances, the water properties of the water trough may be adjusted with small amounts of water (e.g., 10% of the water in the water trough). Thus, not much water may be drawn from the storage tank (e.g., 25%), allowing a water treatment system to remain inactive. If the water level in the storage tank is acceptable (e.g., above 50%), process 700 calls for continuing to inject treated water into the water trough (operation 708). If, however, the water level in the storage tank is not acceptable (e.g., less than 25%), process 700 calls for processing water with the water treatment system (operation 720). The water treatment system thus will begin replenishing the water in storage tank while water is being removed therefrom. Processing water with the water treatment system may include activating the water treatment system and/or supplying water to the water treatment system. Process 700 then calls for continuing to inject treated water into the water trough (operation 708)

Once the water properties in the water trough are acceptable, process 700 calls for determining whether the water level in the water trough is acceptable (operation 724). Determining whether the water level in the water trough is acceptable may, for example, be accomplished by analyzing readings from a water level sensor (e.g., a float switch or an ultrasonic sensor). If the water level in the water trough is not acceptable, process 700 calls for processing water with (e.g., beginning to do so or continuing to do so) the water treatment system (operation 728). Adjusting the properties of water can often be performed with a small volume of water. Thus, it may not be necessary to run the water treatment system if only water properties need to be adjusted. However, filling a water trough often involves a large amount of water. Thus, when the water level in the water trough is low, the water treatment system may be run while filling the water trough. Process 700 also calls for continuing to inject treated water into the water trough (operation 730) and again checking the water level in the water trough (operation 724).

Once the water level in the water trough is acceptable, process 700 calls for stopping the injection of water into the water trough (operation 732). Stopping the injection of the water may, for example, be accomplished by closing a valve and/or deactivating a pump.

Process 700 then calls for determining whether the water level in the storage tank is acceptable (operation 734). If the water level in the storage tank is acceptable, process 700 calls for determining whether the water treatment system is processing water (operation 744) and deactivating it if it is (operation 748). Deactivating the water treatment system may, for example, include closing a valve, stopping a pump, and/or deactivating the water treatment unit. If, however, the water level in the storage tank is not acceptable, process 700 calls for processing water with the water treatment system (operation 736). The water from the water treatment system is stored in the storage tank.

Process 700 also calls for determining whether the water level in the storage tank is acceptable (operation 740). If the water level in the storage tank is not acceptable (e.g., below 75%), process 700 calls for continuing to process water with the water treatment system (operation 736). Once the water level in the storage tank is acceptable, process 700 calls for deactivating the water treatment system (operation 748) and returning to checking whether treated water is needed in the water trough (operation 704).

Although FIG. 7 illustrates an example process for livestock management, other processes for livestock management may include fewer, greater, and/or a different arrangement of operations. For example, a process may include analyzing one or more properties of water in the storage tank and processing water with the water treatment system if the water properties in the storage tank are not appropriate. As another example, a process may include monitoring and altering water properties in multiple segments of a water trough. As a further example, a process may not include determining whether the water level in the storage tank is acceptable. For instance, the water treatment system may be run any time the storage tank has a decrease in water level. As another example, a process may not include a storage tank.

Example Tags

Figure 8:
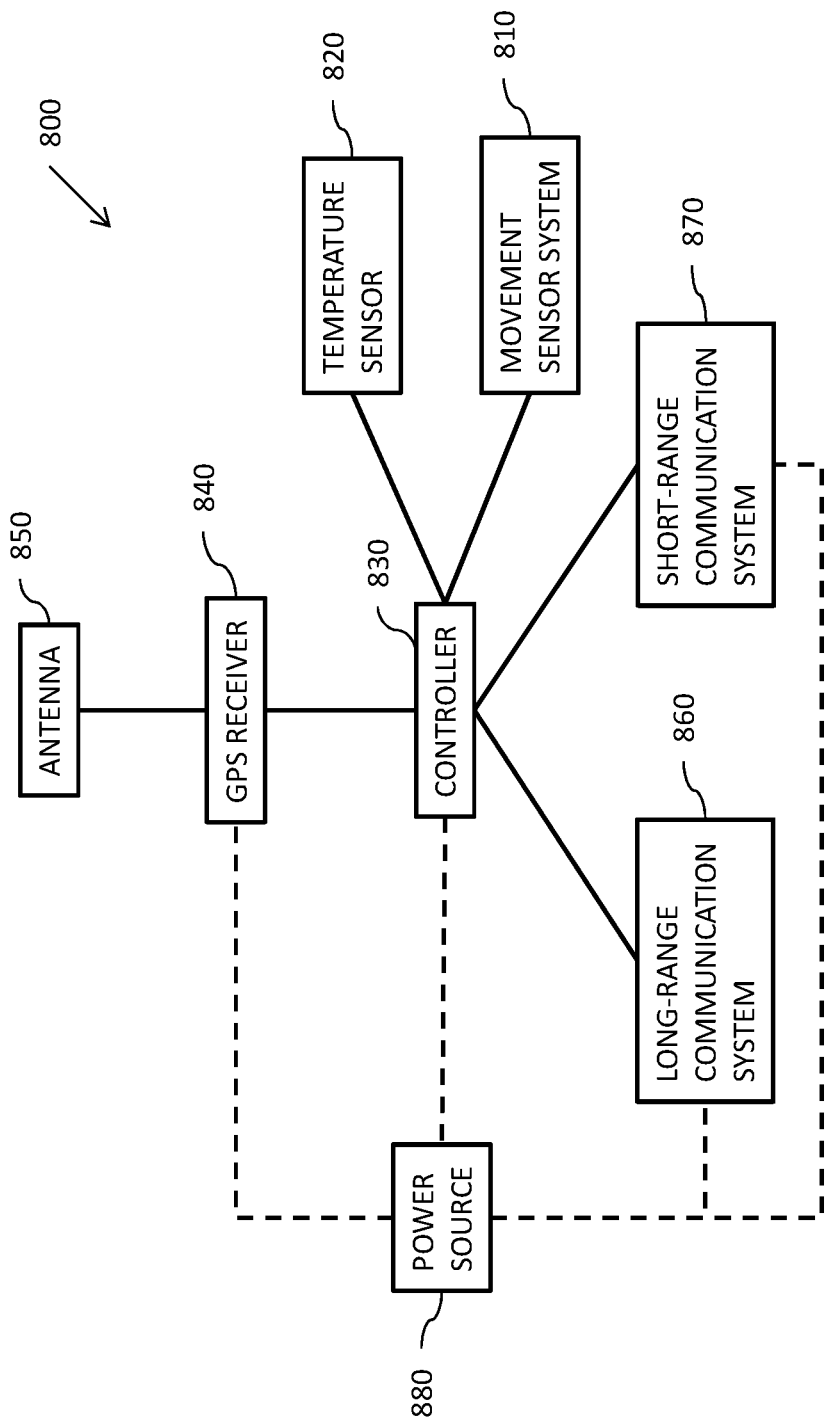
FIG. 8 is a block diagram illustrating selected components of an example animal tag for use in a livestock management system.

FIG. 8 illustrates selected components of an example tag 800 for performing livestock management. Tag 800 may be worn on an animal's ear or on an animal's collar. Tag 800 may, for example, be part of a system similar to system 100. Among other things, tag 800 includes a movement sensor system 810, a temperature sensor 820, a controller 830, a Global Positioning System (GPS) receiver 840, a GPS antenna 850, and a long-range communication system 860.

Movement sensor system 810 is adapted to detect the movements of an animal. Movement sensor system may, for example, include one or more accelerometers. Based on the detected movements, controller 830 may determine whether the animal is potentially unhealthy. For example, healthy animals typically have various movements and movement distances associated with them throughout the day. However, sick animals tend to be lethargic. Thus, by sensing an animal's movements and analyzing them (e.g., compared to previous movements of the animal or to movements of other animals in an area), a determination may be made as to whether an animal is potentially unhealthy.

Temperature sensor 820 is adapted to detect the temperature of the animal. Based on the detected animal temperature, controller 830 may determine whether the animal is potentially unhealthy. For example, healthy cow temperatures are typically between 101 and 102 degrees F. An elevated temperature (e.g., greater than 104 degrees F.) may mean that the animal is in distress. The temperature may be compared to previous temperatures of the animal or temperatures of other animals in an area. In particular implementations, the temperature may be analyzed in combination with the animal's movements to assess whether the animal is potentially unhealthy.

As expressed above, controller 830 is responsible for analyzing data sensed by movement sensor system 820 and temperature sensor 830. Controller 830 is also responsible for analyzing data sensed by GPS receiver 840 and communicating data regarding the animal to a remote system, using long-range communication system 860, for example. Controller 830 may include one or more processors (e.g., microprocessors, microcontrollers, or any other device for manipulating data in logical manner) and memory, which may store instructions and data.

GPS receiver 840 is responsible for determining the geographic position of the animal. GPS receiver 840 receives signals from multiple (e.g., four) satellites through antenna 850 and determines the position through trilateration and/or differential GPS.

Long-range communication system 860 may send and receive data over large distances (e.g., greater than 100 m). In certain implementations, long-range communication system 860 may send data over a cellular communication system (e.g., GSM, CDMA, etc.). The data may be sent in-band or out-of-band.

Tag 800 also includes a short-range communication system 870. Short-range communication system 870 may send and receive data over small distances (e.g., less than 30 m). Short-range communication system 870 may send data using any of a variety of protocols (e.g., Bluetooth, RFID, NFC, etc.).

Tag 800 further includes a power source 880. Power source 880 is adapted to provide power to controller 830, GPS receiver 840, long-range communication system 860, and short-range communication system 870. Power source 880 may operate by chemical (e.g., battery), electromagnetic (e.g., solar), and/or any other appropriate technique.

In certain modes of operation, movement sensor system 810 may sense the movements of the animal and send signals representing the movements to controller 830. Temperature sensor 820 may also sense the temperature of the animal and send signals representing the temperature to controller 830. Controller 830 may analyze the sensed movements and/or the temperature to determine whether the animal is healthy or potentially unhealthy. If the animal is healthy, controller 830 may continue receiving movement data and temperature data and determining whether the animal is healthy or unhealthy. The movement data and the temperature data may also be stored by the controller. This data may be conveyed to a remote system (e.g., an animal analysis system) when requested via communication system 860.

Movement sensor system 810 may, for example, include an accelerometer that can detect animal movements. The accelerometer may, for example, be a three-axis accelerometer, but in some implementations, a two-axis accelerometer may be used. Typically, if an animal, especially a grazing animal, is stationary too long, it is sick. For example, for cows, if they lie down less than 2 hours consecutively, they are typically healthy However, if they lie down 2-4 hours they may be sick, and if they lie down more than 4 consecutive hours, they probably are sick. An accelerometer would typically register little to no acceleration, especially lateral acceleration, while the cow is lying down.

In certain implementations, patterns of movement (e.g., dropping front and then rear) may be stored and looked for to determine when an animal is lying down. Additionally, taking readings while a cow is lying downs (e.g., at night) may provide insight into when a cow is lying down in the future.

As another example, a tag may include a sensor that can determine the height of the tag from the ground. Cows, for example, typically raise and lower their heads may times during the day as they graze and move. However, sick cows typically hang their heads low for extended periods of time. For instance, if a cow hangs its head low less than 3 consecutive hours, they may be considered healthy. However, if a cow hangs it head low between 3-4 hours consecutively, it may be unhealthy, and if it hangs its head low more than 4 hours consecutively, it is probably sick.

To measure head height, an accelerometer may be used to determine that an animal is hanging its head low. By sensing that a cow has dropped its head and then not raised it for a period of time, this determination may be made. In particular implementations, the raising and lowering of the animal's head may be monitored over a period. From this a statistical analysis of the head position could be generated (e.g., a histogram). Once the baseline has been established, trends may be looked for on a day to day basis to detect deviations.

Some implementations may use an ultrasonic or optical sensor (e.g., laser of infrared) to measure the distance of the head from the ground. Using average readings over the course of a day could provide an indication that the cow is hanging its head low. To conserve power, readings may be made periodically. In some implementations, a measurement could be made by a sensor (e.g., ultrasonic) to confirm that the animal's head is hanging low (e.g., if data from the accelerometer indicates this may be occurring).

Due to the variance in tag hanging geometrics and head angles, it may be beneficial to account for non-vertical measurements. Thus, in some implementation, it may be worthwhile to include an accelerometer to determine how far off vertical the tag is at the time of a measurement.

Another type of movement sensor may detect movement of the cows ears. Cows typically move their ears when they ruminate, which they do more of when they are healthy. For example, typically, if a cow ruminates for more than 8 hours per day, they are healthy. However if a cow ruminates for between 6-8 hours a day they may be sick, and if a cow ruminates for less than 6 hours a day, they probably are sick.

To detect ear movement, a multi-axis accelerometer could be used and small, periodic movement (produced by a chewing motion) could be uniquely searched for. As math computations will consume battery, triggers may need to be established to shorten the window of observation. For example, if an animal typically lies down, then that can be a trigger to start the algorithm. Also, if rumination occurs X time after another event (e.g. feeding, watering, laying down, etc.), then timers may be established to start the detection. If there is a known cadence (frequency) for larger versus smaller animals, unique breed patterns, etc., then that can be programmed into the tag firmware and adjusted over time if needed.

The behavior of a group of animals (e.g., movement, lying down, handing head low, rumination, etc.) can be affected by a number of things. For example, weather is a major factor for outdoor animals. Rain, cold, wind, snow, and heat will have an effect on how the animals behave in general. In particular implementations therefore, group averages and deviations may be used to determine whether a cow is potentially sick. For example, if a group has a sudden change in behavior (i.e., is stationary for several consecutive hours), the health metrics may be adjusted to the group average. The sick metrics may also be adjusted to be above/below the average behavior. Deviations away from the average (e.g., 5%) may be used to infer that an animal might be sick, and large deviations away from the average (e.g., 10%) may be used to infer that an animal is sick.

Temperature sensor 820 may, for example, be a thermistor, an analog temperature sensor, or a digital temp sensor. For increased accuracy, these may be placed so that the temperature is measured as close to the ear attach point as possible (near the dart receptacle). A thermistor is a small 2-terminal device, so 2-wires or a small, custom, flex circuit will allow it to be positioned away from the main board to a remote location. The controller will periodically measure the thermistor and apply a non-linear correction to estimate temperature. Digital temperature sensors have the advantage of being a calibrated device with programmable threshold/wake features that would allow the main board to be alerted automatically when a threshold is exceeded.

As temperature sensors are relatively easy to implement, some implementations may use multiple such sensors (e.g., 2-3 of them) around the ear hole in case one portion of the attach tab has separated from the ear (e.g., use highest temperature reading). This could have the additional benefit of detecting loose tags, infections, etc. In particular implementations, a tag/environmental reference temperature might be useful. Thus, some implementations could include another temperature sensor on the main board (below the ear).

To enhance thermal transfer near the ear attach point, the donut section of the tag tab can be lined with thermal transfer material that can accumulate ear/body heat for the thermistor. For example, the thermal transfer material could be Pyrolytic Graphite Sheet (PGS) from Panasonic Corporation of Kadoma, Osaka (Japan). If needed, a thermal insulating sheet can be used on top of the thermal transfer material to block heat (e.g., from the sun) to provide a more accurate temperature reading. An example thermal insulating sheet is the Nano Silica Balloon Insulator (NASBIS) from Panasonic.

Measuring absolute temperature of animals using surface-mounted ear tags has proven to be difficult as the results are not consistent, and they are affected by the environment (e.g., sun, wind, rain, temperature, etc.) on external one. Thus, internally placed tags are the most accurate, but they are difficult to implement without an invasive procedure. Surface-mounted temperature sensors, however, may provide an indication of health if they are used to provide relative temperature between animals.

For example, assume the standard healthy temperature for an animal is 100 degrees F., and it is unhealthy if it has a temperature of 104 degrees F. However, on a warm, sunny day, the temperature of an externally mounted sensor may register slightly higher (e.g., 102 degrees F.) due to the radiation from the sun and/or increased air temperature. But if all the temperature sensors suffer a similar effect then as long as an animal's temperature does not deviate greatly from the average of the group (e.g., 4 degrees F.), it is probably healthy. Thus, if on the warm, sunny day, the group average is 102 degrees F., an animal registering 105 degrees F. may be considered healthy due to a small deviation from the increased temperature of the group. This may not be its absolute temperature, but it is enough of an indication of its temperature to classify its health.

For tags from which geographic positions of animals may be determined, positions of herd animals relative to each other may be used as a health classifier. For example, because cows are herd animals, they typically stay relative close to each other (e.g., within 150 m), although they can drift away for short periods of time (e.g., 0.5 hours to 1.0 hours). If a cow stays with 150 m of the herd or separates from the herd for less than 1.5 consecutive hours, they may be classified as healthy. However, if a cow separates from the herd between 150 m and 210 m or separates from the head between 1.5 hours and 2 hours, they may be classified as potentially sick. If a cow separates from the herd more than 210 m or for more than 2 consecutive hours, they may be classified as sick.

In some implementations, controller 830 may receive queries (e.g., pings) and generate a response. The query may be directed specifically to the tag or to a group of tags (e.g., in a pen). The response may include the identifier for the tag. The response may also include data regarding the associated animal (e.g., location history, medical history, temperature history, movement history, etc.), which may be stored in memory.

If controller 830 determines that the animal might be unhealthy, the controller may activate GPS receiver 840 and command it to measure the animal's position (e.g., at regular intervals). The GPS receiver may measure the animal's position on a periodic basis (e.g., every hour, every ten minutes, every minute) or on event-driven basis (e.g., when the animal is moving).

The movement of an animal is helpful in understanding the condition of the animal in a given time period. Controller 830 can process the position data to generate movement data or the position data can be sent to a remote computer system for analysis.

In some modes of operation, tag 800 may send data (e.g., tag identifier and/or status) on its own (e.g., without being queried). The tag may, for example, accomplish this based on a time or an event basis.

Short-range communication system 870 may detect when it is near another short-range communication device (e.g., located on or near a water trough) and communicate an identifier associated with the tag, along with data regarding the animal in particular implementations. In certain implementations, short-range communication system 870 and the other short-range communication device may form a target-initiator pair. Short-range communication system 870 allows a system (e.g., like control system 120) that communicates with the other short-range communication device to detect when an animal is approaching a location (e.g., a water trough).

Although FIG. 8 illustrates an example tag for a livestock management system, other example tags could include fewer, additional, and/or a different arrangement of components. For example, a tag could include a user interface. A user interface could, for instance, include one or more user input devices (e.g., a button, a touchpad, a stylus, or a microphone) and/or one or more user output devices (e.g., a display, a speaker, or an indicator). As another example, a tag may not include a power source. In particular implementations, for example, a tag may be wirelessly powered based on requests. Then, the long-rang communication system may not be present. In certain implementations, a tag may not include a movement sensor system. Instead, for example, the movements may be based on the GPS measurements. When query rates are high enough, the tag may allow for customized watering (e.g., moving treated water to a trough for a specific animal). Thus, the short-range communication system may not be present. In some implementations, location information can be computed based on trilateration of signals in a communication system (e.g., the long-range communication system), rendering the GPS receiver optional. As a further example, a tag may not include a temperature sensor.

Figure 9:
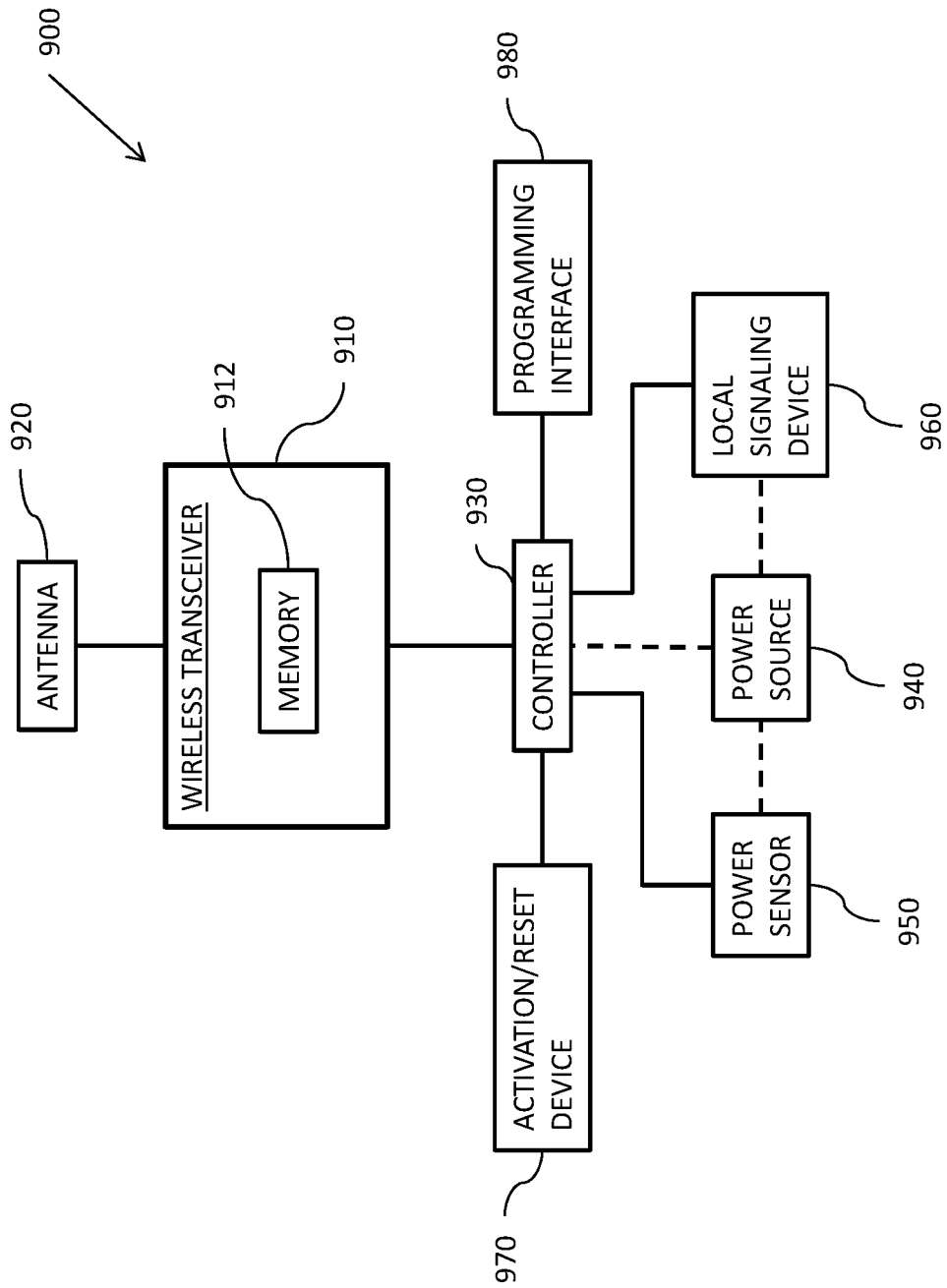
FIG. 9 is block diagram illustrating selected components of another an example tag.

FIG. 9 illustrates selected electronic components for an example animal tag 900. Tag 900 may, for example, be worn in the ear of an animal or on an animal's collar.

In general, tags may communicate with wireless transceivers in a passive or active manner. In a passive manner, the tags may be energized by signals from wireless transceivers and use this energy to transmit their identifiers, along with any other information (e.g., data about the associated animal), back to the wireless transceivers. In an active manner, the tags may generate their own power (e.g., by chemical reaction) and transmit their information to wireless transceivers (e.g., when requested or on a schedule). In the illustrated implementation, tag 900 uses radio-frequency identification (RFID) techniques. RFID chips may store identifiers for an animal and/or information history on the animal. The data that is stored can be transmitted through the wireless transceiver. Tags may be in place on the animals when they arrive at system 100 or placed on them when they arrive. Suitable RFID tags are available from Allflex, and suitable RFID chips are available from NXP Semiconductors.

Among other things, tag 900 includes a wireless transceiver 910, an antenna 920, a controller 930, a power source 940. Transceiver 910 is adapted to receive and send information wirelessly using RF techniques. In particular implementations, transceiver 910 may be an RFID chip and use radio frequencies in the UHF band (e.g., around 900 MHz). Transceiver may, for example, be an SL3S4021 from NXP Semiconductors.

Wireless transceiver 910 includes memory 912 therein. The memory may, for example, be non-volatile memory (e.g., EEPROM). Memory 912 may store the identifier for the tag as well as data from controller 930 (e.g., power level, timers, tag temperature, local alert status, etc.) and from the gateway (e.g., media record). This data may be sent by wireless transceiver 910 when the tag is within transmitting range of a tag reader.

Antenna 920 operates with transceiver 910 and is adapted to radiate and absorb RF transmissions at a certain frequency. The antenna may, for example, be embedded in a printed circuit board (PCB). Particular implementations may use two antennas.

Controller 930 is adapted to analyze RF transmissions and determine whether and how to respond. In certain modes of operation, controller 930 may respond with data stored on the tag. This data may, for example, include health and treatment data regarding the associated animal and/or data regarding the tag (e.g., power level). Controller 930 is generally a logic driven device and may, for example, be a microprocessor or a microcontroller. In particular implementations, controller 930 is an STM32L011 F4U6 from STMicroelectronis of Geneva, CH (Switzerland).

Controller 930 may receive power from power source 940. Power source 940 may, for example, be a battery (e.g., a Lithium Thionyl Choloride cell).

Tag 900 also includes a power sensor 950, a local signaling device 960, an activation/reset device 970, and a programming interface 980. Power sensor 950 is adapted to sense the voltage level of power source 940 and provide a digital value to controller 930. Local signaling device 960 is adapted to be activated by controller 930. Local signaling device 960 may be provide audible and/or visual alert. In particular implementations, local signaling device 960 includes a light emitting diode (LED) (e.g., an LJ CKBP-JZKZ-25-1 from Osram Opto Semiconductors of Regensburg, Bavaria (Germany)).

Activation/reset device 970 is adapted to alert controller 930 to begin and/or reset operations. Activation/reset device 970 may, for example, be a switch. In particular implementations, activation/reset device 970 may be a Reed switch. Passing a magnet over the Reed switch will cause it close, generating a magnetic pulse to controller 930, waking it.

Programming interface 980 allows controller 930 to be programmed. Programming interface 930 may, for example, be a serial wire debug interface.

In certain modes of operation, controller 930 may monitor how long it has been since the animal approached water. For example, the controller may use sensing of the tag by an RF sensor as a proxy for when an animal is approaching water. The controller may store when was the last time that the animal approached water in memory. Periodically, the controller may determine how much time has elapsed since the last time that the animal approached a water trough. If the period of time is too long (e.g., more than 8 hours), the controller may activate local signaling device 960.

In certain implementations, tag 900 may convey position data regarding the associated animal to a central controller. For example, the tag may determine and store the location of the animals (e.g., by GPS measurements) and pass this to the central controller. The remote controller may, for instance, analyze the overall movement of a cow over a period of time (e.g., a day). For example, the distance that the cow traveled during the day may be analyzed. The distance could be analyzed by itself (e.g., against a threshold) to determine whether the cow is behaving abnormally or in comparison to other cows in the same pen, in some type of statistical variance (e.g., an analysis of variance analysis).

Tag 900 may also include a movement sensor. The movement sensor may detect movements/non-movements of the animal (e.g., lying down, hanging head low, rumination), and controller 930 may store them for reporting to a gateway when in range of a wireless reader. The movement sensor may, for example, be an accelerometer. Based on the animals movements (e.g., resting time), a health determination may be made for the animal.

In certain implementations, tag 900 may include a temperature sensor. The temperature sensor may be mounted to the back side of the tag's housing so that is next to the animal's ear. While the temperature sensor may give a temperature for the animal, this temperature may not be accurate in an absolute sense. However, it should provide accuracy relative to other animals in the same enclosure (e.g., pen). Based on the animal's relative temperature, a health determination may be made for the animal as described previously.

Figure 9C:
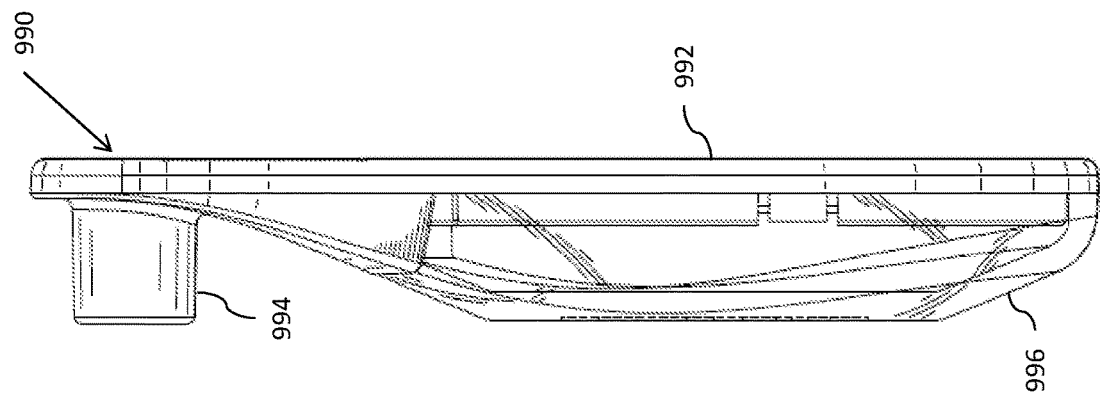
FIGS. 9A-C are line drawings illustrating example housing for a tag.
Figure 9B:
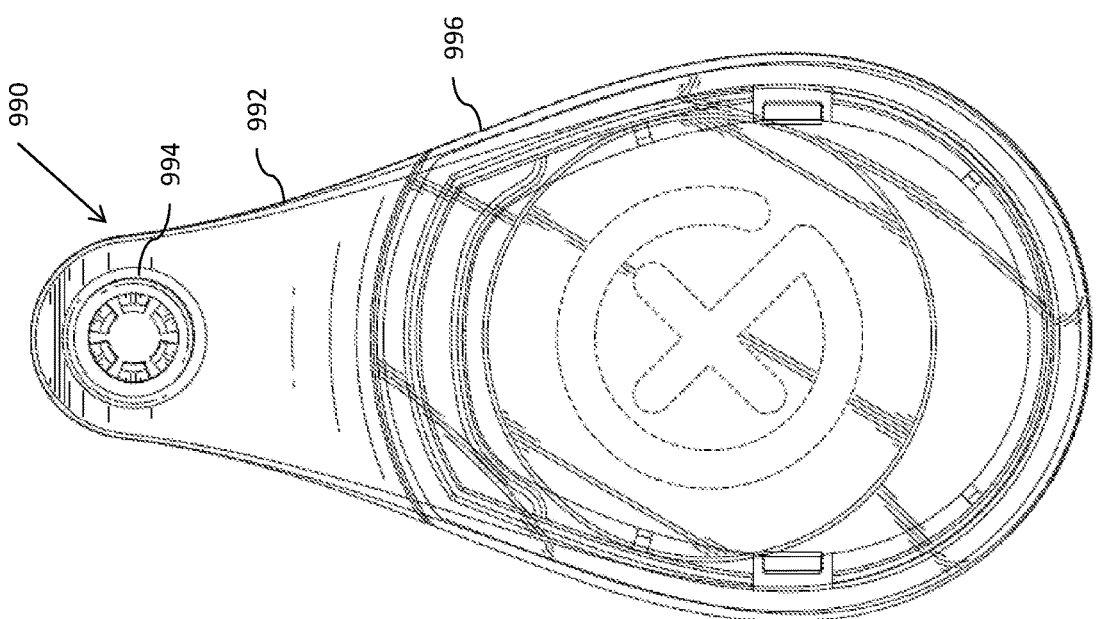
Figure 9A:
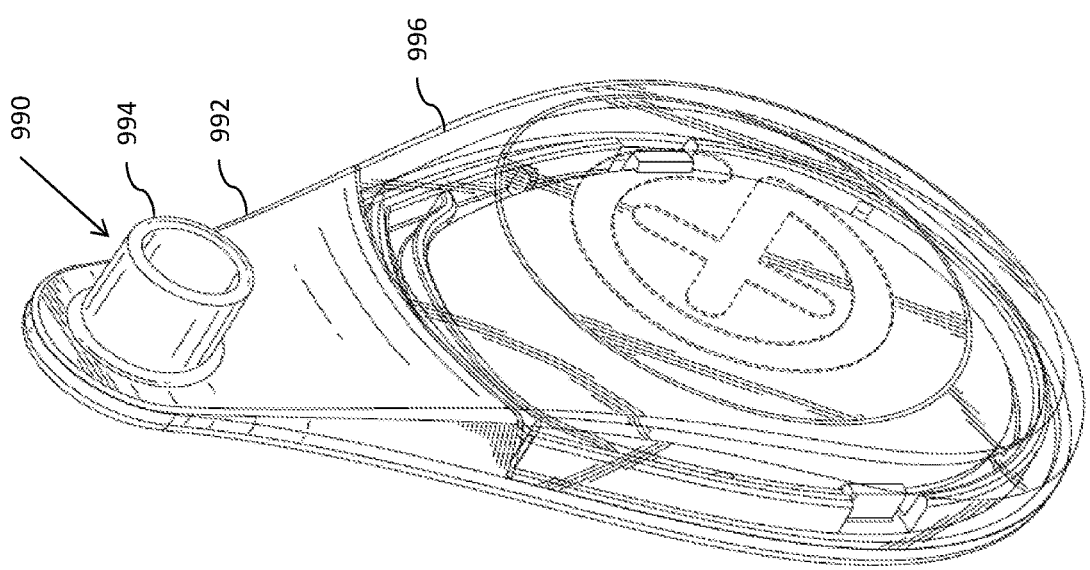

FIGS. 9A-C illustrate an example housing 990 for a tag that is placed in the ear of an animal. Housing 990 may, for example, be used for tag 800 or tag 900. Among other things, housing 990 includes a base 992 and a cover 996.

In this implementation, base 992 has an elongated, teardrop shape. At the top, base 992 includes an aperture 994 through which housing may be secured to an animal's ear through means known in the art. In particular implementations, base 992 is sized so that when secured to an animal's ear (e.g., between the cartilage in the pinna of a cow), the widest portion of the base hangs below the ear. The antenna for the RF sensor may be positioned at the widest portion of the base so as to provide a clear path to the antenna (e.g., so that it is not shielded by the pinna), which should provide enhanced performance. In the illustrated implementation, base 992 is made of plastic, but base 992 may generally be made of any material that can survive for months in the outdoors while attached to livestock and not interfere significantly with low power RF signals.

Cover 996 is removable from base to allow insertion and extraction of a PCB and/or battery. In the illustrated implementation, cover 996 is made of plastic, but cover 996 may generally be made of any material that can survive for months in the outdoors while attached to livestock and not interfere significantly with low power RF signals. In the illustrated implementation, cover 996 is clear to allow a local signaling device (e.g., an LED) to be seen therethrough, but it could be translucent of opaque in other implementations.

In the illustrated implementation, base 992 and cover 996 are designed so that they have few, if any, portions that can snag on objections (e.g., fences, trees, etc.). In some implementations, cover 996 may be ultrasonically welded to base 992.

Figure 10:
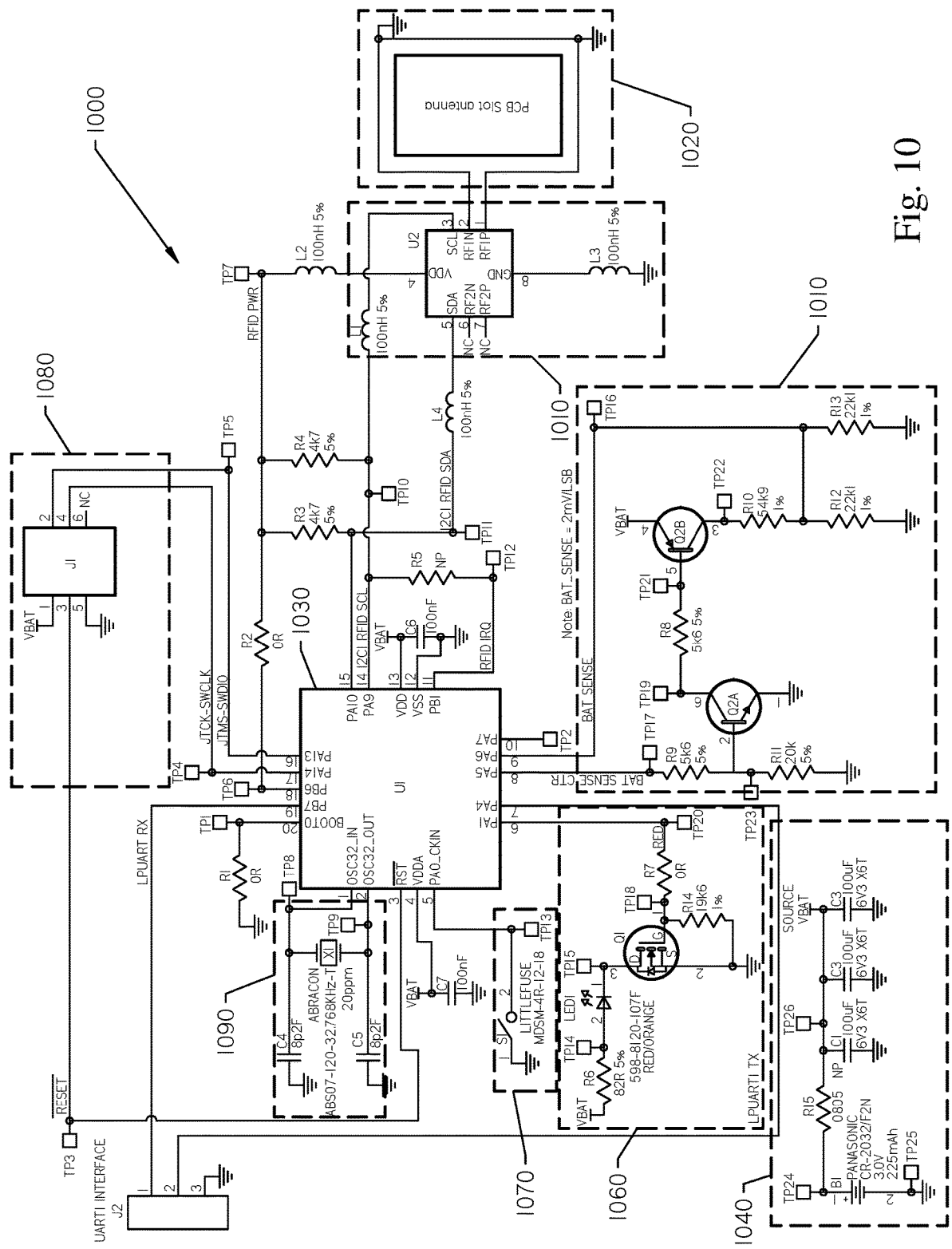
FIG. 10 is a schematic diagram illustrating another example tag.

FIG. 10 is a schematic diagram illustrating an example animal-mounted tag 1000. Similar to tag 900, tag 1000 includes an RFID chip 1010, an RF antenna 1020, a controller 1030, a power source 1040, a power sensor 1050, a local signaling device 1060, an activation/reset switch 1070, and a programming interface 1080. Tag 1000 also includes a clock 1090.

RFID chip 1010 is adapted to receive and send information wirelessly using RF techniques. In particular implementations, chip 1010 may use radio frequencies in the UHF band (e.g., around 900 MHz). Transceiver may, for example, be an SL3S4021 from NXP Semiconductors.

Wireless transceiver 1010 includes memory therein. The memory may, for example, be non-volatile memory (e.g., EEPROM). The memory may store the identifier for the tag as well as data from controller 1030 (e.g., power level, tag temperature, etc.). This data may be sent by wireless transceiver 1010 when the tag is within transmitting range of a tag reader.

Antenna 1020 is formed in a slot of a printed circuit board and is adapted to radiate and absorb RF transmissions at a certain frequency. Antenna 1020 operates in conjunction with RFID chip 1010 to send RF transmissions.

In certain modes of operation, controller 1030 may monitor how long it has been since the animal associated with the tag approached water. For example, the controller may use reading of the tag by an RF sensor as a proxy for when an animal is approaching water. To understand when the animal is approaching the water trough, the tag reader may write to the tag memory when the animal is approaching the water trough. The tag controller may then use this written data to understand when the last time was that the animal approached the water trough and internally reload a countdown timer. The controller may then determine how much time has elapsed since the last time that the animal approached a water trough. If the period of time is too long (e.g., more than 8 hours), the controller may activate local signaling device 1060. Local signaling device 1060 may remain active for a predetermined period of time (e.g., 2 hours). The activation is programmable to extend battery life.

In particular implementations, controller 1030 may send and/or receive blocks of data through RFID chip 1010 through an I2C bus between controller 1030 and RFID chip 1010. Data sent to the controller may be determined based on the remote controller's logic or by instructions a user (e.g., a rancher or a veterinarian) enters via a cloud side application.

In certain modes of operation, controller 1030 may monitor how long it has been since the animal associated with the tag approached water. For example, the controller may use reading of the tag by an RF sensor as a proxy for when an animal is approaching water. To understand when the animal is approaching the water trough, the tag reader may write to the tag memory when the animal is approaching the water trough. The tag controller may then use this written data to understand when the last time was that the animal approached the water trough and internally reload a countdown timer. The controller may then determine how much time has elapsed since the last time that the animal approached a water trough. If the period of time is too long (e.g., more than 8 hours), the controller may activate local signaling device 1060. Local signaling device 1060 may remain active for a predetermined period of time (e.g., 2 hours). The activation is programmable to extend battery life.

Controller 1030 receives power from power source 1040. Power source 1040 is a battery in this implementation. Power source 1040 also supplies power to power sensor 1050 and local signaling device 1060.

Power sensor 1050 is adapted to sense the voltage level of power source 1040 and provide a digital value to controller 1030. Local signaling device 1060 is adapted to be activated by controller 1030. In this implementation, local signaling device 1030 is a light emitting diode (LED) (e.g., an LJ CKBP-JZKZ-25-1 from Osram Opto Semiconductors of Regensburg, Bavaria (Germany)).

Activation/reset device 1070 is adapted to alert controller 1030 to begin and/or reset operations. Activation/reset device 1070 may, for example, be a switch. In this implementation, activation/reset device 1070 is a Reed switch.

Programming interface 1080 allows controller 1030 to be programmed. Programming interface 1030 is a serial wire debug interface in this implementation.

In certain modes of operation, controller 1030 may monitor how long it has been since the animal associated with the tag approached water. For example, the controller may use reading of the tag by an RF sensor as a proxy for when an animal is approaching water. To understand when the animal is approaching the water trough, the tag reader may write to the tag memory when the animal is approaching the water trough. The tag controller may then use this written data to understand when the last time was that the animal approached the water trough and internally reload a countdown timer. The controller may then determine how much time has elapsed since the last time that the animal approached a water trough. If the period of time is too long (e.g., more than 8 hours), the controller may activate local signaling device 1060. Local signaling device 1060 may remain active for a predetermined period of time (e.g., 2 hours). The activation is programmable to extend battery life.

In certain implementations, tag 1000 may convey position data regarding the associated animal to a central controller (e.g., a gateway). For example, the tag may determine and store the location of the animals (e.g., by GPS measurements) and pass this to the gateway. The gateway may, for instance, analyze the overall movement of a cow over a period of time (e.g., a day). For example, the distance that the cow traveled during the day may be analyzed. The distance could be analyzed by itself (e.g., against a threshold) to determine whether the cow is behaving abnormally or in comparison to other cows in the same pen, in some type of statistical variance (e.g., an analysis of variance analysis).

Tag 1000 may also include a movement sensor. The movement sensor may detect movements of the animal, and controller 930 may store them for reporting to a gateway when in range of a wireless reader. The movement sensor may, for example, be an accelerometer. Based on the animals movements (e.g., resting time), a health determination may be made for the animal.

By using power source 1040, tag 1000 may determine and supply extra information to a gateway and provide a signal to locate a potentially sick animal. Power source 1040 may also allow tag 1000 to be written to when it is out of range for responding to an RFID reader. By being powered, incoming messages (e.g., including data and/or instructions), assuming they can reach tag 1040, may be retrieved by controller 1030 and acted thereon. An example instruction is to activate or deactivate the local signaling device.

Tag 1000 is, however, useful even if power source 1040 has failed because RFID chip 1010 does not depend on power from power source 1040. Thus, the identity of the tag may still be read by an RFID reader, and the approach of an animal provided to a gateway.

In particular implementations, tag 1000 may have a conformal coating applied over the surface of the electronics to protect them from the environment. The conformal coating may be acrylic or plastic that is sprayed or brushed on.

Figure 11:
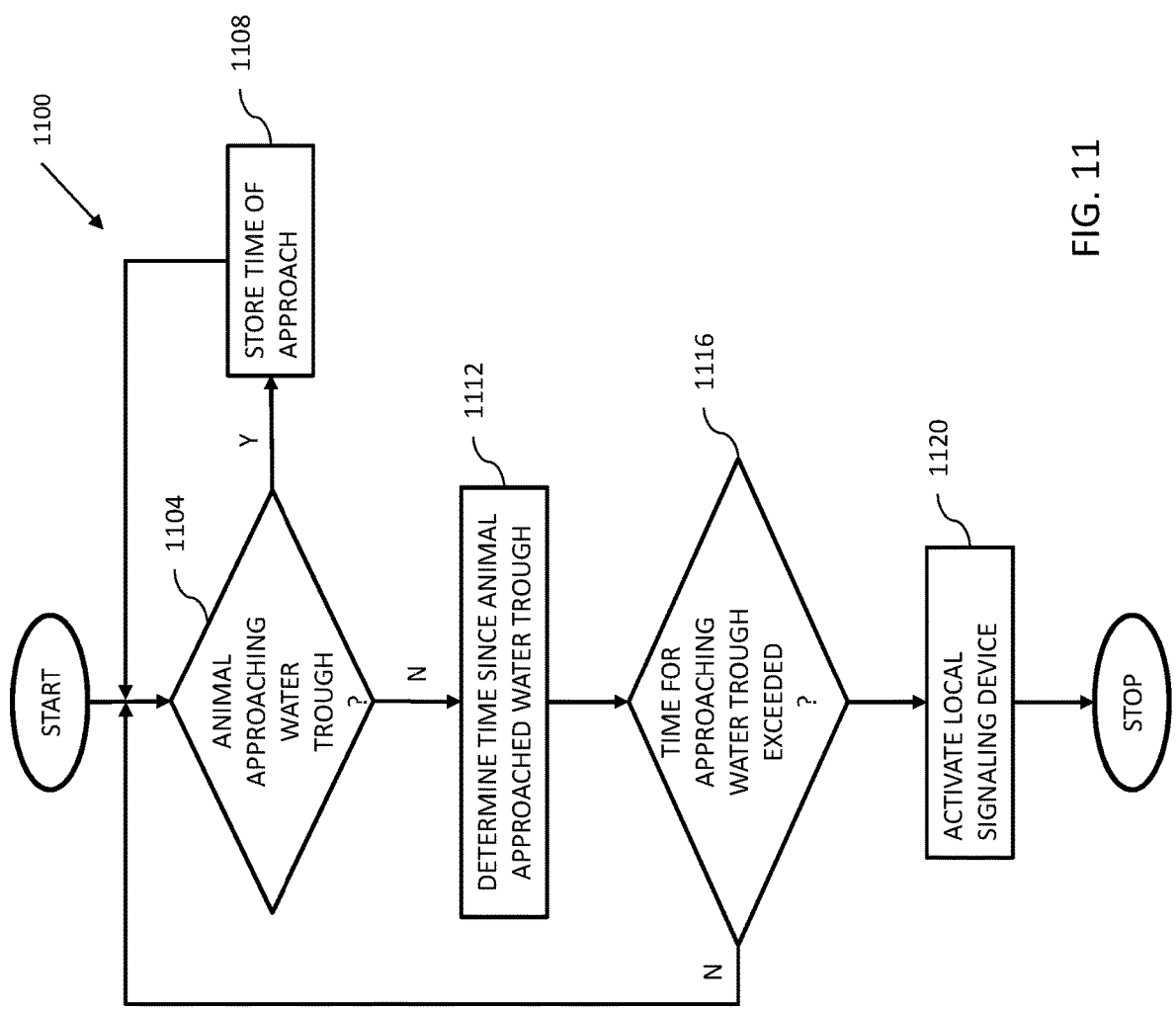
FIG. 11 is a flowchart illustrating selected operations of an example process for livestock management.

FIG. 11 illustrates another example process 1100 for livestock management. Process 1100 may, for example, be implemented by a controller similar to controller 930.

Process 1100 calls for determining whether an animal is approaching a water trough (operation 1104). Determining whether an animal is approaching water can, for example, be accomplished by determining whether the tag comes within proximity of an RFID sensor. If the animal is approaching water, process 1100 calls for storing the time of approach (e.g., operation 1108). The time may, for example, be stored in computer memory. Process 1100 then calls for again determining whether the animal is approaching water (operation 1104).

If the animal is not approaching water, process 1100 calls for determining the time since the animal approached the water trough (operation 1112). Determining the time since the animal approached the water trough may be accomplished by comparing the current time to the last stored time that the animal approached the water trough. Process 1100 also calls for determining whether a time for approaching the water trough has been exceeded (operation 1116). For example, typically well cows approach water less than every 5 hours, cows that are mildly sick approach water between every 5-10 hours, and cows that are sick approach water greater than every 10 hours. Thus, for example, is a cow has not approached a water trough in over 10 hours, the time for approaching a water trough has been exceeded because the cow is properly classifiable as sick.

If the time for approaching a water trough is not exceeded, process 1100 calls for continuing to determine whether the animal is approaching the water trough (operation 1104). If, however, the time for approaching the water trough is exceeded, process 1100 calls for activating a local signaling device (operation 1120). The local signaling device may, for example, be a light-emitting device (e.g., an LED) that is flashed. The local signaling device may, for example, assist an attendant in locating the potentially sick animal. Due to power considerations, in particular implementations, the local signaling device may only operate for a period of time (e.g., 2-4 hours). In certain implementations, the local signaling device may be operated at dawn and/or dusk.

Example Livestock Management System

Figure 12A:
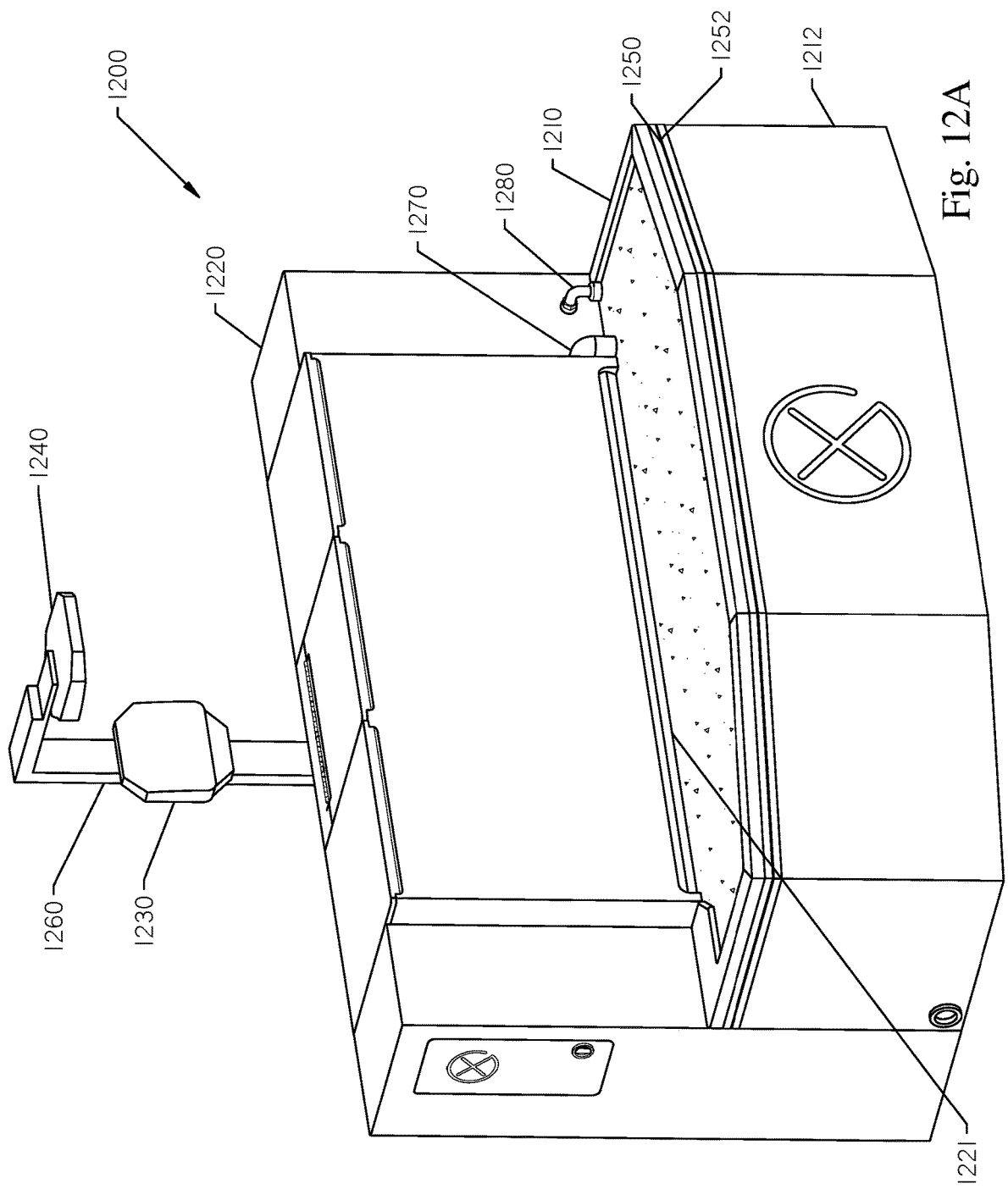
FIG. 12A is a line drawing illustrating selected components of an example system for livestock management.
Figure 12B:
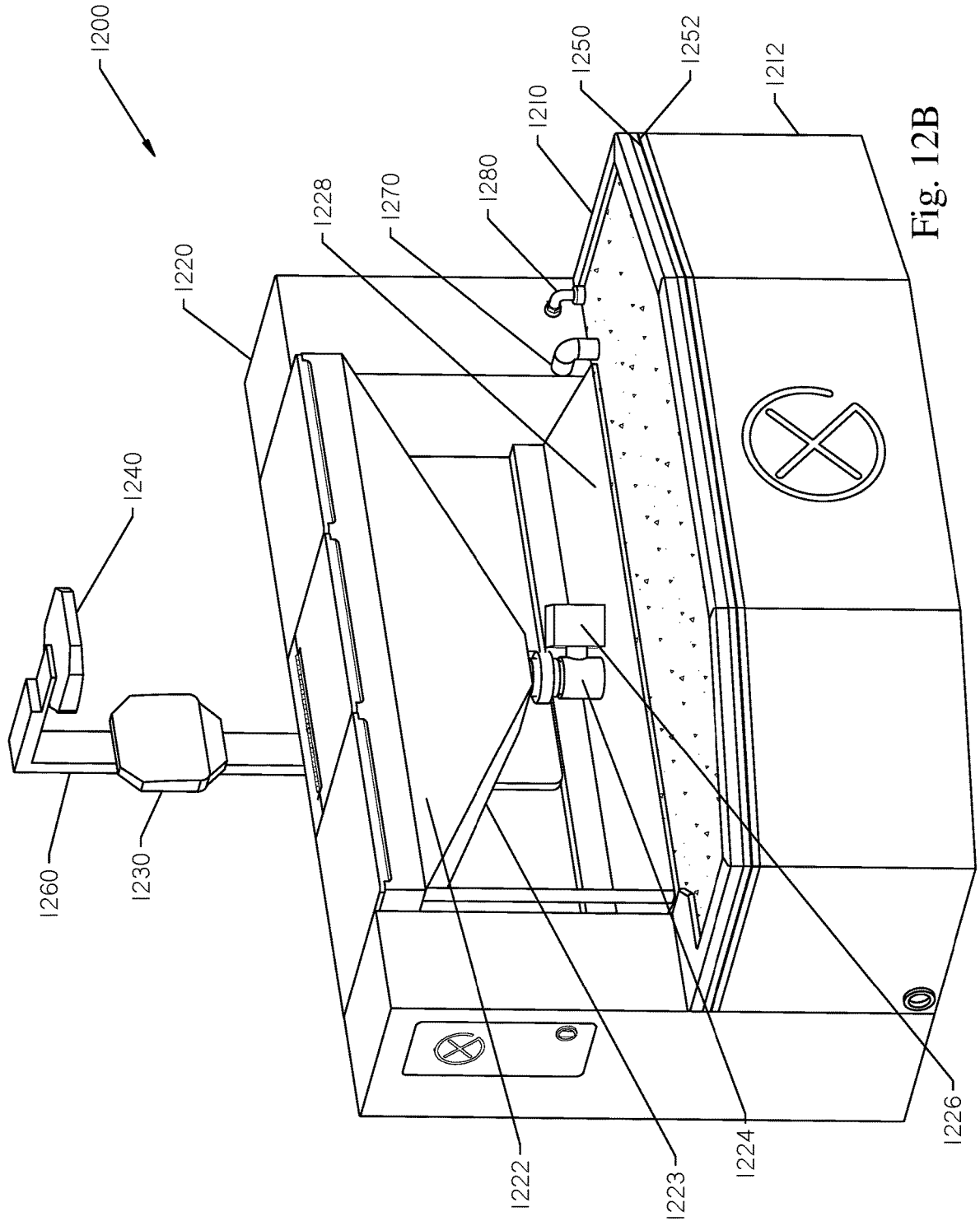
FIG. 12B is a line drawing illustrating the example livestock management system of FIG. 1A with a portion broken away.
Figure 12C:
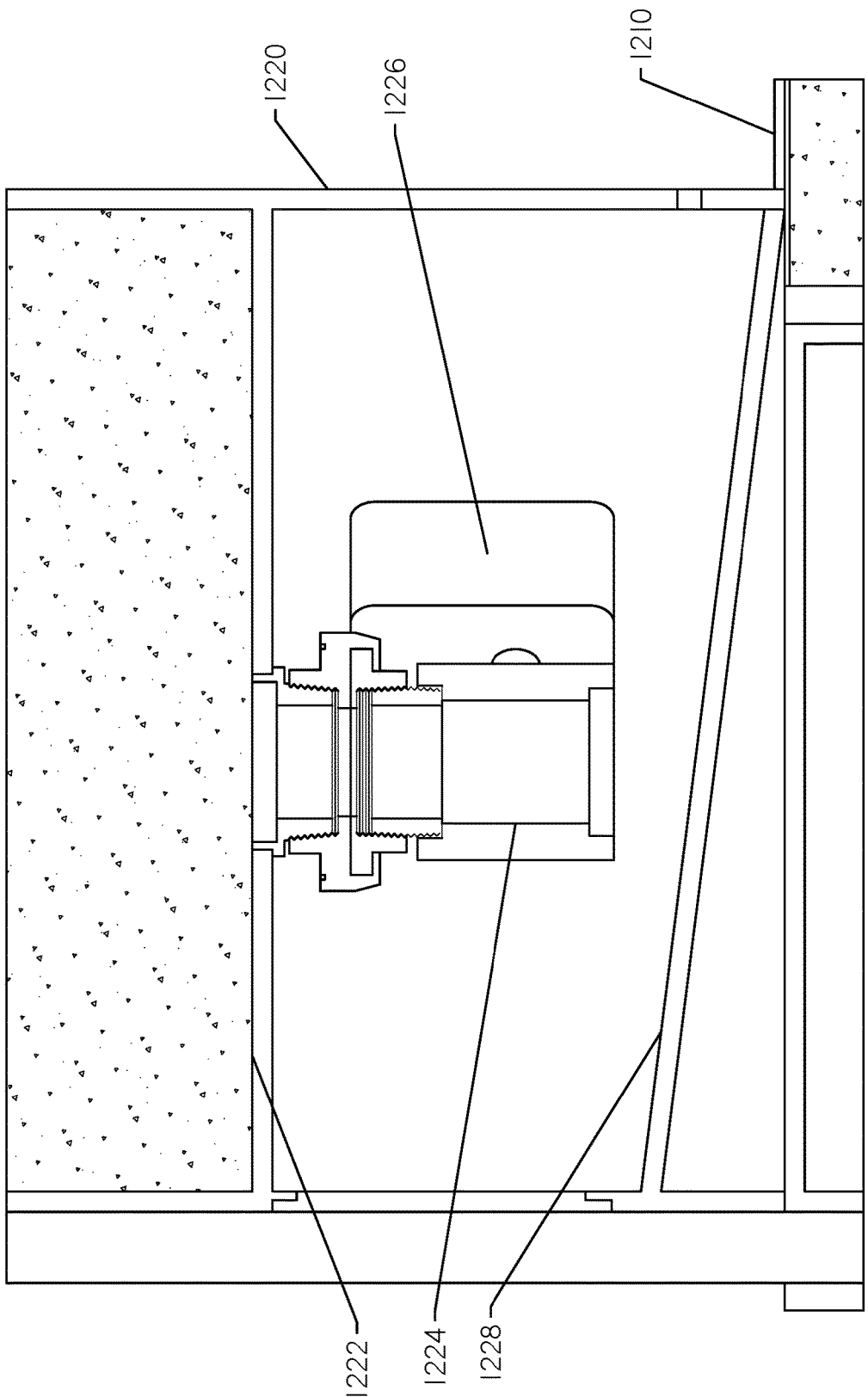
FIG. 12C is a line drawing illustrating a cut-away view of the example livestock management system of FIG. 12A.

FIGS. 12A-C illustrate selected components of an example livestock management system 1200. Among other things, system 1200 includes a water trough 1210, a water reservoir 1220, a first RF sensor 1230, a second RF sensor 1240, and a third RF sensor 1250. RF sensor's 1230-1250 are adapted to sense an animal-mounted tag when it is in proximity to the water trough 1210.

Water trough 1210 includes walls 1212 that may generally be configured to hold any amount of water. In the illustrated implementation, walls 1212 are angled sections that form a partial octagon and allow water trough 1210 to hold approximately 250 gallons. The water in water trough may be standard potable water or may be treated water. Water trough 1210 may, for example, be made of plastic (e.g., Copolymer Polypropylene) or metal (e.g., aluminum).

In particular implementations, the water may be treated via ionization to achieve an alkaline condition (i.e., pH above 7.0) and/or a negative ORP (e.g., −200 mV). In particular implementations, the treated water may have a pH around 9.0 and an ORP of around −800 mV. A negative ORP provides a large number of negatively charged ions that provide antioxidant potential. Antioxidants work by slowing or preventing the damage caused by free radicals, which can lead to, among other things, cell dysfunction. Cows, for example, can have an overload of free radicals due to the stress of being shipped and/or being sick. The water may also be ionized (e.g., micro-clustered).

Water reservoir 1220 is located above water trough 1210 and includes a tank 1222 for storing treated water for supply to water trough 1210. In the illustrated implementation, the water is supplied from tank 1222 to water trough 1210 by gravity, but it may be supplied by other means (e.g., pump) in other implementations. Tank 1222 includes angled walls 1223 to enhance the flow of water out of the bottom of the tank. Walls 1223 may generally be angled between 10 degrees to 40 degrees to enhance the flow. In the illustrated implementation, water reservoir 1220, holds about 50 gallons, and walls 1223 are angled about 24 degrees from the horizontal. This allows all of the water to flow out of the tank in about 15 seconds. Tank 1212 may hold other amounts in other implementations.

Water reservoir 1220 also includes a valve 1224 for regulating the flow of water from tank 1222 to water trough 1210. Valve 1224 may, for example, be a butterfly valve, a gate valve, or a ball valve. Valve 1224 may, for example, be sized to release all of the water in water reservoir 1220 in approximately 15 seconds. Valve 1224 has an electrical control unit 1226 coupled thereto to actuate the valve. Control unit 1226 may be operated under the control of a controller (to be explained below). Control unit 1226 may, for example, contain a solenoid. In the illustrated implementations, valve 1224 is a 3 inch valve.

The water released from tank 1222 through valve 1224 contacts wall 1228 of water reservoir 1220 and flows out through slot 1221 into water trough 1210. Wall 1228 may, for example, be the floor of water reservoir 1220 or an interior wall. In the illustrated implementation, wall 1228 is angled upward from horizontal towards water trough 1210 to direct the water to slot 1221. Angling wall 1228 upward reduces the drop from the end of valve 1224 to wall 1228 and reduces the change of direction of the water upon contacting the wall. This reduces agitation of the treated water, which may cause it to lose, or at least drastically reduce, ORP. The angle of wall 1228 may be adjusted based on the amount of water to be released per unit of time, but may generally be between 5 degrees and 30 degrees. In the illustrated implementation, the angle is approximately 8 degrees.

RF sensor 1230 is positioned above water reservoir 1220 and has the ability to read an animal-mounted radio-frequency identification (RFID) transponder in the far field from the trough. The tag could, for example, be on an animal's ear.

RF sensor 1230 may, for example, read an animal-mounted RFID transponder at an effective range of about 8-12 m. RF sensor 1230 may operate in the UHF band (e.g., at about 900 MHz) and have a circular beam width of about 70 degrees. In particular implementations, RF sensor 1230 may be an Ha-VIS RF-ANT-WR30-US from Harting Electric GmbH & Co. of Espelkamp, NRW (Germany). When mounted about 1.6 m from the ground, RF sensor 1230 may provide a range of about 10 m. The range may be controlled by the antenna pattern and the power supplied by the RF reader. RF sensor 1230 may be mounted at various heights depending on application.

RF sensor 1240 is also positioned above water reservoir 1220 and has the ability to read an animal-mounted radio-frequency identification target in the intermediate field from the trough. For example, RF sensor 1240 may read an animal-mounted RFID transponder at an effective range of about 4-6 m. RF sensor 1240 is oriented at an angle (e.g., about 80 degrees) relative to RF sensor 1230 to provide this field. RF sensor 1240 may, for instance, operate in the UHF band (e.g., at about 900 MHz) and have a circular beam width of about 70 degrees. When mounted about 2.5 m from the ground, RF sensor 1240 may provide a range of about 3 m. The range may be controlled by the antenna pattern and the power supplied by the RF reader. RF sensor 1240 may be mounted at various heights depending on application. Additionally, RF sensor 1240 may be angled upward (e.g., from 0-45 degrees) in some implementations. RF sensor 1240 may be mounted on an adjustable pivot to allow for alignment.

In the illustrated implementation, RF sensor 1230 and RF sensor 1240 are mounted on a pole 1260, which is coupled to the back or water trough 1210 and water reservoir 1220. Pole 1260 is preferably made of plastic or metal.

In certain modes of operation, controller 1030 may monitor how long it has been since the animal associated with the tag approached water. For example, the controller may use reading of the tag by an RF sensor as a proxy for when an animal is approaching water. To understand when the animal is approaching the water trough, the tag reader may write to the tag memory when the animal is approaching the water trough. The tag controller may then use this written data to understand when the last time was that the animal approached the water trough and internally reload a countdown timer. The controller may then determine how much time has elapsed since the last time that the animal approached a water trough. If the period of time is too long (e.g., more than 8 hours), the controller may activate local signaling device 1060. Local signaling device 1060 may remain active for a predetermined period of time (e.g., 2 hours). The activation is programmable to extend battery life.

RF sensor 1230, RF sensor 1240, and RF sensor 1250 are coupled to an RFID reader (not visible in these drawings, but shown and discussed below). The RFID reader detects when an animal-mounted tag is in proximity to the corresponding RF sensor and reads the identifier from the animal-mounted tag. The identifier from the animal-mounted tag is then associated with an animal by a controller (not visible in these drawings, but shown and discussed below) and decisions are made based on this animal's identity. The RFID reader may also read data from the tag (e.g., power level) and send instructions to the tag (e.g., activate/deactivate local signaling device).

In certain modes of operations, water trough 1210 may have water at any of a variety of levels while tank 1222 of water reservoir 1220 is typically fairly full of water or in the process of being refilled. In the illustrated implementation, water trough 1210 is full of water, but the level may actually be kept slightly under full (e.g., by the amount of water in the water reservoir) to allow for adjusting the water properties without I the trough.

Typically, RF sensor 1230 will be the first of the RF sensors to detect the approach of an animal due to its longer range, although it is not guaranteed to sense the animal-mounted tag, due to a variety of geometries and interfering structures (e.g., other animals). When RF sensor 1230 detects an animal-mounted tag approaching water trough 1210 (e.g., entering the outer bubble around the water trough), the sensor 1230 may read the identity of the tag associated with the animal. The identity of the tag is then sent to the controller, which determines the health classification of the animal (e.g., by consulting a database). If the animal is determined to be classified as healthy, no action may be taken. If, however, the animal is determined to be unhealthy, the controller may command the valve control unit 1226 to open the valve to deposit a determined amount of treated water into water trough 1210 before the animal arrives. The release rate of the valve may be timed with the expected arrival time of the animal. For example, a cow typically takes about 15 s to reach water trough 1210 from 10 m.

RF sensor 1240 may be used to further confirm that an animal is heading toward water trough 1210 or to make the initial determination that an animal is heading toward water trough 1210 (e.g., entering the intermediate bubble around the water trough). RF sensor 1240, thus, provides a redundancy for RF sensor 1230. Due to differences in geometry, blockages (e.g., due to other animals' bodies), and RF pathways (e.g., multipath), the reliability of one RF sensor may not be high. Thus, a second RF sensor 1240 provides enhanced performance for the system.

When the animal arrives at the trough, the animal-mounted tag may be sensed by RF sensor 1250. This confirms the animal's arrival at the trough and provides an indication that the animal is actually drinking water. The tag may continue to be sensed while the animal drinks from the water trough. When the animal departs from the water trough, RF sensor 1250 will cease sensing the animal's tag, and the arrival time and the dwell time of the animal at the water trough may be stored.

The animal arrival time and the dwell time at the trough may, in some implementations, be used to determine the health status of the animal. For example, by tracking how often an animal visits the water trough 1210 and how long it stays at the water trough on average, an assessment of animal health may be made. Healthy cows, for instance, typically visit a water trough less than every five hours and spend more than fifteen seconds at the trough, and unhealthy cows visit a water trough more than every ten hours and spend less than five seconds at the trough. Thus, by tracking when a cow arrives at the water trough and how long it stays over a period of time (e.g., 24 hours), an assessment of the animal's health may be made.

In the illustrated implementation, system 1200 also includes a water level sensor 1270. Water level sensor 1270 may inform the controller regarding how much water is in water trough 1210. The controller may then determine how much water to release from water reservoir 1220 into water trough 1210 to affect the water therein. The controller may also take into account how long the water has been in the water trough as the ORP of water declines over times (e.g., often dropping to low levels after five days). Appropriate ratios of treated water to water in the trough are believed to be between 1:2 to 1:10. The water level sensor may, for example, operate by pressure-based techniques (e.g., the amount of pressure on a membrane may give an indication of the amount of water in the trough). Water reservoir 1220 may also include a water level sensor so that the controller knows when to refill the water reservoir. In particular, the water level sensor may be a submersible hydrostatic level transducer.

System 1200 further includes a heating element 1280. Heating element 1280 is useful for preventing the formation of ice during cold weather. Heating element 1280 may, for example, be a stock tank deicer from K&H Manufacturing of Colorado Spring, CO (USA).

System 1200 has a variety of features. For example, the treated water may raise the pH balance of the animals and improve their antioxidant capability, helping them to fight off disease. This may result in decreased need for costly antibiotics and other pharmakinetics used in animal production and management, which will also reduce the toxic runoff (e.g., through urine) of animal byproducts by reducing drug use and overload and reduce the environmental impact of animal operations.

Moreover, by being able control the water for animals, treated water may be provided to one or more animals in an efficient manner. The beneficial properties of treated water subside after a period of time (e.g., 1-6 days). Thus, the water in the water trough must be rejuvenated from time to time with newly treated water. And although only a fraction of the total water amount may be injected to achieve beneficial results, the treated water is considerably more expensive to produce than just standard water. Thus, being able to inject the treated water in an intelligent manner provides beneficial water in a cost effective manner. This should provide higher quality beef, fewer herd losses, increased feedlot profitability, and potential cost savings, as well as reduce the environmental footprint of large feedlot operations.

Additionally, being able to detect the presence of animals allows the treated water to be provided when it is needed. For example, if no animal approaches the water trough for an extended period of time, the water does not have to be maintained at its highest levels. But when an animal approaches, the water may be quickly rejuvenated. Furthermore, being able to detect the presence of animals also allows potentially unhealthy animals to receive highly preferred water. Thus, the systems, processes, and techniques may provide an environmentally sound solution as they improve animal health while conserving electricity. While providing treated water for all animals (e.g., healthy, potentially sick, and sick) is possible, it requires quite a bit of electricity for the water treatment process.

System 1200 also provides insight into the behavior of animals, especially those that are potentially unhealthy. By detecting the presence of animals and determining their identity, system 1200 provides data on how often animals are consuming water and, in certain implementations, how much they are consuming. This may provide insight into the overall health of an animal. Moreover, it may provide early intervention for animals that actually need antibiotics or other treatments and also informed management of the overall herd based on objective standards and reduced inoculations.

Although FIGS. 12A-C illustrate one implementation of a system for livestock management, other systems for livestock management may include fewer, additional, and/or a different arrangement of components. For example, a system may include a water trough with two sections (e.g., one for receiving treated water and one serving as an overflow for the first section). As another example, a system may include one or more pumps to move water between sections. As an additional example, a water trough and/or a storage tank may include sensors to determine properties of the water (e.g., pH, ORP, etc.). The properties of the water can be used in assessing how much treated water to inject into the trough. As a further example, although RF sensors 1230, 1240 are shown as being mounted to the water trough, these sensors may be mounted on other structures (e.g., fences).

Additionally, a system similar to system 1200 may be used at a feed trough. As with system 1200, such a system may detect when an animal is approaching a feed trough (e.g., via a far field sensor) and when an animal is actually at a feed trough (e.g., via a near field sensor). In some implementations, feed may be released depending on the health status of the animal (e.g., by activating gates on chutes).

By sensing the approach and dwell time of the animal, a health determination may be made. For example, cows that are healthy typically visit a feed trough less than every 12 hours and eat for at least 15 minutes. However, cows that are potentially sick may visit a feed trough between every 12-24 hours and eat for between 5-15 minutes, while cows that are sick may visit a feed trough less than every 24 hours and eat for less than five minutes. Thus, by monitoring the arrival time and dwell time, a determination of animal health may be made.

In certain implementations, system 1200 may include a filter that is coupled to a water source (e.g., municipal water supply or well). The filter may be adapted to purify potable water. For example, the filter may extract particles (e.g., heavy metals, fluoride, pesticides, calcium, chloramine, chlorine, nitrates, etc.) and/or gasses (e.g., sulfur) from the potable water. The filter may, for example, be a cartridge-type filter. In particular implementations, an insert of another filter may release (e.g., over time) certain minerals (e.g., calcium) into the filtered water, with possibility of more targeted release of mineral/nutrient supplementation to at risk animals.

Although system 1200 has been discussed primarily with respect to cattle, various aspects of system 1200 may also be useful for other types of livestock. For example, producing treated water may be useful for pigs, sheep, goats, chickens, horses, or any other appropriate type of livestock.

Additionally, although system 1200 has been discussed in the context of a feedlot, various aspect of system 1200 may be used in other settings. For example, the animal location tracking and health prediction may be useful in a field. Furthermore, treated water (e.g., negative ORP) may be provided directly to a series of animals without regard to health. This may, for example, be useful in a poultry operation, where the treated water is provided directly to each animal (e.g., through water feeders). Additionally, treated water may be provided to well dairy cows soon after they are milked. Thus, tracking of animals is not required to provide benefits.

In some implementations, the "leaky" coaxial cable may be replaced with a cone or fan antenna. Such antennas are typically based on printed circuit board fabrication or stamped sheet metal products. Mounting one of these antennas on the oblong end of water trough 1210, for example, may provide read coverage over the entire trough area.

Figure 13:
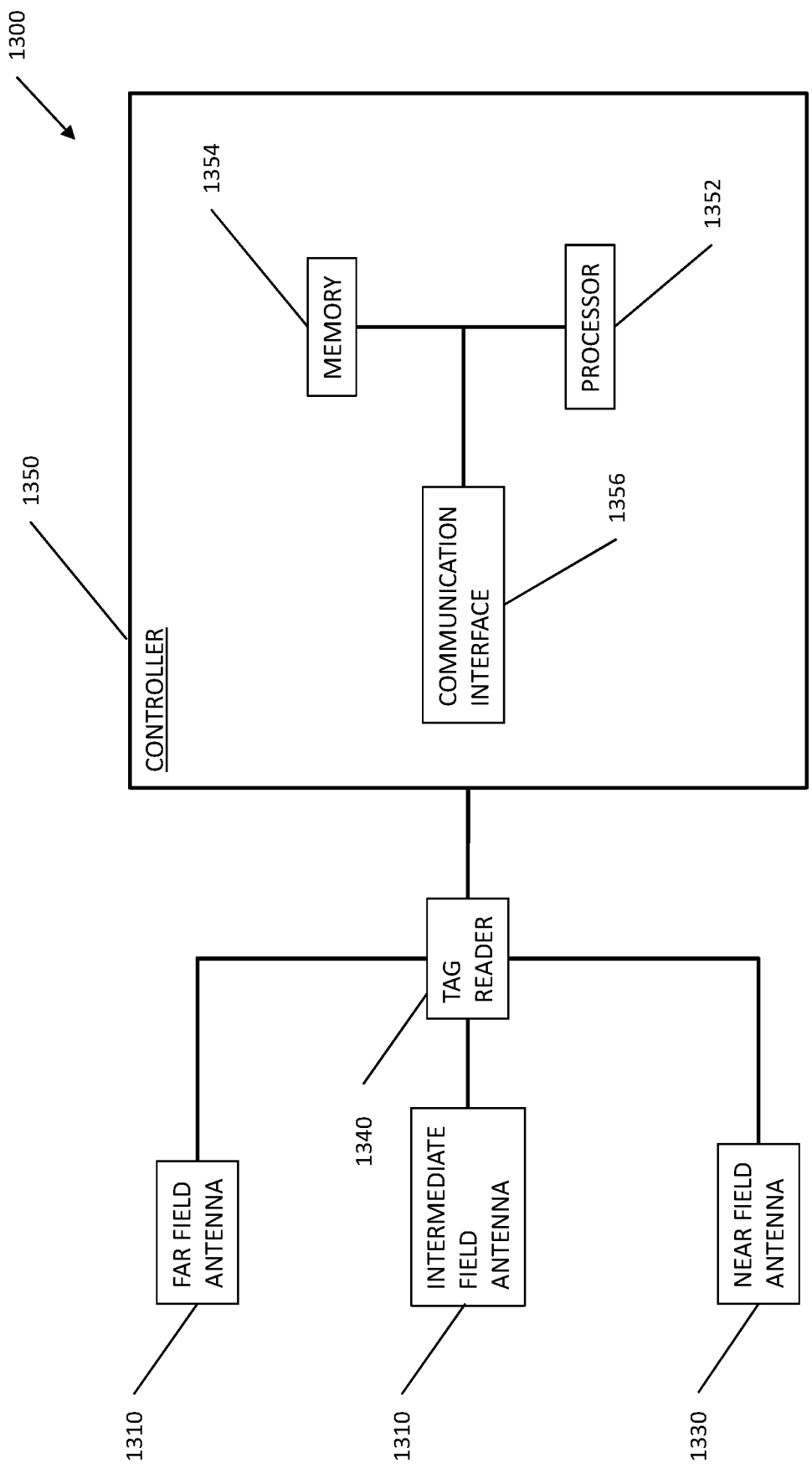
FIG. 13 is a block diagram illustrating selected electronic components for a livestock management system similar to that in in FIGS. 12A-B.

FIG. 13 illustrates an electronic system 1300 for a livestock management system similar to system 1200. System 1300 includes a far-field antenna 1310, an intermediate-field antenna 1320, a near-field antenna 1330, a tag reader 1340, and a controller 1350.

As their names imply, antennas 1310-1330 are able to sense an animal-mounted tag in different zones. Far-field antenna 1310 may, for example, detect a tag at about 8-12 m. And intermediate-field antenna 1320 may, for example, detect a tag at about 4-6 m. Near-field antenna 1330 may detect a tag at ranges of less than 1 m. The zones created by antennas 1310-1230 may, for example, be around a water trough.

Tag reader 1340 is coupled to antennas 1310-1330 and detect the presence of a tag in a zone of the antennas and may also read an identifier off the tag. Tag reader 1340 may also upload data from the tag to controller 1350 and download tag messages from the controller. Tag reader 1340 may, for example, be an RFID reader, such as the RF-350 from Harting.

Controller 1350 is adapted to receive data regarding an animal in the vicinity of one of the antennas and the water in water trough 1210 and regulate the flow of water thereto. In particular, controller 1350 may command a control valve to allow treated water to flow to a water trough based on the approach of an animal. Controller 1350 may be part of a system similar to system 1200 or located remotely. In some implementations, controller 1350 may be part of gateway.

In operation, controller 1350 may generate data at a predetermined time (e.g., every 3 seconds). In particular, database tables on the controller, and in a remote animal analysis system, may track of each event, like the time and antenna a tag was sensed. The database may then be updated with items like last time the animal had been inside the antenna bubble previously. When the antenna at the trough senses a tag, the database records of that tag may be updated to reflect the time the drinking starts. When the antenna read combinations show the animal is not at the trough, the time may be added to the database records of that tag that the animal has stopped drinking.

As illustrated, controller 1350 includes a processor 1352, memory 1354, and a communication interface 1356. Processor 1352 may generally include any logic-based unit for automatically regulating a system (e.g., a microprocessor or a microcontroller). In particular implementations, controller 1350 may include more than one processor.

Memory 1354 may include volatile memory (e.g., random-access memory, registers, etc.) and/or non-volatile memory (e.g., disk memory, read-only memory, etc.). Memory 1354 may store instructions for processor 1352 and data regarding the animals being monitored.

Communication interface 1356 allows controller 1350 to send and receive information (e.g., data and instructions). For example, controller 1350 may receive data regarding the approach of an animal to a water trough, determine the health classification of the animal, determine whether to release water into the water trough, and control the release (e.g., based on the amount of water in the water trough). The communication interface 1330 may operate by wireline (e.g., RS-232, RS-485, USB, Ethernet, etc.) or wireless (e.g., Bluetooth, Wi-Fi, ZigBee, etc.) techniques.

In particular implementations, controller 1350 may know additional information about the water in the water trough. For example, a water trough may include a property sensor and a flow meter. The property sensor may be coupled to the trough and be adapted to detect one or more properties (e.g., pH, ORP, temperature, salinity, chlorine content, etc.) of the water therein. The property sensor may, for example, be a probe-type water property sensor. Such sensors are available from a number of companies, such as Sensorex. An example ORP sensor is the S272CD-ORP from Sensorex. An example pH sensor is the S272CDTC from Sensorex.

The flow meter may be fluidly coupled to the valve and adapted to determine the amount of water flowing to the water trough. The flow meter may, for example, function by vane/piston, differential pressure, turbine, or positive placement techniques.

In particular implementations, the unit supplying the treated water may treat potable water by electrolysis. In electrolysis, water is run between metal plates (e.g., titanium or copper) that are being subjected to an electrical charge. Example electrolysis water treatment units are available from Enagic, Co., Ltd. of Nago (Okinawa), Japan.

In certain implementations, the water treatment system may produce relatively high pH water and relatively low pH water. The relatively high pH water from the water treatment unit may have a pH above 8.0 and, in particular implementations, may have a pH above 9.0. In certain implementations, the water may have a pH between 8.5-9.5. The relatively low pH water from the water treatment unit may have a pH below 6.0 and, in particular implementations, may have a pH below 5.0. In certain implementations, the relatively low pH water may have a pH between 4.5-5.5. The low pH water may also be electrolyzed (e.g., have a positive charge). This low pH water may be used in animal containment areas (e.g., pens, stalls, cages, etc.) to kill bacteria and other infectious matter for cleansing the areas and treating the areas for healthier animal food production procedures. Low pH water may, for example, be especially beneficial in dairy, swine, and poultry operations. Additionally, low pH water (e.g., around 4.5) may be useful for watering plants.

Figure 14:
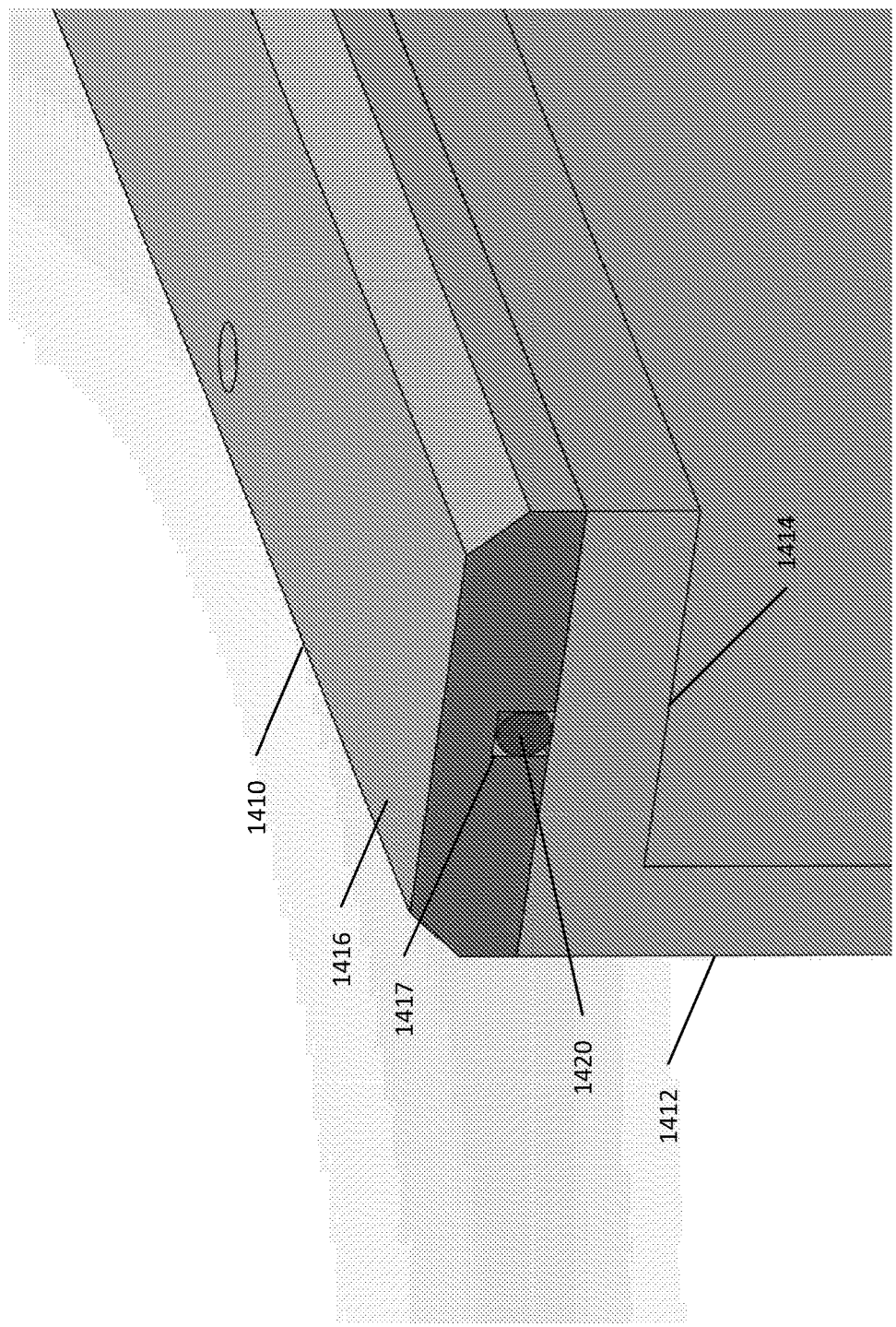
FIG. 14 is a line drawing illustrating an example mounting for an antenna for a livestock management system similar to that in FIGS. 12A-B.

FIG. 14 illustrates an example mounting for an antenna 1420 for a livestock management system. In this implementation, antenna 1420 is a cable (e.g., a leaky coaxial cable) that is routed through a water trough 1410. Water trough 1410 includes a wall 1412, a lip 1414, and a cover 1416. In the illustrated implementation, antenna 1420 resides in a slot in cover 1416. In other implementations, antenna 1420 may, for example, reside in a slot in lip 1414, in a slot in wall 1412, or at any other appropriate location. Cover 1416 may be secured to lip 1414 by any of a variety of techniques (e.g., screws, adhesive, interlock, etc.).

Figure 15:
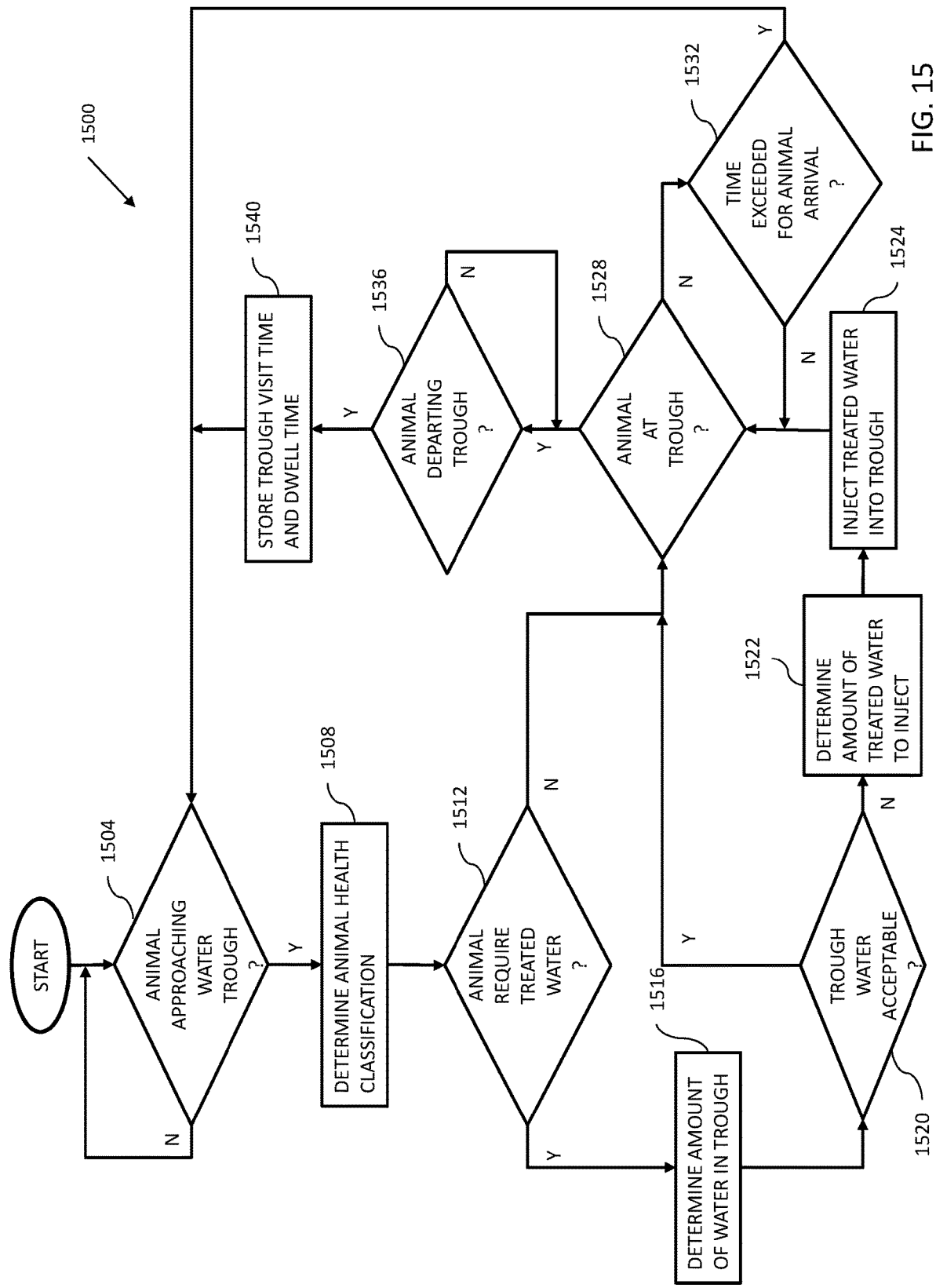
FIG. 15 is a flowchart illustrating selected operations of an example process for livestock management.

FIG. 15 illustrates an example process 1500 for livestock management. Process 1500 may, for example, be implemented by a controller similar to controller 250.

Process 1500 calls for determining whether an animal is approaching a water trough (operation 1504). Determining whether an animal is approaching a water trough may, for example, be accomplished by determining whether an animal is in the vicinity of the water trough. Determining whether an animal is in the vicinity of a water trough may, for instance, be accomplished by detecting a tag on the animal (e.g., electrically) in the far field or the intermediate field. Many communication protocols have very limited ranges (e.g., a few meters). Thus, if an animal's tag (e.g., a target) is in range of a corresponding communication apparatus (e.g., an initiator), an animal near the water trough is likely approaching it. If an animal is not approaching the water trough, process 1500 calls for continuing to determine whether an animal is approaching the water trough (operation 1504).

Once an animal is approaching the water trough, process 1500 calls for determining the health classification of the animal (operation 1508). Determining the health classification of an animal may, for example, be accomplished by reading an identifier associated with an animal-mounted tag and determining whether the identifier has been indicated as being associated with a healthy animal, a potentially unhealthy animal, or an unhealthy animal.

Once the animal's health classification has been determined, process 1500 calls for determining whether the animal requires treated water (operation 1512). An animal may require treated water, for example, if it classified as potentially unhealthy or unhealthy. If the animal does not require treated water, process 1500 calls for determining whether the animal is at the trough (operation 1528).

If, however, the animal requires treated water, process 1500 calls for determining the amount of water in the trough (operation 1516). Determining the amount of water in the trough may, for example, be accomplished by reading the output of a water level sensor (e.g., an underwater pressure sensor or an ultrasonic sensor). Process 1500 also calls for determining whether the trough water is acceptable (operation 1520) Determining whether the water in the trough is acceptable may, for example, be accomplished by evaluating the water level and/or a sensor reading (e.g., for pH, ORP, etc.). If the trough water is acceptable, process 1500 calls for determining whether the animal is at the trough (operation 1528)

If, however, the trough water is not acceptable, process 1500 calls for determining the amount of treated water to inject into the trough (operation 1522). Determining the amount of water to inject into the trough may be dependent on the current amount of water in the trough and/or its properties. For example, it may be desired to mix treated water with standard potable water at a ratio or around 1:4. Thus, knowing the amount of water in the trough will inform how much treated water to inject into the trough. Moreover, the current properties of the water in the trough (e.g., pH, ORP, etc.) may affect the amount of water to inject into the trough. For instance, if the water in the trough already has some of the desirable properties, the amount of treated water to inject into the trough may be reduced. If, however, the water in the trough already has none of the desirable properties, the amount of treated water to inject into the trough may be increased. The amount of water to inject into the trough may also be based on the health classification of the approaching animal. For example, if the animal is only potentially sick, a reduced amount of treated water from what would be provided for a sick animal (e.g., 25%-50%) may be provided to the trough.

Once the amount of treated water to inject into the trough has been determined, process 1500 calls for injecting the treated water into the trough (operation 1524). Injecting the treated water may, for example, involve opening a valve for a given period of time. Opening a valve may involve sending an instruction and/or control signal to a valve controller. In certain implementations, injecting the treated water may include activating a pump to pump the water.

Process 1500 also calls for determining whether the animal has arrived at the trough (operation 1528). Determining whether an animal has arrived at the water trough may, for example, be accomplished by detecting the animal tag with a near-field RF sensor.

If the animal has not arrived at the trough, process 1500 calls for determining whether a period of time for the animal's arrival has elapsed (operation 1532). For given animals, it can be anticipated how long it will take from the initial detection of the animal in the vicinity of the water trough to the actual arrival at the trough. For example, it is estimated that a cow would need 15 s to cover 10 m. If the animal does not arrive at the water trough after a period of time (e.g., double what the estimated time is), process 1500 calls for returning to determine whether an animal is approaching the water trough. In effect, the initial detection event is treated as a false positive and ignored.

If, however the animal arrives at the water trough, process 1500 calls for determining when the animal leaves the water trough (operation 1536). Using a near-field RF sensor, for example, the sensor may be receiving hits from the tag all the while that the animal is at the water trough.

The gateway may, for example, determine when/how often to do a sweeping inventory request—for instance, every 2-5 seconds. The gateway issues the inventory request to the reader, and then the reader does a sweep via its set of antennas to all tags currently within the reach of its antennas. The passive RFID in each tag inside the bubble responds back to the inventory request to the reader, which reports back to the gateway. Thus, almost immediately after the gateway issues an inventory sweep request, it receives back a list of the unique ID numbers of the tags seen. The gateway can also receive from each tag other requested data such as battery strength and temperature.

Once the hits stop, however, it may be assumed that the animal is departing the water trough. Once the animal is departing the water trough, process 1500 calls for storing the trough visit time and dwell time (operation 1540), which may be used to determine animal health. Process 1500 calls for again determining whether an animal is approaching the water trough (operation 1504).

Although FIG. 15 illustrates an example process for livestock management, other processes for livestock management may include fewer, additional, and/or a different arrangement of operations. For example, a process may inject treated water into the trough for all animals that approach. Thus, all animals will receive the treated water. However, the amount of treated water may be adjusted depending on the health status of the animal. As another example, data may be read from the animal mounted tag while the animal is in range of the RFID reader. The data may include performance parameters of the tag (e.g., battery level) or health parameters of the animal (e.g., relative temperature, movements, etc.).

Mobile Livestock Management Systems

FIG. 16 illustrates another example livestock management system 1600. Among other things, system 1600 includes a drone 1610 (i.e., an unmanned aerial vehicle) and a base station 1620. Drone 1610 could, for example, carry a load of about 20 kg for 7 km, although other sized drones could be used in other configurations, and base station 1620 provides a docking and recharging station for the drone. Base station 1620 is communicatively coupled to a communication network 1630 that provides access to an animal analysis system 1640, a user device 1650, and a gateway 1660, which may be similar to those discussed previously.

Among other things, drone 1610 includes a tag reader (e.g., an RFID reader) and an antenna that can read animal-mounted tags from altitude (e.g., 3-10 m). The antenna has a beam width BW (e.g., 70 degrees) within which it can sense tags. Drone 1620 may be programmed to fly a course (e.g., a zigzag or square pattern) over an area A (e.g., a pen of pasture). In doing so, the tag reader may sense animal-mounted ear tags and read data therefrom. In particular implementations, the drone may include GPS capabilities. In these implementations, the drone's position may be coordinated with a tag reading to give an approximate location of an animal associated with a tag.

In some implementations, the drone may be programmed to look for a specific animal (e.g., a potential sick one) during its operations. If the drone finds such an animal (e.g., by sensing the associated tag), it may activate its camera to record video of the animal. The video may be stored on the drone for download to the base station upon return or live streamed back to the base station (e.g., over a cellular connection). From the base station, the video may be delivered to animal analysis system 1640, user device 1650, and/or gateway 1660. In some implementations, the video may be delivered directly to the user device 1650.

In some implementations, the drone may be provided with coordinates of an animal to be inspected (e.g., from GPS measurements from the tag). The coordinates could, for example, come from the gateway. The drone may then fly out to the coordinates and try to sense the animal's tag. If the animal is sensed, the drone may perform other operations (e.g., reading data from the tag, writing data/instructions to the tag, recording video, etc.). If the animal is not at the provided coordinates, the drone may begin a search (e.g., in a spiral manner) starting at the coordinates.

In particular implementations, the positioning of the drone and/or the camera may be controller by a user. For example, once the drone has found an animal of interest, the user may instruct the drone to hover over the animal, circle the animal, or lower over the animal. This may allow the user to obtain more detailed view of a specific condition of the animal (e.g., calving).

System 1600 has a variety of features. For example, by being able to fly, drone 1610 provides a mobile platform for sensing animal tags. Thus, drone 1610 is able to provide data on animals and program the associated tags even when the animals are not near a stationary location (e.g., water trough 1210). Although sensing the tags may be somewhat random due to the unknown distribution of animals, by systematic search, the drone should be able to sense most, if not every, animal tag in the given area. Thus, updates one animal status (e.g., location, temperature, etc.) as well as tag status (e.g., power level, programming status, etc.) may be acquired.

Additionally, drone 1610 can be sent out on specific assignments (e.g., to search for an animal that has not reported in at a water trough for a certain period of time or has an elevated temperature). Once located, the drone may read data from the tag (e.g., animal temperature) and acquire video of the animal, which may be used in assessing whether to send a human out to check on the animal. Thus, the drone may provide cost savings over sending humans out to review and/or search for animals.

Figure 17:
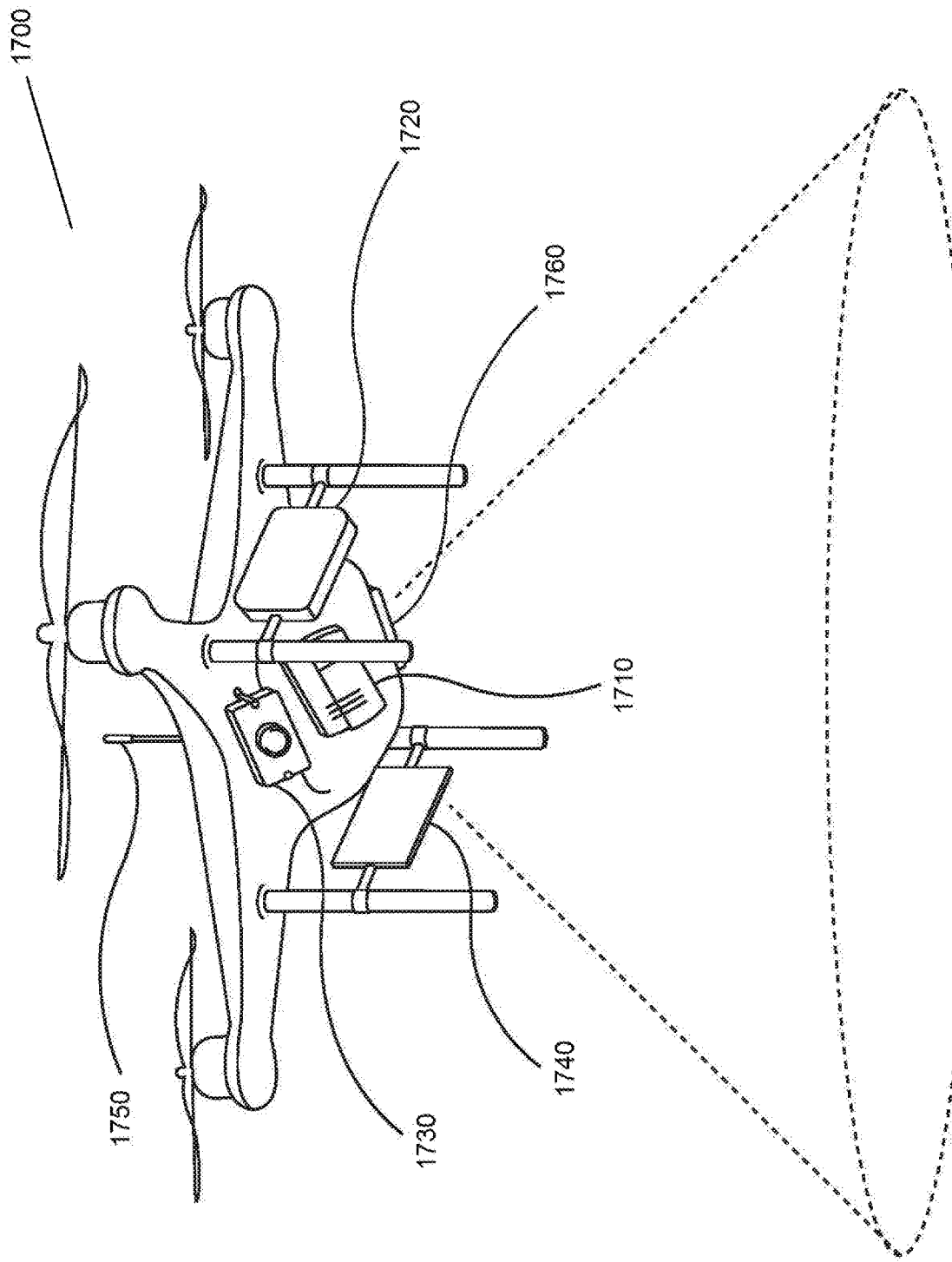
FIG. 17 is a line drawing illustrating an example drone for a livestock management system.

FIG. 17 illustrates an example drone 1700. Drone 1700 may for example, be useful in system 1600.

Among other things, drone 1700 includes a patch antenna 1710 and an RFID reader 1720. Using antenna 1710 and RFID reader 1720, drone 1700 may sense animal-mounted tags as drone 1700 flies over them. Antenna 1710 has a circular beam width BW in which the animal tags should reside to be sensed. By completely scanning an area in successive passes with the beam, most, if not all, tags in the area may be sensed.

Drone 1700 also includes a high definition camera 1730. Using camera 1730, drone 1700 may record video of an animal of interest.

Drone 1700 further includes a processor 1740. Processor 1740 is responsible for processing the data from sensed tags and sending data to the sensed tags.

Drone 1700 also includes a cellular transceiver 1750 and a battery pack 1760. Cellular transceiver 1750 is responsible for providing a wireless link to the drone's base station. Through the wireless link, the drone may convey data that is sense during its flight (e.g., tag identifiers and animal data) and receive updated instructions (e.g., flight path, hover, camera activation, etc.). In certain modes of operation, drone 1700 may search for animals have associated tags by progressively covering an area with the beam on antenna 1710. When an animal's tag is sensed, the identifier and any associated information (e.g., animal temperature) may be read from the tag. The drone may report this back to its base stations in real time or upon return and docking.

Drone 1700 may also obtain video of particular animals. For example, when the tag associated with an animal is sensed, drone 1700 may hover and activate camera 1730 for a period of time (e.g., 30 s). Drone 1700 may then continue on its flight path over the area.

Computer Implementations

The flowchart and block diagrams in the figures illustrate the architecture, functionality, and operation of systems, methods, and computer program products of various implementations of the disclosure. In this regard, each block in the flowchart or block diagrams may represent a module, segment, or portion of code, which can include one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or the flowchart illustration, and combination of blocks in the block diagrams and/or flowchart illustration, can be implemented by special purpose hardware-based systems the perform the specified function or acts, or combinations of special purpose hardware and computer instructions.

As will be appreciated by one skilled in the art, aspects of the present disclosure may be implemented as a system, method, or computer program product. Accordingly, aspects of the present disclosure may take the form of an entirely hardware environment, an entirely software embodiment (including firmware, resident software, micro-code, etc.), or an implementation combining software and hardware aspects that may all generally be referred to herein as a "circuit," "module," or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of a computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be a tangible medium that can contain or store a program for use by or in connection with an instruction execution system, apparatus, or device.

A computer readable signal medium may include a propagated data signal with computer readable program code embodied therein, for example in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any medium, including but not limited to wireless, wireline, optical fiber cable, RF, etc. or any suitable combination of the foregoing.

Computer program code for carrying out operations for aspects of the disclosure may be written in any combination of one or more programming languages such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the disclosure are described below with reference to flowchart illustrations and/or block diagrams of methods, apparatus (systems), and computer program products according to implementations. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other device to function in a particular manner, such that the instructions stored in the computer readable medium produce an article of manufacture including instructions that implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus, or other devices to produce a computer implemented process such that the instructions that execute on the computer or other programmable apparatus provide processes for implementing the functions/acts specified in the flowchart and/or block diagram block or blocks.

Figure 18:
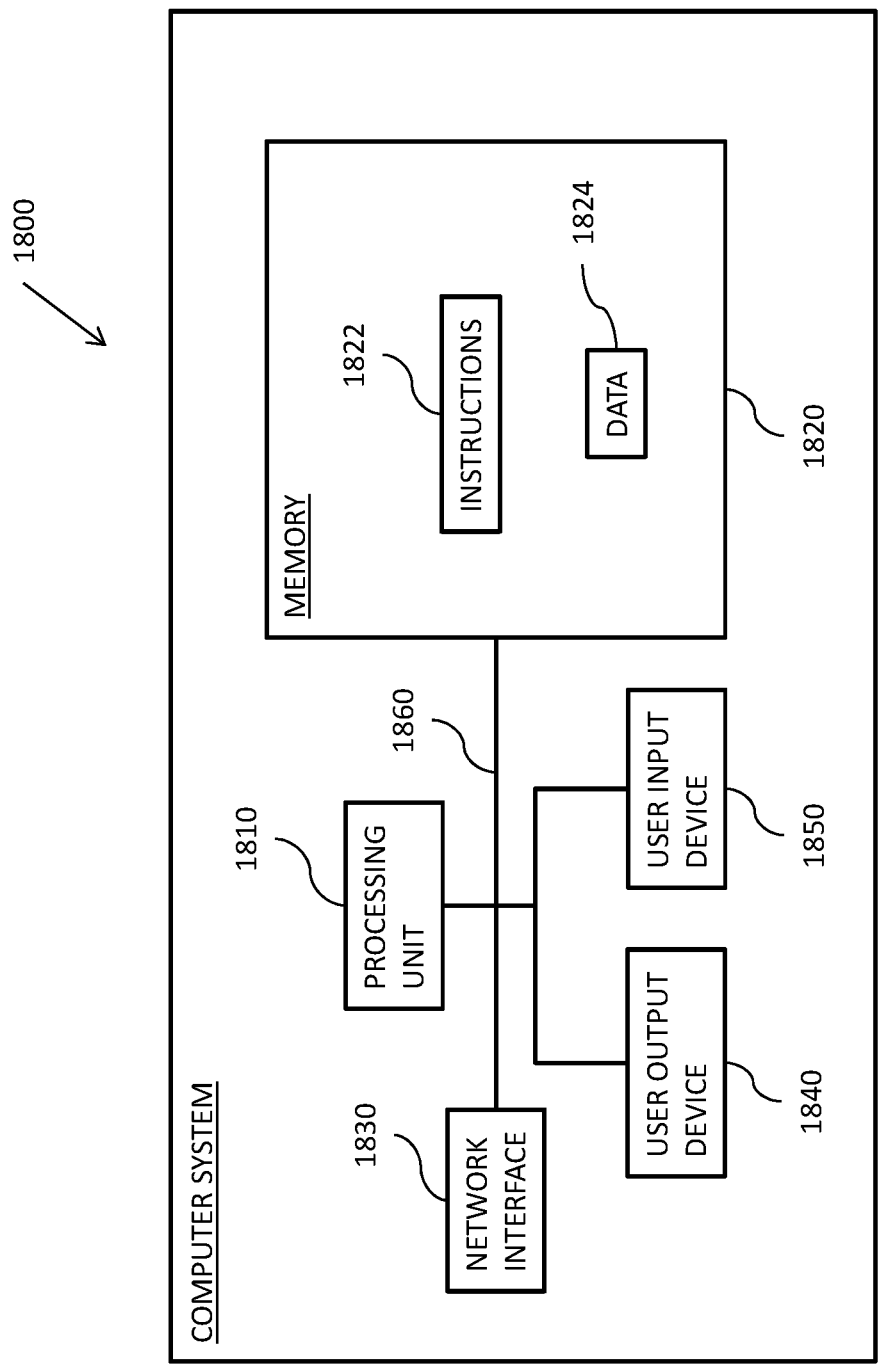
FIG. 18 is a block diagram illustrating selected components of an example computer system for livestock management.

FIG. 18 illustrates selected components of an example computer system 1800 for performing livestock management. System 1800 may, for example, be part of gateway 126 in system 100, controller 830 in tag 800, or controller 1350. Among other things, system 1800 includes a processing unit 1810 and memory 1820, which are coupled together by a network system 1860.

Processing unit 1810 may, for example, include one or more processors (e.g., microprocessors, microcontrollers, field-programmable gate arrays, or application specific integrated circuits). The processors could, for instance, operate according to reduced instruction set computer (RISC) or complex instruction set computer (CISC) principles. Processing unit 1810 may operate according to instructions stored in memory 1820 and/or encoded on processing unit 1810 itself. In general, processing unit 1810 may include any number of devices that can manipulate information in a logical manner.

Memory 1820 may, for example, include random access memory (RAM), read-only memory (ROM), and/or disc memory. Various items may be stored in different portions of the memory at various times. Memory 1830, in general, may be any combination of devices for storing information.

Memory 1820 includes instructions 1822 and data 1824. Instructions 1822 may include an operating system (e.g., Windows, Linux, or Unix) and one or more applications. In certain implementations, applications could include a location analyzer, which may be responsible for determining locations of animals at various times and analyzing their movements, a health analyzer, which may be responsible for determining the health of animals (e.g., based on their movements), and/or a water controller, which may be responsible for controlling the generation of treated water for animals. Data 1824 may include the location data, health assessments, and current operating condition of a water delivery system.

Network interface 1830 may include one or more communication interfaces. A communication interface may, for instance, be a network interface card (whether wireline or wireless) or a modem (whether wireline or wireless). The communication interface may allow data exchange with a data network (e.g., the Internet or an Ethernet) or a phone network (e.g., a cellular network).

System 1800 also includes a user output device 1840 and a user input device 1850. User output device 1840 could, for example, be a display, a speaker, or an indicator (e.g., a light). User input device 1850 could, for example, be a keyboard, a keypad, a touchpad, a stylus, a mouse, or a microphone.

Network system 1860 is responsible for communicating information between processing unit 1810, memory 1820, network interface 1830, user output device 1840, and user input device 1850. Network system 1860 may, for example, include a number of different types of busses (e.g., serial and parallel).

In certain modes of operation, computer system 1800, according to instructions 1822, may monitor the level and/or properties of the water in a water trough, or one or more segments thereof, based on data received from one or more sensors (e.g., in a sensor array). If the computer system determines that the water level in a segment is low, the computer system may activate a water treatment system— for example, by commanding a control valve to an open position (e.g., 25%, 50%, 75%, or 100%). In certain implementations, the computer system may activate a number of control valves (e.g., 3) that accomplish the same task as one control valve. This will allow water to flow to the water treatment unit, which will process the water. After being processed, the treated water will be injected into the segment, perhaps after being injected into a first water trough segment. If the water level in the segment is low, the water will fill the segment until the computer system determines that the water level in the segment is acceptable, based on a reading from level sensor, for example. The computer system will then deactivate the water treatment system (e.g., by commanding the control valve to close), which will shut off water to the water treatment unit and, hence, the water trough. If the water in a subsequent water trough segment is low, then the treated water may fill the first segment first and then begin filling the subsequent segment. Once the computer system determines that the water level in the subsequent segment is acceptable, the computer system will deactivate the water treatment system, shutting off water to the water trough.

The computer system may also use one or more properties of the water in one or more segments to control the water flow thereto. If the computer system determines that a property of the water (e.g., ORP or pH) in a first segment is inappropriate (e.g., high or low), the computer system may activate the water treatment system, which will process the water in the appropriate manner. After being processed, the treated water will be injected into the first segment. If the water properties in the first segment is inappropriate, the water will fill the first segment until the computer system determines that the water properties in the first segment are acceptable. Once the water properties in the first segment are appropriate, the computer system will deactivate the water treatment system, which will shut off water to the water trough. If the water properties in a subsequent segment are inappropriate, then the newly treated water will fill the first segment, and then the second segment will be filled with a mixture of the treated water and the water originally in the first segment, if any. Once the computer system determines that the water properties in the subsequent segment are appropriate, the computer system will deactivate the water treatment system, shutting off water to the water trough.

In particular implementations, the computer system may maintain the water properties in a first segment and a subsequent segment at different levels. For example, the subsequent segment may be the larger of the segments and be kept at a less preferred level (e.g., −200 mV). This will allow general watering of animals, especially when they arrive at the water trough in large groups. The smaller first segment may be kept at a more preferred level (e.g., −400 mV). This water is believed to be preferred by animals, and, hence, should be consumed in larger amounts even though it may occupy less volume in the water trough.

The computer system may also monitor the properties of water from a water source through a water property sensor. For example, the computer system may monitor pH and ORP. By monitoring the properties of the water from the water source, the computer system may determine whether and how to adjust the water treatment unit. For example, if the computer system determines that the water from the water source has a high ORP or low pH, the computer system may command the water treatment unit into a different mode of operation (e.g., higher power). However, if computer system determines that the water from the water source has a low ORP or a high pH, the computer system may command the water treatment unit into another mode of operation (e.g., lower power).

The computer system may also monitor the status of the water treatment unit. For example, by monitoring a flow meter, the computer system may determine when it is time to change the filters and/or plates in the water treatment unit. Additionally, by monitoring the properties of the treated water with a water property sensor, the computer system may determine whether the water treatment unit is functioning properly. For instance, if the water treatment unit is not altering the properties of the water from the water source to the expected degree, it may indicate a problem with the water treatment unit.

The computer system may also control the flow of water to the water trough based on the presence of an animal. As noted above, a proximity sensor may be adapted to determine when an animal is near the water trough, which may be used as a proxy for an animal desiring to drink water. When an animal is near the water trough, the computer system may determine whether the water in the first segment is acceptable. If the water is not acceptable, the computer system may command that a small ratio of the water volume in the water trough, or a segment thereof, be injected into the water trough. Research has shown, for example, that small ratios (e.g., 10-25%) of negative ORP water can drastically change the properties of other water. Thus, by injecting a small portion of treated water, the water in the segment can be made acceptable for the animal.

The computer system may also determine the health status of the animal before determining whether to inject water. In particular implementations, the computer system may receive data (e.g., from an animal analysis system) regarding which animals are potentially unhealthy. This data may, for example, be stored in a table in a database and indexed by animal identifier. When an animal is detected by the proximity sensor, the proximity sensor may read an identifier for the animal (e.g., from a code in an RFID chip or an optical code on a tag) and convey this to the computer system. The computer system may then check the identifier against the data and determine whether the animal is potentially unhealthy. If there is no indication that the animal may be unhealthy, the computer system may take no action regarding the water in the trough. If the animal is potentially unhealthy, however, the computer system may command that treated water be injected into the water trough. This should rapidly adjust the properties of the water to even more beneficial levels (e.g., from −200 mV to −400 mV).

The computer system may also determine the amount of time that an animal spends at the water trough. In implementations where the water trough has a near field sensor, hits from an animal-mounted tag may be treated as drinking/eating times from a trough since the animal's head is so close to the trough (e.g., less than 0.5 m) that it is most likely that they animal is ingesting substance therefrom. The time between visits to the trough may be evaluated in combination with the length of the visits to make a health diagnosis for the animal.

Processing 1810 may implement any of the other procedures discussed herein, to accomplish these operations.

Computer system 1800 provides a variety of features. For example, the system may regulate the distribution of water in an animal watering system to maintain an appropriate amount of water with appropriate properties. Moreover, it may do so for multiple segment of a water trough. Additionally, the computer system may adjust properties of water when an animal approaches. Furthermore, the computer system may compile data from an animal watering system and from each animal being monitored. System 1800 can make proper decisions twenty-four hours a day based on the program determined by the operator of the system. Custom features can be changed based on geographical location and type of animal and breed. Furthermore, a user (e.g., veterinarian or operator) can override the system controls in extreme cases, like an approaching storm or heat wave. If an epidemic episode is foreseen, the user may want to inundate most or all of the animal herd with negative ORP water to maximize the preventative effects of the water to cleanse the herd.

The terminology used herein is for the purpose of describing particular implementations only and is not intended to be limiting. As used herein, the singular form "a", "an", and "the" are intended to include the plural forms as well, unless the context clearly indicates otherwise. It will be further understood that the terms "comprises" and/or "comprising," when used in the this specification, specify the presence of stated features, integers, steps, operations, elements, and/or components, but do not preclude the presence or addition of one or more other features, integers, steps, operations, elements, components, and/or groups therefore.

The corresponding structure, materials, acts, and equivalents of all means or steps plus function elements in the claims below are intended to include any structure, material, or act for performing the function in combination with other claimed elements as specifically claimed. The description of the present implementations has been presented for purposes of illustration and description, but is not intended to be exhaustive or limited to the implementations in the form disclosed. Many modification and variations will be apparent to those of ordinary skill in the art without departing from the scope and spirit of the disclosure. The implementations were chosen and described in order to explain the principles of the disclosure and the practical application and to enable others or ordinary skill in the art to understand the disclosure for various implementations with various modifications as are suited to the particular use contemplated.

A number of implementations have been described for livestock management, and several others have been mentioned or suggested. Moreover, those skilled in the art will readily recognize that a variety of additions, deletions, modifications, and substitutions may be made to these implementations while still achieving livestock management. Thus, the scope of the protected subject matter should be judged based on the following claims, which may capture one or more concepts of one or more implementations.

The invention claimed is:

1. A system for controlling water delivery to an animal water trough, the system comprising:
   a radio-frequency tag adapted to be placed on an animal;
   a first radio-frequency sensor adapted to detect the approach of an animal to a water trough;
   a second radio-frequency sensor adapted to detect the arrival of an animal at the water trough, the second radio-frequency sensor having a shorter detection range than the first radio-frequency sensor; and
   a processor adapted to determine whether an animal is approaching the water trough and inject treated water into the trough before the animal sticks its head in the water trough.

2. The water control system of claim 1, wherein the processor is further adapted to:
   determine the animal's health classification based on whether the animal is approaching the water trough;
   determine whether the animal requires treated water based on the animal's health classification; and
   inject treated water into the trough based on the animal's health classification.

3. The water control system of claim 1, wherein the processor is further adapted to:
   determine whether the trough water is acceptable based on the animal's health classification; and
   inject treated water into the trough based on the acceptability of the trough water.

4. The water control system of claim 1, wherein the processor is further adapted to:
   determine whether the animal arrives at the trough;
   determine when the animal leaves the trough based on whether it arrives at the trough; and
   store the animal's trough arrival time and dwell time.

5. The water control system of claim 4, wherein the processor is further adapted to determine a health classification for the animal based on the time between its visits to the water trough and its dwell time during the visits.

6. The water control system of claim 1, wherein the first radio-frequency sensor is mounted on the water trough.

7. The water control system of claim 1, wherein the second radio-frequency sensor is mounted on the water trough.

8. The water control system of claim 7, wherein the second radio-frequency sensor comprises a coaxial cable with a perforated shield.

9. The water control system of claim 1, further comprising a third radio-frequency sensor adapted to detect the approach of an animal to the water trough, the third radio-frequency sensor having a different detection range than both the first radio-frequency sensor and the second radio-frequency sensor.

10. The water control system of claim 1, wherein the first radio-frequency sensor and the second radio-frequency sensor are mounted on the water trough.

11. The water control system of claim 10, wherein the first radio-frequency sensor is mounted above the water trough, and the second radio-frequency sensor is embedded in the water trough.

12. The water control system of claim 1, wherein the first radio-frequency sensor detects the tag at about 10 m from the trough.

13. The water control system of claim 1, wherein the second radio-frequency sensor detects the tag at about 1 m from the trough.

14. The water control system of claim 1, further comprising an unmanned aerial vehicle adapted to fly over an area where livestock is located and scan for animal mounted tags.

15. The water control system of claim 14, wherein the unmanned aerial vehicle is adapted to sequentially pass over the area to scan the entire area for animal tags.

16. The water control system of claim 14, wherein the unmanned aerial vehicle is adapted to activate a camera if a particular animal is sensed while flying over the area.

17. The water control system of claim 14, wherein the unmanned aerial vehicle may read and write data to a tag on an animal.

18. A method for controlling water delivery for an animal, the method comprising:
 detecting the approach of an animal to a water trough via a first radio-frequency sensor;
 detecting the arrival of an animal at the water trough via a second radio-frequency sensor;
 determining whether an animal is approaching the water trough; and
 injecting treated water into the trough before the animal sticks its head in the water trough.

19. The method of claim 18, further comprising:
 determining the animal's health classification based on whether the animal is approaching the water trough;
 determining whether the animal requires treated water based on its health classification; and
 injecting treated water into the trough based on the animal's health classification.

20. The method of claim 19, further comprising:
 determining whether the trough water is acceptable based on the animal's health classification; and
 injecting treated water into the trough based on the acceptability of the trough water.

21. The method of claim 19, further comprising:
 detecting when the animal leaves the trough based on whether it arrives at the trough; and
 storing the animal's trough visit time and dwell time based on whether the animal arrives at the trough.

22. The method of claim 19, further comprising determining a health classification for the animal based on the time between its visits to the water trough and its dwell time during the visits.

23. The method of claim 18, wherein the first radio-frequency sensor is mounted above the water trough, and the second radio-frequency sensor is embedded in the water trough.

24. The method of claim 23, wherein the second radio-frequency sensor comprises a perforated coaxial cable.

25. The system of claim 1, wherein the controller is adapted to inject the treated water into the water trough before the animal arrives at the water trough.

26. The system of claim 1, wherein the second-radio frequency sensor is adapted to simultaneously detect the arrival of multiple animals at the water trough.

* * * * *